US008798759B2

(12) United States Patent
Goetz et al.

(10) Patent No.: US 8,798,759 B2
(45) Date of Patent: Aug. 5, 2014

(54) USER INTERFACE WITH TOOLBAR FOR PROGRAMMING ELECTRICAL STIMULATION THERAPY

(75) Inventors: Steven M. Goetz, North Oaks, MN (US); Jeffrey T. Keacher, Stanford, CA (US); Rajeev Sahasrabudhe, Maple Grove, MN (US); Wende L. Dewing, Edina, MN (US); Jon P. Davis, St. Michael, MN (US); John Rondoni, Plymouth, MN (US); Gabriela C. Miyazawa, New Brighton, MN (US); Gary W. King, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 1280 days.

(21) Appl. No.: 11/999,722

(22) Filed: Dec. 6, 2007

(65) Prior Publication Data

US 2008/0215118 A1  Sep. 4, 2008

Related U.S. Application Data

(60) Provisional application No. 60/873,193, filed on Dec. 6, 2006.

(51) Int. Cl.
*A61N 1/00* (2006.01)
(52) U.S. Cl.
USPC .......................................................... 607/59
(58) Field of Classification Search
USPC ............. 607/2, 59, 45, 46, 48, 115, 116, 117
See application file for complete search history.

(56) References Cited

U.S. PATENT DOCUMENTS

| 4,793,353 | A | | 12/1988 | Borkan |
| 5,733,312 | A | | 3/1998 | Schloss et al. |
| 5,938,690 | A | * | 8/1999 | Law et al. ...................... 607/46 |
| 5,983,140 | A | | 11/1999 | Smith et al. |

(Continued)

FOREIGN PATENT DOCUMENTS

| EP | 0 773 038 B1 | 5/1997 |
| WO | WO 01/83028 A1 | 11/2001 |
| WO | 2004/041351 A1 | 5/2004 |
| WO | WO2004/045711 A1 | 6/2004 |

OTHER PUBLICATIONS

Office Action for U.S. Appl. No. 11/698,746, mailed May 15, 2009, 7 pages.

(Continued)

*Primary Examiner* — Christopher D Koharski
*Assistant Examiner* — Roland Dinga
(74) *Attorney, Agent, or Firm* — Shumaker & Sieffert, P.A.

(57) ABSTRACT

The disclosure is directed to a user interface with a menu that facilitates stimulation therapy programming. The user interface displays a representation of the electrical leads implanted in the patient and at least one menu with icons that the user can use to adjust the stimulation therapy. The user may drag one or more field shapes from a field shape selection menu onto the desired location relative to the electrical leads. A manipulation tool menu may also allow the user to adjust the field shapes placed on the electrical leads, which represent the stimulation region. The programmer that includes the user interface then generates electrical stimulation parameter values for the stimulator to deliver stimulation according to the field shapes or field shape groups defined/located by the user. The field shapes may represent different types of stimulation representations, such as current density, activation functions, and neuron models.

25 Claims, 29 Drawing Sheets

(56) References Cited

U.S. PATENT DOCUMENTS

| | | | | |
|---|---|---|---|---|
| 6,052,624 | A * | 4/2000 | Mann | 607/46 |
| 6,106,464 | A | 8/2000 | Bass et al. | |
| 6,308,102 | B1 | 10/2001 | Sieracki et al. | |
| 6,381,496 | B1 | 4/2002 | Meadows et al. | |
| 6,393,325 | B1 * | 5/2002 | Mann et al. | 607/46 |
| 6,609,032 | B1 * | 8/2003 | Woods et al. | 607/46 |
| 6,622,048 | B1 * | 9/2003 | Mann et al. | 607/46 |
| 6,659,968 | B1 | 12/2003 | McClure | |
| 6,909,917 | B2 | 6/2005 | Woods et al. | |
| 7,033,326 | B1 | 4/2006 | Pianca et al. | |
| 7,035,690 | B2 * | 4/2006 | Goetz | 607/46 |
| 7,386,348 | B2 | 6/2008 | North et al. | |
| 7,657,319 | B2 * | 2/2010 | Goetz et al. | 607/59 |
| 7,848,802 | B2 | 12/2010 | Goetz et al. | |
| 7,933,655 | B2 | 4/2011 | Sieracki et al. | |
| 2001/0007950 | A1 * | 7/2001 | North et al. | 607/59 |
| 2002/0116036 | A1 * | 8/2002 | Daignault et al. | 607/59 |
| 2004/0034394 | A1 | 2/2004 | Woods et al. | |
| 2004/0215286 | A1 * | 10/2004 | Stypulkowski | 607/48 |
| 2005/0070781 | A1 | 3/2005 | Dawant et al. | |
| 2006/0017749 | A1 | 1/2006 | McIntyre et al. | |
| 2006/0020297 | A1 | 1/2006 | Gerber et al. | |
| 2006/0094951 | A1 | 5/2006 | Dean et al. | |
| 2006/0229687 | A1 * | 10/2006 | Goetz et al. | 607/46 |
| 2007/0055322 | A1 * | 3/2007 | Forsberg et al. | 607/59 |
| 2007/0203544 | A1 * | 8/2007 | Goetz et al. | 607/59 |
| 2007/0213790 | A1 | 9/2007 | Nolan et al. | |
| 2008/0103407 | A1 | 5/2008 | Bolea et al. | |

OTHER PUBLICATIONS

Responsive Amendment to Office Action for U.S. Appl. No. 11/698,746, filed Aug. 14, 2009, 12 pages.
Office Action for U.S. Appl. No. 11/698,746, mailed Mar. 2, 2010, 7 pages.
Responsive Amendment to Office Action for U.S. Appl. No. 11/698,746, filed Jun. 2, 2010, 15 pages.
Office Action for U.S. Appl. No. 11/999,735, mailed May 10, 2010, 11 pages.
Reply to Written Opinion for corresponding patent application No. PCT/2007/024977, filed Oct. 3, 2008, 11 pages.
Reply to Written Opinion for patent application No. PCT/2007/024969, filed Oct. 21, 2008, 10 pages.
Final Office Action for U.S. Appl. No. 11/698,746, mailed Oct. 7, 2010, 9 pages.
Response to Final Office Action for U.S. Appl. No. 11/698,746, filed Dec. 7, 2010, 6 pages.
Final Office Action for U.S. Appl. No. 11/999,735, mailed Oct. 25, 2010, 8 pages.
Response to Final Office Action for U.S. Appl. No. 11/999,735, filed Dec. 23, 2010, 14 pages.
Office Action for U.S. Appl. No. 11/999,726, mailed Oct. 4, 2010, 14 pages.
Response to Office Action for U.S. Appl. No. 11/999,726, filed Jan. 4, 2011, 19 pages.
O'Halloran et al., "Modified implanted drop foot stimulator system with graphical user interface for customized stimulation pulse-width profiles," Medical & Biological Engineering and Computing, vol. 41, 2003, pp. 701-709.
Popovic et al., "Modular transcutaneous functional electrical stimulation system," Medical Engineering & Physics, vol. 27, 2005, pp. 81-92.
North et al., "Automated, Patient-Interactive, Spinal Cord Stimulator Adjustment: A Randomized Controlled Trial," Neurosurgery, vol. 52, No. 3, Mar. 2003, pp. 572-580.
Notification of Transmittal of the International Preliminary Report on Patentability for corresponding patent application No. PCT/2007/024977, mailed Nov. 14, 2008, 11 pages.
European Examination Report for European Application No. 07 862 567.0-2305, dated Oct. 19, 2009, 2 pages.
Reply to Written Opinion for patent application No. PCT/US2007/008697, filed Jun. 12, 2008, (8 pages).
Office Action from U.S. Appl. No. 11/999,726, dated Apr. 6, 2011, 9 pp.
Response to Office Action dated Apr. 6, 2011, from U.S. Appl. No. 11/999,726, filed Jul. 6, 2011, 10 pp.
Notification of Transmittal of the International Search Report and the Written Opinion of the International Searching Authority, or the Declaration, for corresponding patent application No. PCT/2007/024977, mailed Jul. 8, 2008, 12 pages.
Honeywell Inc. Systems and Research Division Research Department, "Experimental Evaluation of Symbolic and Pictorial Displays for Submarine Control," U.S. Dept. of Commerce Nat'l Technical Info. Service, Sep. 1965, 120 pages.
U.S Appl. No. 11/698,746, entitled "Graphical Configuration of Electrodes for Electrical Stimulation", filed Jan. 26, 2007, Jeffrey T. Keacher.
U.S. Appl. No. 11/591,176, entitled "User Interface With An Atlas for Configuring Stimulation Therapy", filed Oct. 31, 2006, Richard T. Stone et al.
U.S. Appl. No. 11/591,281, entitled "User Interface With 3D Environment for Configuring Stimulation Therapy", filed Oct. 31, 2006, Richard T. Stone et al.
U.S. Appl. No. 11/591,178, entitled "User Interface With 2D Views for Configuring Stimulation Therapy", filed Oct. 31, 2006, Richard T. Stone et al.
U.S. Appl. No. 11/591,299, entitled "Electrical and Activation Field Models for Configuring Stimulation Therapy", filed Oct. 31, 2006, Richard T. Stone et al.
U.S. Appl. No. 11/591,193, entitled "Stimulation Templates for Configuring Stimulation Therapy", filed Oct. 31, 2006, Richard T. Stone et al.
U.S. Appl. No. 11/591,188, entitled "Programming Interface With A Cross-Sectional View of a Stimulation Lead With Complex Electrode Array Geometry", filed Oct. 31, 2006, Steven M. Goetz et al.
U.S. Appl. No. 11/591,280, entitled "Programming Interface With A Concentric Axial View of a Stimulation Lead With Complex Electrode Array Geometry", filed Oct. 31, 2006, Steven M. Goetz et al.
U.S. Appl. No. 11/591,170, entitled "Programming Interface With An Unwrapped 2D View of a Stimulation Lead With Complex Electrode Array Geometry", filed Oct. 31, 2006, Steven M. Goetz et al.
U.S. Appl. No. 11/591,189, entitled "Stimulation Templates for Programming a Stimulation Lead With Complex Electrode Array Geometry", filed Oct. 31, 2006, Steven M. Goetz et al.
U.S. Appl. No. 11/591,187, entitled "Electrical And Activation Field Models for Programming A Stimulation Lead With Complex Electrode Array Geometry", filed Oct. 31, 2006, Steven M. Goetz et al.
U.S. Appl. No. 11/999,735, entitled "User Interface With Toolbar for Programming Electrical Stimulation Therapy", filed Dec. 6, 2007, Steven M. Goetz et al.
U.S. Appl. No. 11/999,726, entitled "User Interface With Toolbar for Programming Electrical Stimulation Therapy", filed Dec. 6, 2007, Steven M. Goetz et al.
Office Action from U.S. Appl. No. 11/999,726, dated Sep. 7, 2011, 16 pp.
Response to Office Action dated Sep. 7, 2011, from U.S. Appl. No. 11/999,726, filed Nov. 7, 2011, 15 pp.
Office Action from U.S. Appl. No. 11/999,735, dated Sep. 7, 2011, 12 pp.
POPOVIC, "Modular transcutaneous functional electrical stimulation system," Medical Engineering & Physics 27 (2005): 81-92.
Response to office action for U.S. Appl. No. 11/999,735, filed Jan. 4, 2012, 12 pages.
Office Action from U.S. Appl. No. 13/271,525, dated Dec. 19, 2011, 8 pp.
Response to Office Action dated Dec. 19, 2011, from U.S. Appl. No. 13/271,525, filed Mar. 19, 2012, 14 pp.
Office Action from U.S. Appl. No. 11/999,735, dated Feb. 1, 2012, 10 pp.
Response to Office Action dated Feb. 1, 2012, from U.S. Appl. No. 11/999,735, filed Apr. 2, 2012, 6 pp.

* cited by examiner

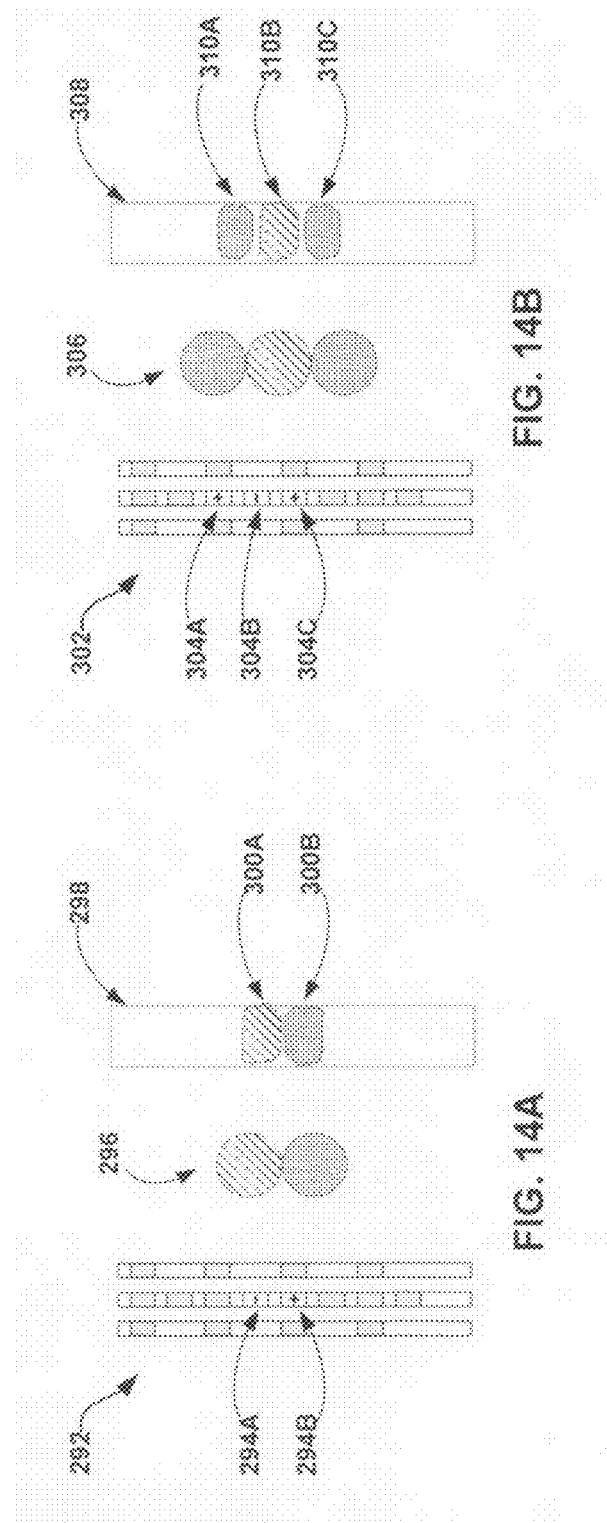
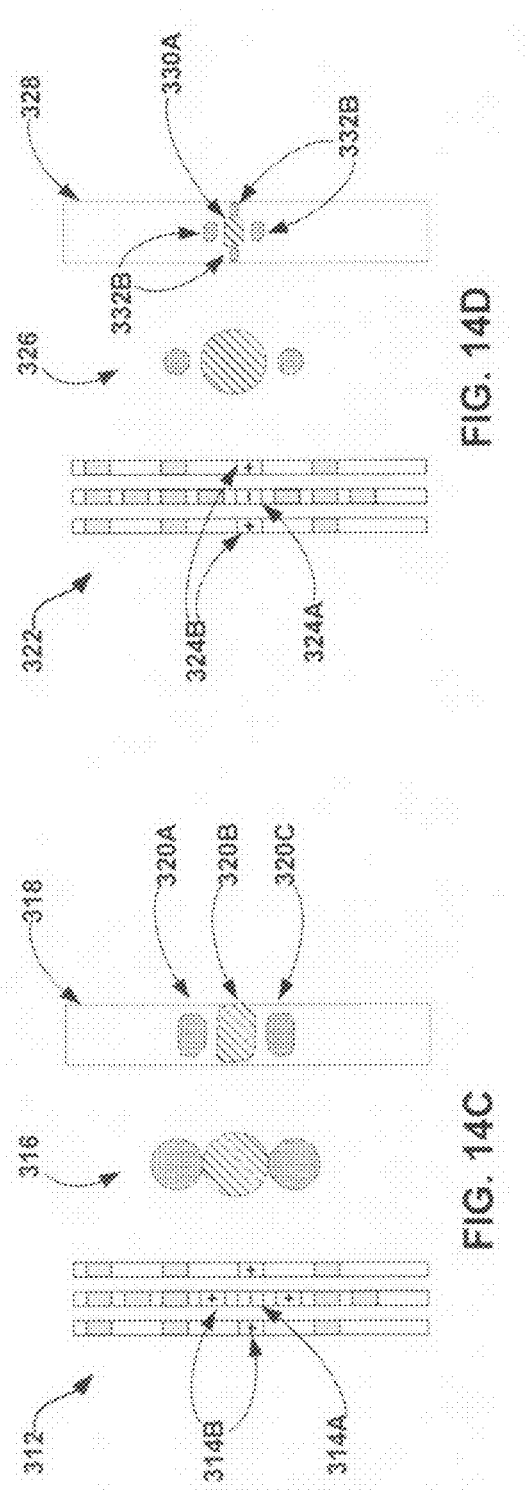
FIG. 14A  FIG. 14B  FIG. 14C  FIG. 14D

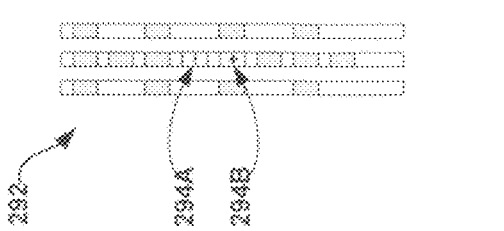
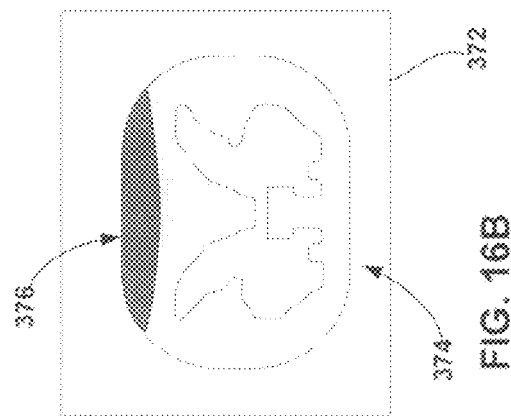
FIG. 16A
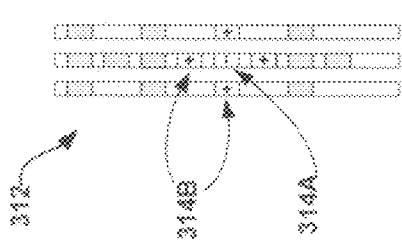
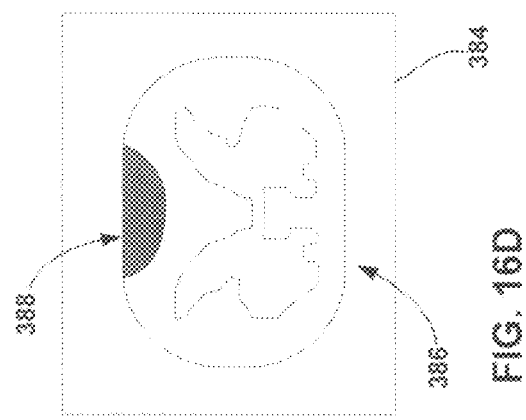
FIG. 16B
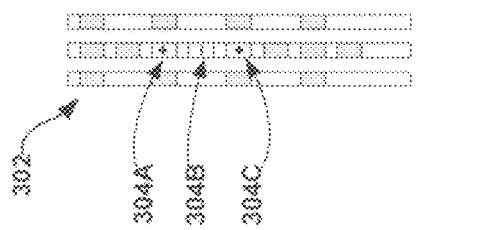
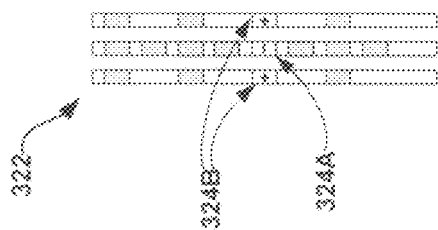
FIG. 16C
FIG. 16D

USER INTERFACE WITH TOOLBAR FOR PROGRAMMING ELECTRICAL STIMULATION THERAPY

This application claims the benefit of U.S. Provisional Application No. 60/873,193, filed Dec. 6, 2006, the entire content of which is incorporated herein by reference.

TECHNICAL FIELD

The disclosure relates to electrical stimulation therapy, and more particularly, to programming electrical stimulation therapy.

BACKGROUND

Implantable electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more leads that include electrodes located proximate to target locations associated with the brain, the spinal cord, pelvic nerves, peripheral nerves, or the gastrointestinal tract of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES), to promote muscle movement or prevent atrophy.

In general, a clinician selects values for a number of programmable parameters in order to define the electrical stimulation therapy to be delivered by the implantable stimulator to a patient. For example, the clinician ordinarily selects a combination of the electrodes carried by one or more implantable leads, and assigns polarities to the selected electrodes. The selected combination of electrodes and their polarities may collectively be referred to as an electrode configuration. In addition, the clinician selects an amplitude, which may be a current or voltage amplitude, and, in the case of stimulation delivered the patient in the form of electrical pulses, a pulse width and a pulse rate. A group of parameters, such as a group including electrode combination, electrode polarity, amplitude, pulse width and pulse rate, may be referred to as a program in the sense that they drive the neurostimulation therapy to be delivered to the patient. In some applications, an implantable stimulator may deliver stimulation therapy according to multiple programs either simultaneously or on a time-interleaved, overlapping or non-overlapping, basis.

The process of selecting electrode combinations and other stimulation parameters can be time consuming, and may require a great deal of trial and error before a therapeutic program is discovered. The "best" program may be a program that best balances greater clinical efficacy and minimal side effects experienced by the patient. In addition, some programs may consume less power during therapy. The clinician typically needs to test a large number of possible electrode combinations within the electrode set implanted in the patient in order to identify an optimal combination of electrodes and associated polarities. As mentioned previously, an electrode combination is a selected subset of one or more electrodes located on one or more implantable leads coupled to an electrical stimulator. As a portion of the overall parameter selection process, the process of selecting electrodes and the polarities of the electrodes can be particularly time-consuming and tedious.

The clinician may test electrode combinations by manually specifying combinations based on intuition or some idiosyncratic methodology. The clinician may then record notes on the efficacy and side effects of each combination after delivery of stimulation via that combination. In some cases, efficacy and side effects can be observed immediately within the clinic. For example, spinal cord stimulation may produce paresthesia and side effects that can be observed by the clinician based on patient feedback. In other cases, side effects and efficacy may not be apparent until a program has been applied for an extended period of time, as is sometimes the case in deep brain stimulation. Upon receipt of patient feedback and/or observation of symptoms by the clinician, the clinician is able to compare and select from the tested electrode combinations.

In order to improve the efficacy of stimulation therapy, electrical stimulators have grown in capability and complexity. Modern stimulators tend to have larger numbers of possible electrode combinations, larger parameter ranges, and the ability to simultaneously deliver multiple programs by interleaving stimulation pulses according to different programs in time. Although these factors increase the clinician's ability to more finely adjust therapy for a particular patient or disease state, the burden involved in optimizing the device parameters has similarly increased. Unfortunately, fixed reimbursement schedules and scarce clinic time present challenges to effective programming of stimulation therapy.

Existing lead sets include axial leads carrying ring electrodes disposed at different axial positions, and so-called "paddle" leads carrying planar arrays of electrodes. Selection of electrode combinations within an axial lead, a paddle lead, or among two or more different leads presents a challenge to the clinician. The emergence of more complex electrode array geometries presents still further challenges. The design of the user interface used to program the stimulator, in the form of either a physician programmer or patient programmer, has a great impact on the ability to efficiently define and select efficacious stimulation programs.

SUMMARY

The disclosure is directed to a user interface with a toolbar, or menu, that facilitates stimulation therapy programming for a user. The user interface may display a representation of the implanted electrical leads in the patient in conjunction with at least one menu with icons that the user can use to adjust the stimulation field of the stimulation therapy with one or more field shape groups. One menu may be a field shape selection menu that provides field shapes to indicate the resulting stimulation field according to initial stimulation parameters. Another menu may be a manipulation tool menu that allows a user to perform certain actions on the field shapes to adjust the stimulation therapy. The user interface is designed to reduce the need for the user to directly adjust stimulation parameters by focusing on the tissue and therapy result.

The user may drag one or more field shapes or field shape groups from the field shape selection menu onto the desired location of the electrical leads or elsewhere within the representation of the stimulation region. The manipulation tool menu may also allow the user to adjust the field shapes placed within the representation of the stimulation region, which represent the overall stimulation field within the representation of the stimulation region presented by the user interface. The representation of the stimulation region may be mapped to implanted electrodes, anatomy, or the like in an actual stimulation region within the patient. The programmer that includes the user interface then generates electrical stimulation parameters for an implantable stimulator to deliver stimulation therapy according to the field shapes defined by the user and their position within the representation of the stimulation region. The field shapes may represent different types of stimulation fields, such as current density, activation functions, and neuron models.

In one example, the disclosure provides a method for presenting on a display at least one view of a representation of a stimulation region and presenting on the display at least one field shape group within a field shape selection menu. The method also includes receiving input selecting the at least one field shape group from the field shape selection menu, receiving placement input placing the at least one field shape group at a position within the stimulation region, and generating electrical stimulation parameters based upon the field shape group and the position within the representation of the stimulation region.

In another example, the disclosure provides a programmer having a display and a processor that presents on the display at least one view of a representation of a stimulation region and at least one field shape group within a field shape selection menu. The programmer also includes a user interface that receives selection input selecting the at least one field shape group from the field shape selection menu and placement input placing the at least one field shape group at a position within the stimulation region, wherein the processor generates electrical stimulation parameters based upon the field shape group and the position within the representation of stimulation region.

In an alternative example, the disclosure provides a computer readable medium having instructions that cause a processor to present on a display at least one view of a representation of a stimulation region and present on the display at least one field shape group within a field shape selection menu. The computer readable medium also has instructions that cause the processor to receive selection input selecting the at least one field shape group from the field shape selection menu, receive placement input placing the at least one field shape group at a position within the stimulation region, and generate electrical stimulation parameters based upon the field shape group and the position within the representation of the stimulation region.

The disclosure, in various examples, may be capable of providing a number of advantages. In general, the disclosure may allow a user, e.g., a clinician, to focus on desired tissue changes that should occur from the stimulation therapy instead of stimulation parameters that need to be found in order to create the desired therapy result. In other words, the clinician may specify a desired result and permit a programming system to select parameters to achieve the result. This approach may reduce the time required for trial and error during stimulation therapy programming sessions. In addition, the user interface may use field shapes that indicate in what manner the tissue will be affected by the stimulation. For example, an activation field shape may indicate which tissue near the cathode will be activated while an inhibition field shape may indicate which tissue near the anode will be inhibited. The user may be able to adjust the field shapes until the final field shape combinations and resulting stimulation field are representative of the desired stimulation therapy.

The details of one or more embodiments of the disclosure are set forth in the accompanying drawings and the description below. Other features, objects, and advantages of the disclosure will be apparent from the description and drawings, and from the claims.

BRIEF DESCRIPTION OF THE DRAWINGS

FIGS. 14A-14D are conceptual illustrations of electrode configurations and corresponding activation icons and neuron models.

FIGS. 16A-16D are conceptual illustrations of electrode configurations and corresponding activation depths.

DETAILED DESCRIPTION

Figure 1:
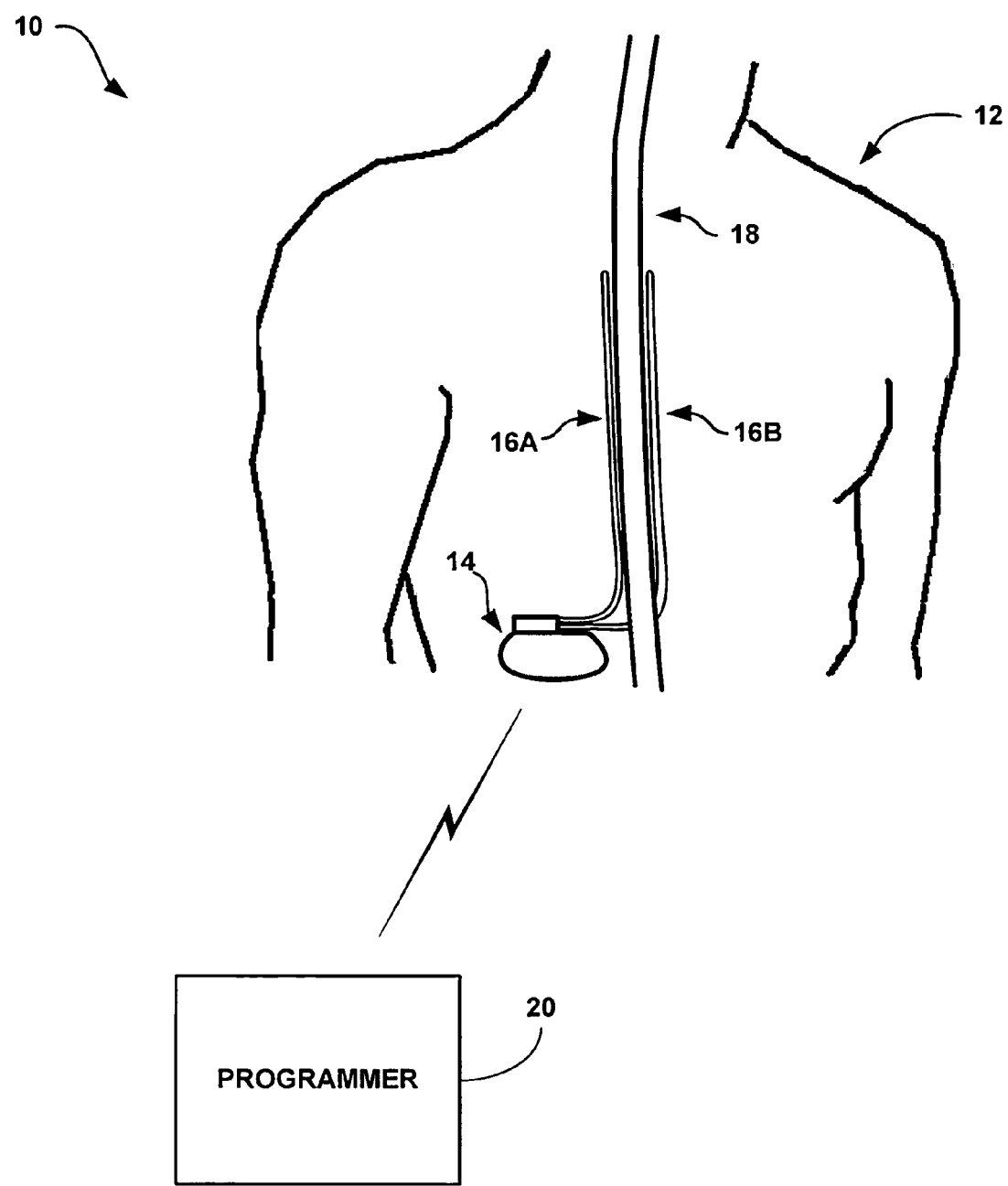
FIG. 1 is a conceptual diagram of an implantable electrical stimulator for delivering stimulation therapy and an associated external programmer.

The user interface described herein facilitates the programming of stimulation parameters by focusing the efforts of the clinician to the desired stimulation field produced by electrical stimulation instead of the individual parameters needed to produce the stimulation field. The user interface comprises a stimulation region that may include a representation of the implanted electrical leads, a representation of a template, a representation of a patient image, or any other representation to aid the clinician in defining the stimulation field. The user interface may also include at least one toolbar, which may be presented adjacent to the implanted electrical leads. The clinician may select field shapes from the toolbar, and drag the field shapes to a desired location over the implanted electrical leads. The field shapes, so located, represent the stimulation field that will be produced by stimulation parameters generated to match the field shapes and locations. In addition, the clinician may select actions or icons from the toolbar that modify or move the field shapes in the stimulation region to create a stimulation field desired by the clinician. A programmer may generate stimulation parameters as needed to match the stimulation field created by the clinician.

The field shapes that represent the overall stimulation field may be in different forms to show alternative representations/effects of the field. For example, the field shapes may illustrate current density, neural or other activation and/or inhibition, a neuron model, or other methods of displaying the stimulation field or its effect on patient during stimulation therapy. In this manner, the clinician may not need to manually set stimulation parameters such as the electrode configuration, pulse width, pulse rate, and voltage or current amplitude. Instead, the programmer automatically determines the stimulation parameters based upon the field shapes that make up the overall stimulation field created by the user, and the locations of the field shapes. In some embodiments, the clinician may have the ability to select a manual mode for direct selection of stimulation parameters, either alone, or in conjunction with parameters selected automatically by the programmer according to field shapes specified by the clinician. Allowing the user to program stimulation therapy by viewing an estimation of the resulting therapy with a stimulation field before applying the therapy to a patient may reduce the knowledge, training, and time needed to select a stimulation program sufficient to effectively treat the patient.

The disclosure presents various programming methods. In some examples, the methods may include presenting on a display at least one view of a representation of an implantable lead within a stimulation region and presenting on a display at least one icon that is used to specify adjustments to a stimulation field. The method may also include receiving user input defining and locating the stimulation field with the at least one icon and generating electrical stimulation parameters based upon the user input. The disclosure also contemplates programming devices, including programming devices that implement methods as described herein, as well as systems including one or more programming devices and one or more electrical stimulators programmed using such devices. The electrical stimulators may be implantable and may deliver electrical stimulation in the form of electrical stimulation pulses or substantially continuous electrical stimulation waveforms. In addition, the disclosure contemplates stimulators equipped to deliver stimulation via various electrode configurations and with various parameters as described herein, including stimulators capable of delivering stimulation that corresponds to various field shapes defined by a user via a graphical user interface as described in this disclosure.

FIG. 1 is a conceptual diagram of an example system 10 comprising an implantable electrical stimulator 14 for delivering stimulation therapy and an associated external programmer 20. As shown in FIG. 1, implantable stimulator 14 is coupled to electrical leads 16A and 16B (collectively "leads 16"). Implantable stimulator 14 is implanted within a patient 12. Leads 16 are implanted along the length of spinal cord 18 such that electrical stimulation from leads 16 affects the spinal cord. Programmer 20 is used by a user to create one or more customized programs that define the electrical stimulation delivered to patient 12 by stimulator 14. Programmer 20 communicates with stimulator 14 to, for example, provide stimulator 14 the programs created using the programmer. Stimulator 14 generates and delivers electrical stimulation therapy according to the programs to treat a variety of patient conditions such as chronic pain.

The creation of a stimulation field with field shapes, or field shape icons, is primarily described herein with respect to spinal cord stimulation (SCS) therapy. However, the invention is not limited to embodiments that provide SCS. Rather, embodiments according to the invention may be directed to stimulation of any tissue within patient 12. For example, embodiments may provide spinal cord stimulation (SCS), deep brain stimulation (DBS), gastric stimulation, pelvic nerve stimulation (e.g., sacral, pudendal, iliohypogastric, ilioinguinal, dorsal, peritoneal, or the like), peripheral nerve stimulation, peripheral nerve field stimulation (e.g., occipital, trigeminal, or the like), or any other type of electrical stimulation therapy. While the configuration and/or location of a stimulator 14 and/or leads 16 may be different depending on the specific application of system 10, programmer 20 may still function according to its description herein.

Stimulator 14 delivers stimulation according to a program, i.e., a set of values for a number of parameters that define the stimulation delivered according to that stimulation program or parameter set, which may include voltage or current pulse amplitudes, pulse widths, pulse rates, and information identifying which electrodes (not shown) on leads 16 have been selected for delivery of pulses, and the polarities of the selected electrodes, i.e., an electrode configuration. Each set of stimulation parameters is stored as a program in stimulator 14 or programmer 20. Multiple programs may be stored to allow patient 12 to evaluate multiple programs during the course of therapy, or use specific programs during certain activities such as sleeping, sitting, or walking. Stimulator 14 may even track the usage of each program, or provide changes to the currently used program based upon patient feedback, a malfunction of lead 16A or 16B, or any other reason for changing the program.

Leads 16 may be any type of electrical stimulation lead with one or more electrodes (not shown) along the length and/or proximate to the distal ends of the lead. Leads 15 may also include a connector at the proximate end of the leads. The electrodes may be "ring electrodes," e.g., electrodes that create a cylinder around the exterior of leads 16. Leads 16 may, in some examples, be in the form of paddle leads or other shapes different than that shown in FIG. 1. In addition to embodiments including two leads 16, as illustrated in FIG. 1, other embodiments may include only one or more than two leads 16 implanted within patient 12.

In other examples, leads 16 may include a complex electrode array geometry. A complex electrode array geometry may include partial ring electrodes, segmented electrodes, or other electrodes that are limited to a portion of the perimeter of the lead. A complex electrode array geometry may allow the clinician to target a stimulation field at a certain circumferential position around the perimeter of the lead, instead of producing a stimulation field around the entire perimeter, as is typical with ring electrodes. The production of a precise stimulation field may improve stimulation efficacy and reduce adverse side effects resulting from stimulation of untargeted tissues.

Programmer 20 is an external programmer that can be used to create stimulation programs using the user interface (not shown) provided by the programmer. Programmer 20 may be either a clinician programmer or a patient programmer, but programmer 20 will be generally described as a clinician programmer herein. In some embodiments, a patient programmer may have limited functionality or certain safeguards that prevent patient 12 from causing injury with stimulator 14. In the case of a clinician programmer, the clinician interacts with programmer 20 to create a visual representation of a stimulation field, utilizing the field shapes and other tools described herein, that may treat patient 12. Programmer 20 then generates stimulation parameters automatically based upon the created stimulation field and transmits the stimulation parameters to stimulator 14 as a single program. For example, the created stimulation field representation may be mapped to or correlated with the stimulation parameters, e.g., electrode configuration (combination and polarities), pulse rate, pulse width, amplitude, and duration (if applicable) necessary to produce the stimulation field in the patient.

Programmer 20 communicates with stimulator 14 via wireless communications during initial programming of stimulator 14, further follow-up programming, or retrieving data collected by the stimulator. Wireless communication between stimulator 12 and programmer 20 may occur using radio frequency (RF) telemetry techniques known in the art. Furthermore, wireless communications between stimulator 14 and programmer 20 may occur using any of a variety of local wireless communication techniques, such as RF communication according to the Institute of Electrical and Electronic (IEEE) 802.11 or Bluetooth specification sets, infrared communication according to the Infrared Data Association (IRDA) specification set, or other standard or proprietary communication protocols.

As an example, programmer 20 may be embodied as a hand-held computing device that the clinician may easily transport throughout the clinic, hospital, or any other location. However, programmer 20 may alternatively be embodied as any type of device. In various embodiments, programmer 20 may be a tablet-based computing device, a personal digital assistant (PDA), a notebook computer, a desktop computing device, a workstation, or any other computing device capable of the functions described herein. Programmer 20 may be used by the clinician in a clinic, and additionally or alternatively used by patient 12 or a caregiver at the patient's home, the clinic, or other facility of patient 12.

Figure 2:
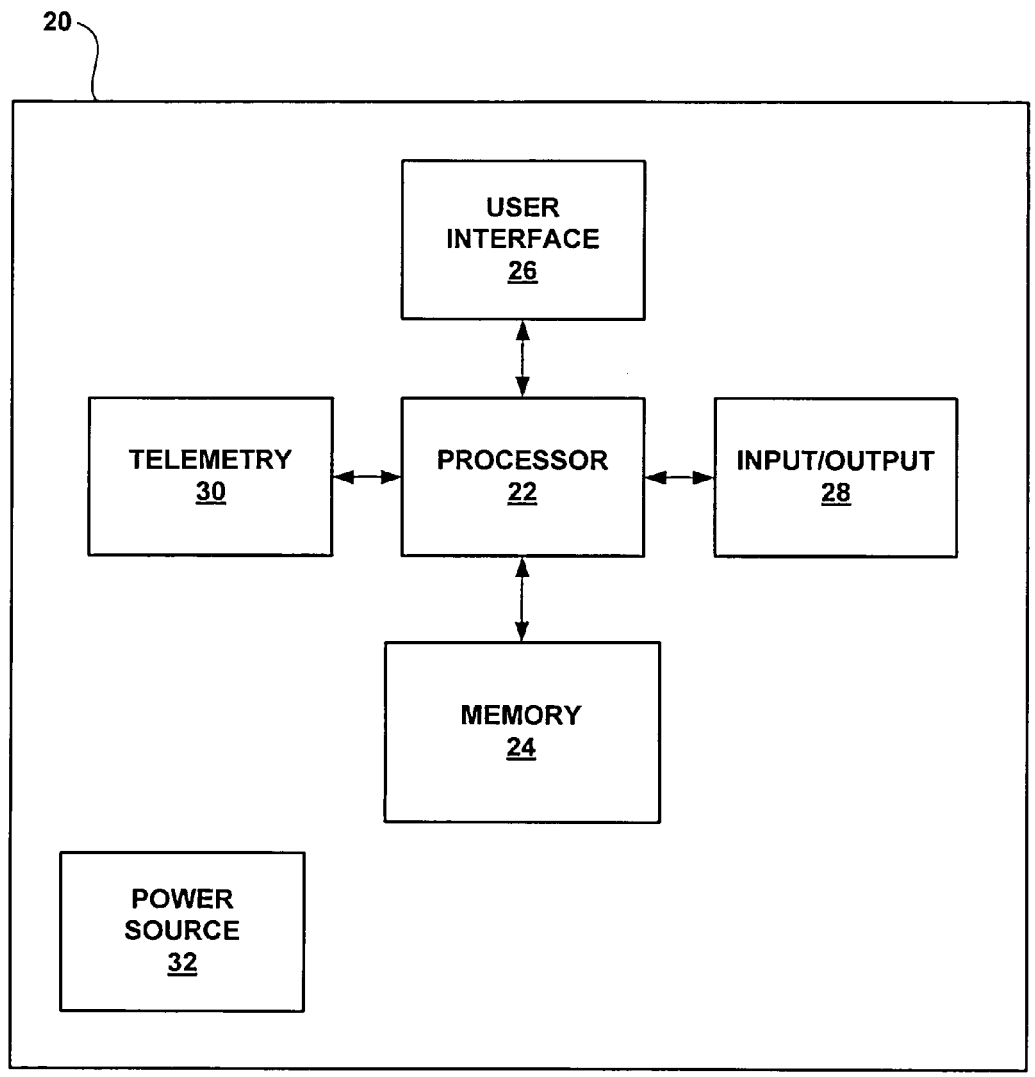
FIG. 2 is a block diagram of an external programmer that facilitates user directed programming of stimulation therapy.

FIG. 2 is a block diagram further illustrating example external programmer 20 that facilitates user directed programming of stimulation therapy. As shown in FIG. 2, programmer 20 may include a processor 22, memory 24, user interface 26, input/output module 28, telemetry module 30, and power source 32. Processor 22 controls the functioning of programmer 20 in the manner described herein according to the instructions stored in memory 24. A user interacts with user interface 26, and data is sent to and received from stimulator 14 via telemetry module 30. The clinician may also use input/output module 28 to exchange data with other computing devices without using telemetry module 30. Power source 32 may be a battery that provides power to some or all of the components of programmer 20.

In the example of FIG. 2, memory 24 stores programs, including those created by the clinician or other user, e.g., patient 12, using the techniques described herein. As discussed above, the programs stored in memory 24 specify electrode configurations (combinations and polarities), and other stimulation parameters. Processor 22 may download the programs to implantable stimulator 20 via telemetry module 30. Memory 24 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In addition to stimulation programs, memory 24 may store instructions that support the operation of programmer 20 through processor 22. Processor 22 may use the instructions stored within memory 24 to control user interface 26, how stimulation fields are created, how programs are created, communications via telemetry module 30, data transfer via input/output module 28, and power management with power source 32. Memory 24 may include separate sub memories to store different information in some examples, while other examples of memory 24 may only include one memory.

The clinician interacts with processor 22 via user interface 26 in order to identify efficacious electrode configurations and other stimulation parameters as described herein. Processor 22 may provide a graphical user interface (GUI) (not shown in FIG. 2), via user interface 26 to facilitate interaction with the clinician. Processor 22 may include a microprocessor, a microcontroller, a digital signal processor (DSP), an application specific integrated circuit (ASIC), a field-programmable gate array (FPGA), or other discrete or integrated logic circuitry. User interface 26 may include one or more input media, such as a keyboard, keypad, mouse or other pointing device, or a touch screen display. In addition, user interface 26 may include output media such as a display, speaker, lights, audible alerts, or tactile alerts.

Processor 22 controls stimulator 14 via telemetry module 30 to test created stimulation programs by controlling the stimulator to deliver stimulation to patient 12 via the selected electrode combinations and according to the other parameters specified by the programs. In particular, processor 22 transmits programming signals to implantable stimulator 14 via telemetry module 30. Processor 22 may send one or more programs to stimulator 14 and the stimulator may deliver therapy according to one of the programs without further input from programmer 20. However, processor 22 may communicate with stimulator 14 in real-time via telemetry module 30 in order to immediately observe the programming change in patient 12. In some cases, changes to stimulation may not be immediately evident. In such cases, a change may be activated and evaluated over a period of minutes, hours, or days before another change is initiated.

Finalized programs may be transmitted by processor 22 via telemetry module 30 to stimulator 14. Alternatively, programs may be stored in stimulator 14 and modified or selected using instructions transmitted by processor 22 via telemetry module 30 to the stimulator. The one or more programs may be stored in a memory of stimulator 14 or another programmer used by patient 12, e.g., a patient programmer. In any case, stimulator 14 may selectively use any of the stimulation programs created by the clinician using the field shapes and the related techniques described herein. Either the clinician or patient 12 may adjust the stimulation programs over time or create new stimulation programs in order to find efficacious stimulation programs with acceptable or no side effects.

Again, programmer 20 may be provided in the form of a handheld device, tablet computer, portable computer, laptop computer, personal desktop computer, or workstation. In each case, programmer 20 provides user interface 26 to a clinician or patient. User interface 26 may include or provide a graphical user interface (UI), and include any combination of audible, visual, and tactile input and output media. The clinician or patient 12 interacts with user interface 26 to program stimulation parameters for implantable stimulator 14 via external programmer 20. Hence, various aspects of user interface 26 described herein may be provided via a clinician programmer, a patient programmer, or both.

Figure 3:
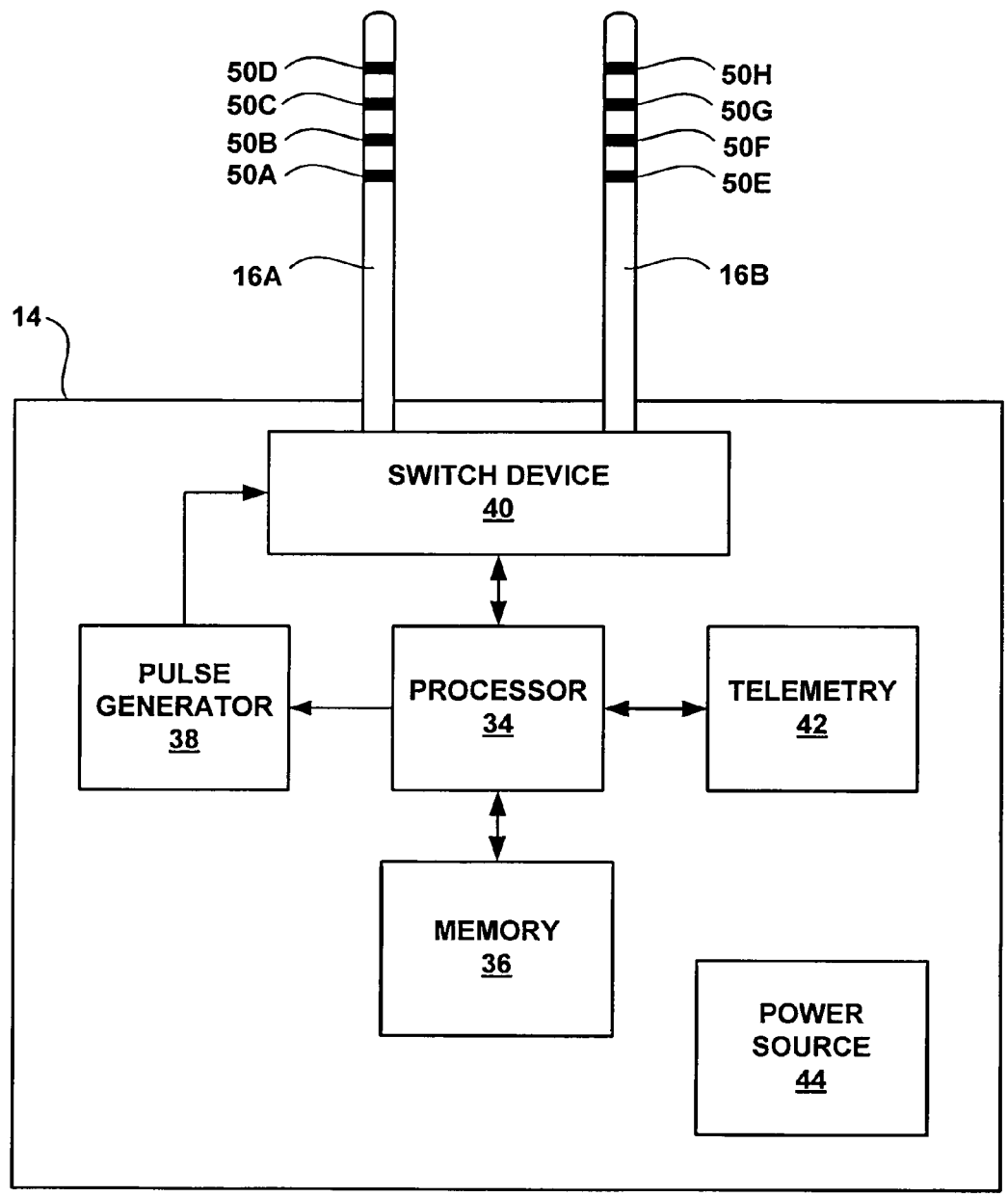
FIG. 3 is a block diagram of an implantable electrical stimulation that generates electrical stimulation and delivers the stimulation therapy based upon one or more programs.

FIG. 3 is a block diagram of an implantable electrical stimulator 14 that generates electrical stimulation and delivers the stimulation therapy based upon one or more programs. Stimulator 14 may deliver stimulation via electrodes 50A-D of lead 16A and electrodes 50E-H of lead 16B (collectively "electrodes 50"). Electrodes 50 may be ring electrodes. Alternatively, electrodes 50 may be pad electrodes arranged on a paddle lead, or have more complex electrode geometries. For example, electrodes 50 may be segmented electrodes arranged in segments or sections at different arcuate sections around the circumference of an axial or cylindrical lead. In some cases, ring electrodes, pad electrodes, partial ring electrodes, and/or segmented electrodes may be combined on a single lead. The configuration, type and number of electrodes 50 and leads 16 illustrated in FIG. 3 are merely exemplary. For bilateral or multi-lateral stimulation, multiple leads may be provided. In the example of FIG. 3, two leads 16A and 16B are shown.

In the example of FIG. 3, electrodes 50 are electrically coupled to a switch device 40. Switch device 40 is able to selectively couple each of the electrodes to circuits within stimulator 14 under the control of a processor 34. For example, through switch device 40, processor 34 may selectively couple electrodes 50 to a pulse generator 38. In other examples, switch device 40 may not be necessary if separate pulse generators 38 are provided for and coupled to each electrode 50. Additionally, some embodiments may include a plurality of pulse generators 38 selectively coupled to any of electrodes 50, which may be more numerous than the pulse generators, by one or more switch devices 40.

Pulse generator 38 may deliver electrical pulses to patient 12 via at least some of electrodes 50 under the control of a processor 34, which controls pulse generator 38 to deliver the pulses according to the stimulation parameter values of a current program. Processor 34 controls via which of electrodes 50 the pulses are delivered, as well as the polarity of the pulses at each of the selected electrodes, by its control of switch matrix 40, or its selective control of respective pulse generators in embodiments in which electrodes are associated with respective pulse generators. The programs used by processor 34 to control delivery therapy by pulse generator 38 may be received via a telemetry module 42 and/or stored in memory 36. In some examples, in addition or instead of pulse generator 38, stimulator 14 may include one or more stimulation generators that produce continuous signals, such as sine waves.

Processor 34 may include a microprocessor, a controller, a DSP, an ASIC, an FPGA, discrete logic circuitry, or the like, or any combination of one or more of the foregoing devices or circuitry. Memory 36 may include any volatile, non-volatile, magnetic, optical, or electrical media, such as RAM, ROM, NVRAM, EEPROM, flash memory, and the like. In some embodiments, memory 36 stores program instructions that, when executed by processor 34, cause stimulator 14 and processor 34 to perform the functions attributed to them herein.

Telemetry module 42 may include components to send data to and/or receive data from programmer 20. Telemetry module 42 may utilize any number of proprietary wireless communication protocols known in the medical device arts. Furthermore, telemetry module 42 may use radio frequency (RF) signals according to 802.11, Bluetooth or other short range wireless technologies. Power source 44 may be a rechargeable or non-rechargeable battery. A rechargeable battery may be recharged via inductive coupling with programmer 20 or another external device capable of recharging power source 44. Power source 44 may employ an energy scavenging device or heat device that uses patient 12 motion or generated heat to recharge the rechargeable battery. Alternatively, power source 44 may also require inductive coupling to an outside energy source at any time that stimulator 14 is to operate, i.e., may store inadequate power for non-coupled operation of stimulator 14.

FIGS. 4-29 are conceptual illustrations of user interfaces that facilitate user programming of electrical stimulation therapy. The user interfaces may be presented via a display and other input or output media associated with programmer 20. Field shapes are icons that may be used by the clinician to specify what the resulting stimulation field should look like for patient 12. Field shapes may refer to different aspects of the stimulation field, depending on the preference of the clinician. For example, the field shapes may be representative of a current density, an activation/inhibition function, and/or a neuron model. The current density field shape illustrates how the electrical current from the electrical field produced by electrodes 50 propagates or is expected to propagate through the tissue of patient 12 around leads 16. The activation function field shape illustrates which portion of the tissue will be activated and/or inhibited by the electrical field around electrodes 50. Activation is generally caused around the cathode (electrons leaving that particular electrode designated as the cathode) and inhibition is generally caused around the anode (electrodes reaching that particular electrode designated as the anode). In addition, the field shapes may illustrate a neuron model, or how neurons within stimulated tissue would actually be affected by the stimulation therapy. The field shapes, and resulting stimulation field, may be adjusted to illustrate any aspect of the stimulation therapy that would provide insight to the clinician for programming the stimulation therapy.

Figure 4:
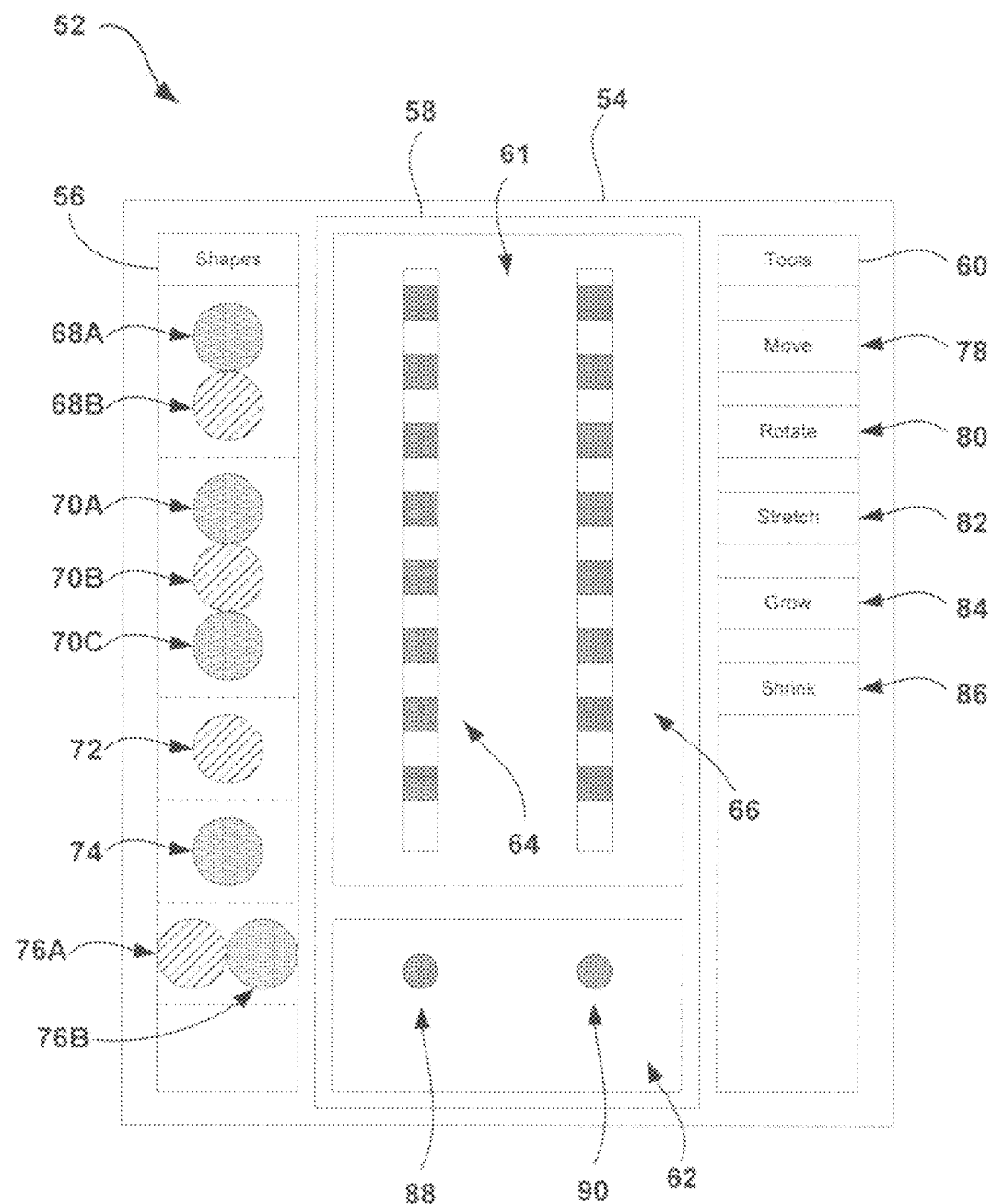
FIG. 4 is a conceptual illustration of a user interface that facilitates programming of electrical stimulation therapy.

FIG. 4 shows a graphical user interface (GUI) 52 that includes a side view 61 and axial cross-section, i.e., a depth view 62, of two implantable leads in a stimulation region 58. Lead side view 64, lead side view 66, lead axial section 88, and lead axial section 90 may be representative of leads 16 described in FIGS. 1 and 3. GUI 52 is provided in screen 54 and contains field shape selection menu 56 and field manipulation tool menu 60 located on either side of GUI 52.

Field shape selection menu 56, e.g., "Shapes" located on the left provides example field shapes that the clinician may select and drag over to a location within stimulation region 58 proximate to the lead representations, e.g., proximate to lead side views 64 and 66. In the illustrated example, field shape selection menu 56 comprises five selectable "groups" of one or more field shapes, including, for example, field shapes 68A and 68B, which are collectively form and are referred to as a "field shape group 68." Each of field shapes groups 68, 70, 72, 74, and 76 are illustrative of an activation function. In various embodiments, field shape selection menu 56 may include any number of selectable field shape groups.

Striped field shapes may indicate activation of the tissue while shaded field shapes may indicate inhibition of the tissue. Activation of tissue generally refers to the initiation of action potentials within nerve tissues. Activation of tissue may occur near electrodes 50 configured as cathodes. Conversely, inhibition of tissue generally refers to the prevention of activating action potentials within adjacent nerve tissues. Inhibition of tissue may occur near electrodes 50 configured as anodes. Activation and inhibition of tissue is thereby generated in part by the location of anodes and cathodes implanted within patient 12.

However, these particular visual pattern choices (striped and shaded) are for purposes if illustration and example, and should not be considered limiting. In other embodiments, for example, different colors may indicated activation and inhibition, e.g., red field shapes may indicate activation of tissue and blue shapes may indicate inhibition. Activation, inhibition, or locations or states in between activation and inhibition, may be indicated by any color, shading, symbol, or indication. In addition, field shapes may be of any specific shape, e.g., circular, oval, square, or rectangular, that corresponds to electrodes 50, the type of therapy, or other factors. In the example of FIG. 4, field shape groups 68, 70, 72, 74, and 76 comprise circular field shapes.

Multiple field shapes may be shown in the shapes toolbar to provide flexibility to the clinician. As shown, five different field shape groups 68, 70, 72, 74, and 76 are provided to the clinician. Combinations of field shapes shown to the clinician may include activation and inhibition pairs (field shape groups 68 and 76), single activation field shapes (field shape group 72), single inhibition field shapes (field shape group 74), and multiple activation and inhibition groups (field shape group 70), where any of the field shapes may be oriented in different directions. Field shape group 68 comprises a vertically oriented activation/inhibition pair, field shape group 70 comprises two inhibition field shapes and one activation field shape between them, field shape group 72 comprises a single activation field shape, field shape group 74 comprises a single inhibition field shape, and field shape group 76 comprises a horizontally oriented activation/inhibition pair. The clinician may interface with GUI 52 to click a desired field shape group and drag it to a position within stimulation region 58. The position of each field shape may correspond with a direct location of one of electrodes, or the position of each field shape may be offset from one or more electrodes of lead side views 64 and 66. As an example, field shape 70 may be dragged over lead side view 64 in stimulation region 58 such that each field shape 70A, 70B, and 70C covers one of an adjacent vertical trio of electrodes of lead side view 64. In other examples in which a field shape does not directly correlate with the center of an electrode, i.e., it is offset from center, simultaneous activation of two or more electrodes at two or more different current or voltage amplitudes may be used to effectively center the actual stimulation field in the desired location as shown by the field shape. Processor 22 determines the stimulation parameters that will result in the actual stimulation field based upon the placement of the field shapes. If a placement of a field shape is not achievable given a lead geometry and/or pulse generator 38 capability, processor 22 may notify the user of this error and/or automatically adjust the field shape to the nearest achievable location within stimulation region 58.

Field shape manipulation tool menu 60 is located on GUI 52 as well, e.g., right of stimulation region 58. Field shape manipulation tool menu 60 provides icons that allow the clinician to manipulate and adjust any of the field shapes placed within stimulation region 58. Field shape manipulation tool menu 60 may include icons such as move icon 78, rotate icon 80, stretch icon 82, grow icon 84, and shrink icon 86. The clinician may select one or more field shape groups from field shape selection menu 56 and select an action from field shape manipulation tool menu 60 that accordingly changes one or more of the field shapes placed within stimulation field 58. Alternatively, each action from field shape manipulation tool menu 60 may be selectively applied to all field shapes within stimulation region 58 that define the stimulation field for therapy.

As an illustration, an field shape group 68 may be selected from field shape selection menu 56, dragged into stimulation region 58, and placed over a desired pair of electrodes of lead side view 64, e.g., using a stylus or other pointing tool. Then, the user may select the grow icon 84 from the field shape manipulation tool menu 60 to increase the size of one or both of field shapes 68A and 68B in stimulation region 58 to a desired size for the represented activation and/or inhibition regions. For example, selection of grow icon 84 may reveal a command structure that permits the user to enter a size, drag a perimeter of one or both of field shapes 68A and 68B to increase their size, select an arrow in the direction of the growth of the field shape, or select an incremental input, like a plus or up arrow to incrementally increase the size according to a proportional or preselected fixed magnitude. Alternatively, growing or shrinking of a field shape may be realized by up/down arrows, plus/minus icons, or a slider bar to increase and decrease the size of the field shapes. If multiple sets of field shapes are presented in stimulation region 58, the user may be required to select one of them, e.g., with a stylus, in order to apply to the appropriate tool from the field shape manipulation tool menu 60 to manipulate a field shape or selected set of field shapes or field shape groups. In some examples, more or less icons may be available to the clinician to perform certain actions. For example, depending on the placement of selected field shapes, processor 22 may remove or inactivate one or more icons of field shape manipulation tool menu 60 because that action cannot be performed.

In addition to the actions shown in field shape manipulation tool menu 60 of GUI 52, other icons may be presented that allow the clinician to perform different actions. For example a mirror icon may be provided that allows the clinician to select a field shape or field shape group and flip it about a vertical axis, horizontal axis, or oblique axis. The clinician may also be able to create new actions for use with GUI 52, save them to an action library, and load them into the field shape manipulation tool menu 60 when desired. Field shape manipulation tool menu 60 may also have a copy and paste action that allows the clinician to duplicate field shapes or field shape groups within stimulation region 58 and place it at another location. In other examples, GUI 52 may allow the clinician to delete one or more field shapes in stimulation region 58. For example, the clinician may simply drag the unwanted field shape or field shape group off of stimulation region 58 to make it disappear, or GUI 58 may include a trash can or other area that the clinician drags the field shape or group into to delete it from the stimulation region.

In other examples, the clinician may be able to adjust the field shape prior to placing the field shape within stimulation region 58. In this manner, the clinician may select an icon within manipulation tool menu 60 that sets a default field shape size or position that is placed within stimulation region 58. In addition some icons of manipulation tool menu 60 may be deactivated until a field shape is placed within stimulation region 58. For example, GUI 52 may only provide grow icon 82 after a field shape is selected and placed within stimulation region 58.

GUI 52 may also include options that allow the clinician to change the layout of stimulation region 58, field shape selection menu 56, or field shape manipulation tool menu 60. For example, the clinician may want both menu 56 and menu 60, e.g., any toolbars, on one side of stimulation region 58. Alternatively, the clinician may be able to zoom into or out of stimulation region 58 to get a closer view of one or more field shapes in relation to lead side views 64 and 66. GUI 52 may also allow the clinician to view, in conjunction with the stimulation field shapes, a scale of stimulation region 58, markers indicating anatomical areas of patient 12, an anatomical region of patient 12, e.g., a tissue image, an anatomical atlas, a somatotopic map, or any other indication to the clinician that may be useful for visualizing the effect of stimulation fields while programming stimulation therapy.

In addition to side view region 61, stimulation region 58 may include depth view region 62 that includes lead axial views 88 and 90. Stimulation depth view region 62 may orient the clinician to the radial magnitude of field shapes that cannot be shown by side view region 61 of stimulation region 58. Accordingly, stimulation depth view region 62 may be an end view looking down the length of a lead, such that the effect of the stimulation field lateral to the lead can be readily observed in terms of depth of penetration into surrounding tissue. In other words, the clinician may be able to view an axial cross-section representation of leads 16. This depth view may be especially important in the case of leads with segmented or asymmetric electrode profiles such that stimulation is not symmetric about the longitudinal axis of lead 16.

A marker may be shown in side view region 61 that indicates the longitudinal position of lead side views 64 and 66 that the stimulation depth view region 62 is illustrating. In some examples, processor 22 will automatically determine the longitudinal location for stimulation depth view region 62, e.g., at the location of the greatest radial magnitude of the stimulation field. Alternatively, the clinician may select the longitudinal location of stimulation depth view region 62 and move along the length of lead side views 64 and 66 to view other depths of the represented leads. This may be represented by a line or plane in side view region 61. In some examples, GUI 52 may represent depth of the field shapes, i.e., the extent to which the field extends outward transversely relative to a longitudinal axis of the lead side views 64 and 66, without the use of stimulation depth region 62. For examples, a contour view, a view where color intensity correlates to depth, or a view where deeper stimulation is more opaque than shallower stimulation may be used to represent depth of the stimulation. In other cases, the locations of side view region 61 and depth view region 62 in stimulation region 58 may be switched to allow stimulation depth view region 62 to be the primary area where the clinician places field shapes.

In some examples, the types of fields being shown to the clinician may be different between side view region 61 and depth view region 62. For example, activation/inhibition functions may be shown in side view region 61 while current density may be shown in depth view region 62. GUI 52 may automatically determine the field type shown to the clinician, or the clinician may select the field types to be shown. The clinician may select these types directly from GUI 52 or within a menu that the clinician may open.

GUI 52 as illustrated in FIG. 4 and described throughout this specification, generally may be realized by any combination of display technology and selection media. Examples include display screens and various combinations of hard keys, soft keys, buttons, touchscreen media, and the like, as well as any of a variety of pointing devices such as a stylus, mouse, trackball, scroll wheel, joystick, or the like. In some examples, a touchscreen and stylus may be particularly useful in selecting and manipulating features of GUI 52. Also, in some examples, programmer 20 may include various buttons and a keypad such as an alphanumeric keypad. The foregoing structure is described for purposes of illustration and without limitation to GUI 52 implementation.

Figure 5A:
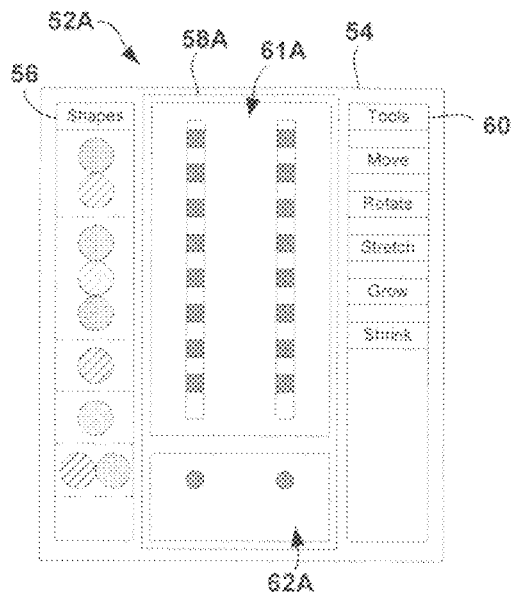
FIGS. 5A-5D are conceptual illustrations of user interfaces that include different stimulation regions for placing stimulation fields.

FIGS. 5A-5D show example GUIs 52A-52D illustrating different configurations for stimulation region 58 along with field shape selection menu 56 and field manipulation tool menu 60. Similar to GUI 52 of FIG. 4, GUIs 52A-52D include one of stimulation regions 58A, 58B, 58C, and 58D (collectively "stimulation regions 58") that allow the user to define the stimulation field with field shapes from field shape selection menu 56. FIG. 5A shows GUI 52A that includes stimulation field 58A with lead side view region 61A similar to lead side view region 61 of FIG. 4, and a lead depth view region 62A similar to lead depth view region 62 of FIG. 4.

Figure 5B:
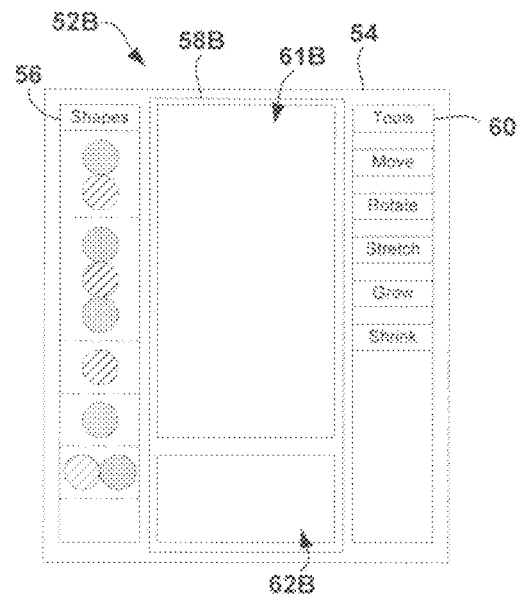

FIG. 5B displays GUI 52B which includes stimulation region 58B, including side view and depth view regions 61B and 62B. Stimulation region 58B does not include representations of the leads implanted within patient 12. Instead, the clinician attempts to place field shapes at desired locations of tissue within patient 12. Using GUI 52B, one or more markers of tissue location may be provided to orient the clinician.

Figure 5C:
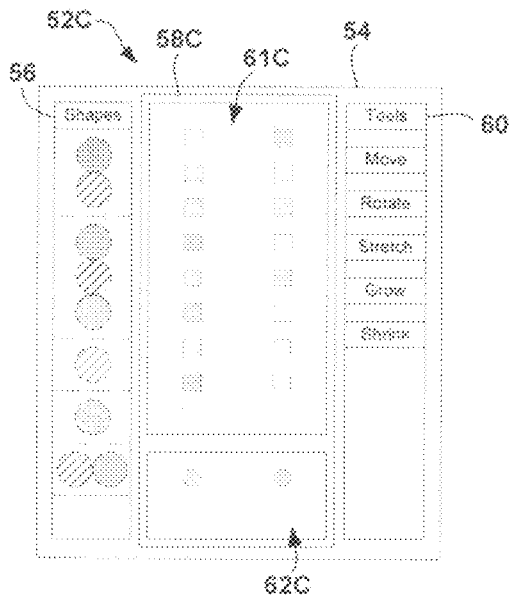

FIG. 5C illustrates GUI 52C, which shows representations of leads 16 in the stimulation region 58C (side view and depth view regions 61C and 62C), but the leads are faded and shown in the background to emphasize the importance of the location of the field shape relative to patient tissue when programming with field shapes from field shape selection menu 56.

Figure 5D:
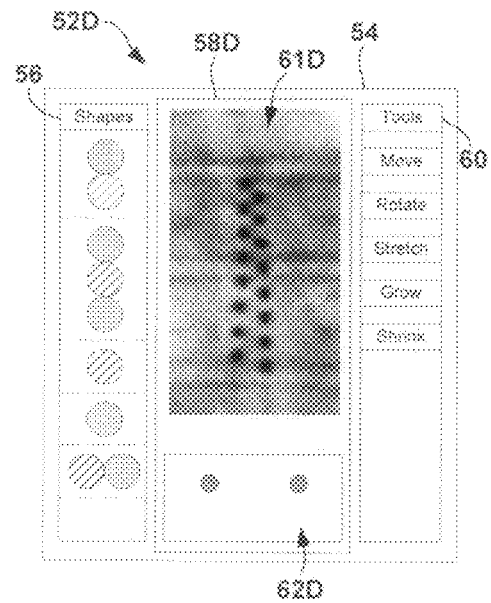

In an alternative example, FIG. 52D shows GUI 52D including an actual image of an anatomical region of patient 12 within side view region 61D. The image of side view region 61D may illustrate electrodes of implanted leads 16. The image may be a fluoroscopic image, x-ray image, MRI image, or any other image of the patient in the pertinent region for stimulation. The image may provide an anatomical reference to facilitate placement of field shapes from field shape selection menu 56 at a desired anatomical location by the clinician. In the example of FIG. 5D, side view region 61D includes the actual image, while depth view region 62D does not. In various embodiments, either or both of the sub regions within stimulation region 58D may include an actual image of leads 16 and/or the anatomy of patient 12.

In any of GUIs 52A-52D shown in FIGS. 5A-5D, a representation of the anatomy of patient 12 may be provided in the respective stimulation region 58 to orient the clinician. The anatomical representation may be an image of the actual anatomy of patient 12 and the relation of implanted leads 16 to the represented anatomical region. In this manner, the clinician may be able to accurately place field shapes over the particular anatomical region that the clinician desires to stimulate. For example, the clinician may specify which tissue should be activated and inhibited with the activation/inhibition function type of field shapes. The anatomical region may be an image created by any imaging modality available to the clinician. For example, the anatomical region may be acquired through the use of a magnetic resonance imaging (MRI) device, an X-ray device, a computed tomography (CT) device, a positron emission tomography (PET) device, or any other suitable imaging modality. Alternatively, the anatomical region may be a representative region that is not obtained from the actual patient, for example a schematic image or a standard reference image from an available atlas of images.

Programmer 20 may map or configure the stimulation region 58 based on the location of leads 16 and electrodes 50 within patient 12. The clinician either manually enters the coordinates of leads 16 and/or electrodes 50 into programmer 20 to create stimulation region 58, or the coordinates are automatically mapped via an imaging modality. While the clinician may use stimulation region 58 without mapping the location of leads 16 to the stimulation region, the generated stimulation parameters for the stimulation field created by the clinician may be inaccurate and ineffective in treating patient 12.

Figure 6:
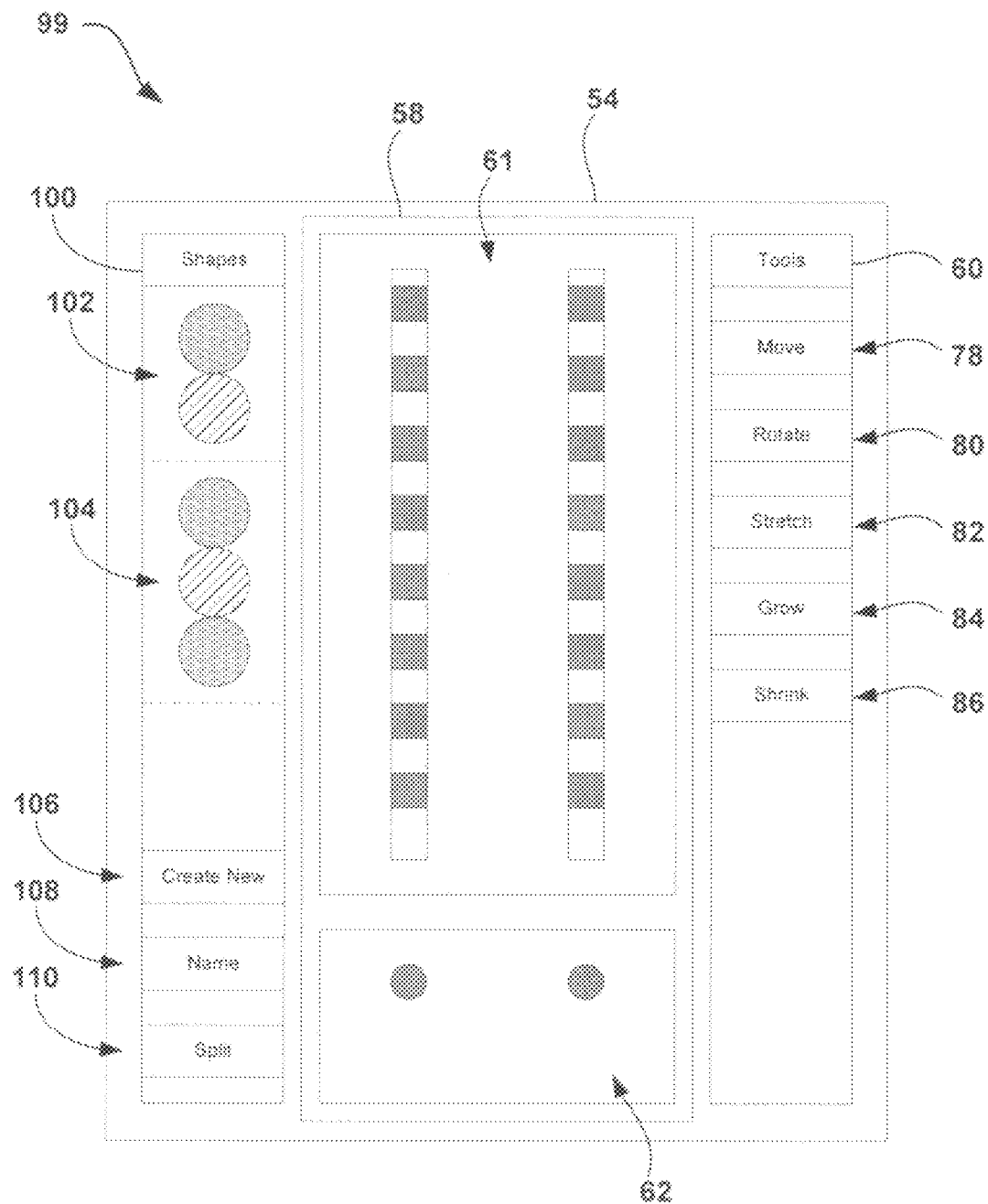
FIG. 6 is a conceptual illustration of a user interface with a toolbar that allows a user to create shape icons.

FIG. 6 is another example GUI 99 for programming stimulation therapy with field shapes from field shape selection menu 100. GUI 99 is similar to GUI 52 of FIG. 4, and provides stimulation region 58 with side and depth view regions 61 and 62 including representations of leads 16, along with field shape selection menu 100 and field shape manipulation tool menu 60. Field shape selection menu 100 may include field shape groups 102 and 104. In addition to available field shapes in field shape selection menu 100, managing icons are provided to offer customization of field shapes to the clinician. Managing options may include create new icon 106, name icon 108, and split icon 110.

Split icon 110 may be used to divide a selected field shape group (e.g., selected with a stylus or other pointing device) into two groups, each containing one or more field shapes. For example, field shape group 102 may be split into two identical field shape groups. In some examples, a merge icon (not shown) may be provided to combine two or more field shapes or field shape groups into a single field shape group containing multiple field shapes. The clinician may select create new icon 106 when the clinician desires to create a new field shape or group that is not present in field shape selection menu 100.

The clinician may attach a name to a certain field shape or field shape group by selecting the name icon 108. Field shapes or field shape groups separated by the split function may define multiple stimulation fields delivered to tissue of patient 12 using interleaved pulse trains (e.g., sets of stimulation pulses) from one stimulus generator or multiple simultaneous pulses or signals from multiple stimulus generators. Therefore, splitting a field shape may involve breaking one pulse train or signal into two or more interleaved pulse trains or signals, respectively. Merging two or more field shapes may cause the electrode combinations being delivered in multiple pulse trains or signals to change into an equivalent (or near equivalent) single field shape or field shape combination to be delivered in a single pulse train.

In addition, GUI 99 may allow the clinician to save newly created field shapes, field shape groups, combinations, or entire stimulation fields as positioned in stimulation region 58. In this manner, the clinician may be able to store multiple preset field shapes, field shape groups, or stimulation fields in programmer 20 so that the clinician does not need to start from scratch with each session for patient 12 or other patients. The saved field shapes may be field shapes or field shape groups that, from experience, the clinician knows generally provide efficacious therapy to patient 12. In other examples, GUI 99 may have a library icon (not shown) that the clinician may select to browse saved field shapes and field shape groups, and move selected library items into field shape selection menu 100. A library may be common to multiple patients, or preserved specifically for a single patient 12, or common to a specific lead or device family. Field shapes may be named by the clinician or assigned names automatically by programmer 20. Names may be descriptive of a particular field shape and may be edited by the user.

Generally, the field shapes available to the clinician via field shape selection menu 100 are used by the clinician as a starting point for programming the stimulation therapy for patient 12. In other words, the field shapes may not initially be tailored for certain therapy profiles or anatomy positions. The clinician drags one or more field shapes, e.g., field shape group 104, into stimulation region 58 and proceeds to modify those field shapes with actions indicated by selection of icons from field shape manipulation tool menu 60 in order to create a stimulation field for the defines the desired therapy. In this manner, the clinician may be able to create customized therapy for patient 12 with a reduction in time as compared with conventional selection of individual stimulation parameters, e.g., electrode configuration, pulse width, pulse rate, current amplitude, and voltage amplitude.

In some examples, field shapes of field shape selection menu 100 may initially be associated with a set of stimulation parameters, e.g., program, that would produce each particular field shape. These programs may include an electrode configuration (anodes and cathodes), pulse width, pulse rate, and voltage and/or current amplitude. However, as the clinician changes the location and size of the field shapes in stimulation region 58, the initial set of stimulation parameters changes as needed to reproduce the stimulation field representation created by the clinician. In particular, programmer 20 may automatically adjust the stimulation parameters to produce, at least approximately, the stimulation field representation created by the clinician.

Figure 7A:
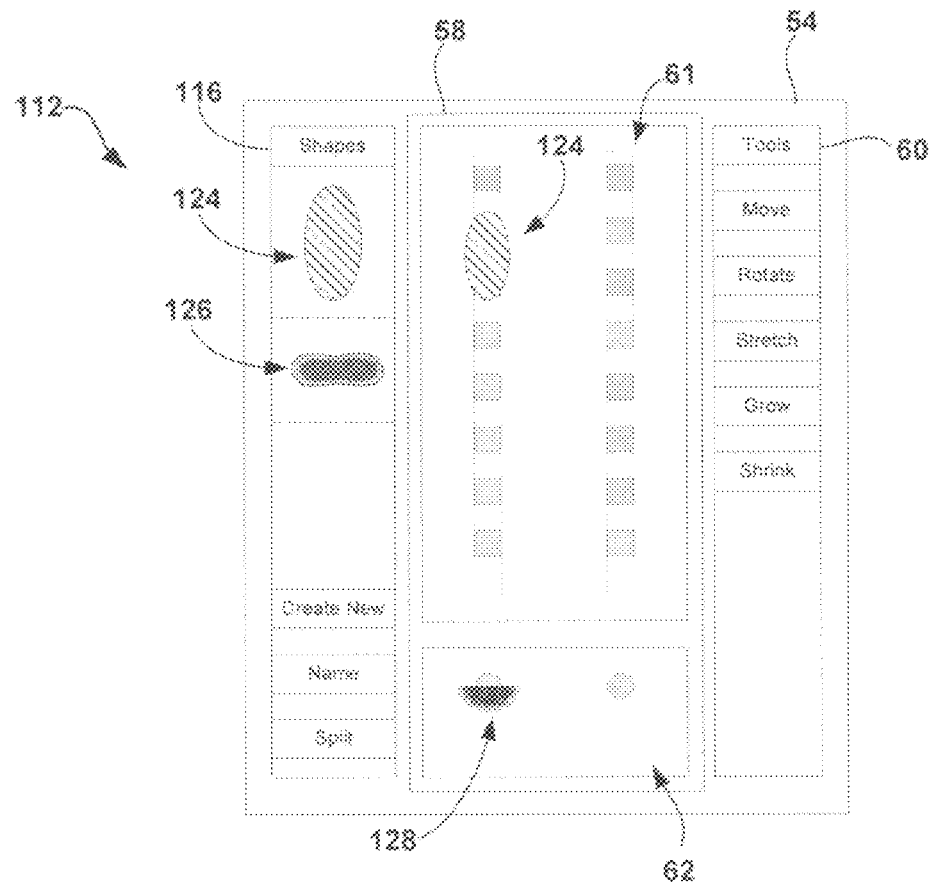
FIGS. 7A and 7B are conceptual illustrations of a user interface with activation and current density icons and a view of delivered current density to a patient.
Figure 7B:
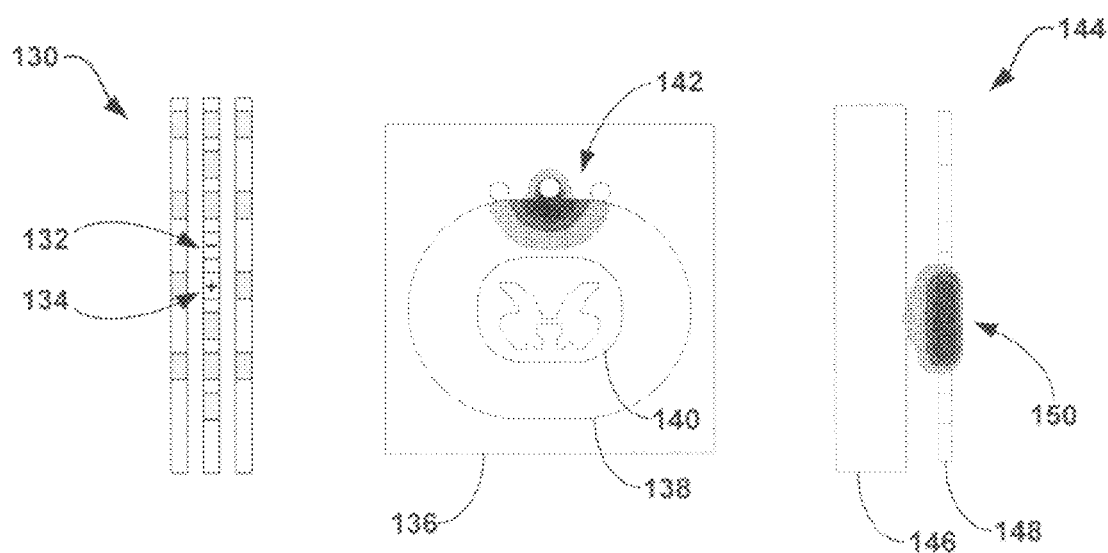

FIGS. 7A and 7B show field shapes illustrating current density of the proposed/delivered stimulation. Like GUI 52 of FIG. 4, GUI 112 illustrated in FIG. 7A includes stimulation region 58, including side and depth view regions 61 and 62, as well as field shape manipulation tool menu 60, and a field shape selection menu 116. Field shape selection menu 116 includes field shape 124 which displays an idealized current density and field shape 126 which displays an actual current density field. In the example of FIG. 7A, field shape 124 is representative of the shape of the current density field idealized into a simple oval field shape and is provided in stimulation region 118. The actual current density field shape 126 is a model of what the actual current density of that field shape will be within patient 12. As shown, field shape 126 is a current density model based upon either a general tissue characteristic, a typical spinal cord, a homogenous medium, a general anatomical model, or the actual tissue characteristics derived from an image of the anatomy of patient 12. Field shapes may be predefined and stored on programmer 20 or generated in real time as the clinician selects the field shapes. Field shape 126 shows that greater current density is located near and in between two electrodes producing the field shape.

Stimulation depth view region 62 displays the field depth 128 which is the actual current density of field shape 124 placed by the clinician over one of the leads in side view region 61. As shown, the current density reduces with greater radial distance from active electrodes. Processor 22 may automatically determine the axial location along the leads shown in stimulation depth view region 62 to show in the maximum depth of the current density. This axial location of field depth 128 may correspond to the greatest depth of the field model. GUI 112 may show a marker, dotted line, or some other indication in stimulation side view region 61 that indicates to the clinician the axial location shown in stimulation depth view region 62. Alternatively, GUI 112 may allow the clinician to set the axial location of stimulation depth view region 62 to identify depths of the stimulation field at various axial locations of stimulation side view region 61. In addition to, or instead of, the transverse stimulation depth view region 62, a depth view may be provided that is longitudinal or axial in nature, e.g., oriented along the longitudinal axis of the leads. An associated marker line showing the plane of cross section in stimulation side view region 61 may be used to indicate the location within the alternative longitudinal depth view.

Example modeled current densities are illustrated in the model views 136 and 144 of FIG. 7B. Leads 130 are provided with example cathode 132 and anode 134 to correspond to field shape 124 of FIG. 7A. With an electrode located next to the spinal cord, the current density is greatest near the lead and decreases with radial distance away from the lead (or further within the spinal cord) as shown in a model views 136 and 144. Model view 136 shows subarachnoid space 138 and spinal cord 140 in relation to current density model 142. Greater current density is shown by darker shading with decreasing current density indicated by lighter shading as the current propagates away from the electrodes. Alternatively, greater current density may be shown by a "hotter" color, such as red, with decreasing current density indicated by progressively "cooler" colors from red to blue. For example, the current density range may run from red, to orange, to yellow, to green, and to blue to indicate the range of current density from highest to lowest.

Model view 144 includes spinal cord 146 with leads 148 placed longitudinally along the spinal cord. Current density model 150 is also shown to indicate the generally oval shape of the current density model corresponding to the current density from two active electrodes of leads 148. It should be noted that the actual current density is not perfectly oval, but is more "peanut" shaped with a drop off in current density between the two electrodes. While the current density is uniform at both electrodes, the effect on the adjacent tissue varies due to whether the tissue is closer to the anode or cathode of the active electrodes. This difference may be similar to the activation of tissue and inhibition of tissue as described above. The "peanut" shape is one example of a field shape, and other non-regular field shapes may be yielded by other stimulation parameter values.

Figure 8A:
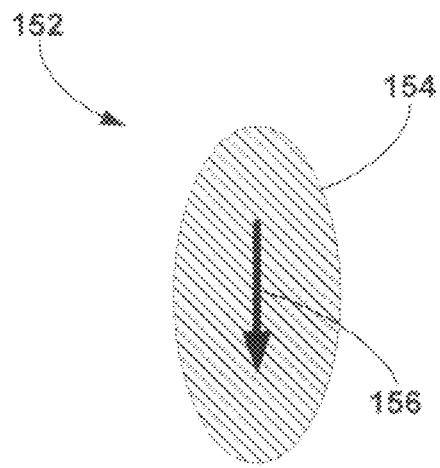
FIGS. 8A and 8B are example activation and current density icons with direction indicators.
Figure 8B:
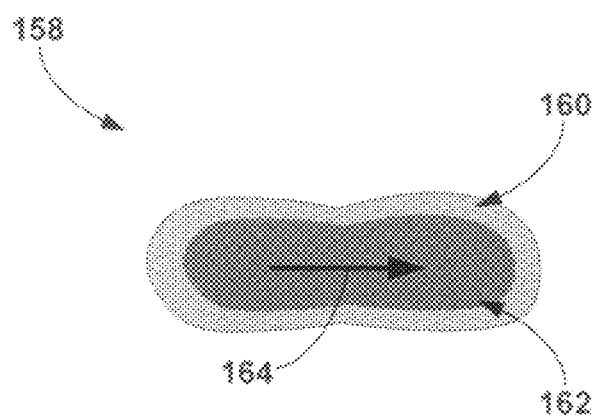

FIGS. 8A and 8B provide an illustration for alternative current density field shapes 152 and 158 that may be provided by a user interface, i.e., within a field shape selection menu of such user interface, according to the invention. Field shape 152 of FIG. 8A is an idealized current density field shape 154 with vector indication 156. Vector indication 156 is an arrow that represents the direction current flows, from the anode to the cathode. Vector indication 156 indicates the average or net current direction. In other embodiments, many discrete vectors may be shown to indicate current direction and magnitude in many points at once. This vector field representation may be advantageous in assisting the clinician in visualizing the outcome of a set of stimulation parameters. FIG. 8B shows field shape 158 which is an actual current density field shape 160 that shows modeled current density, e.g., representing higher to lower current density as progressively lighter shading or changing color from red to blue, for example. Vector indication 164 is an arrow that represents the direction that current flows, which is from the anode to the cathode. In these cases, both field shapes 152 and 158 may be used to define a stimulation field in any stimulation region described herein and present the direction and magnitude of the stimulation provided by a selected electrode configuration.

With either of vector indications 156 or 164 on the field shapes 152 or 158, respectively, the clinician may visualize the electrical context of a selected field shape. This may be particularly useful when, for example, the clinician selects that the field shape be rotated in the stimulation region of the GUI. In addition, the vector indications 156 or 164 may have an impact on the clinician's decision to select another, or which other, field shape for the stimulation region. In other examples, field shapes indicating the vector of the electrical current may have an indication other than an arrow. For example, the vector indication may be shown as plus and minus signs, a triangle, progressively bigger dots in a line, a shaded line, or any other representation.

Current density field shapes may be particularly beneficial to DBS applications. Within the brain, the clinician may desire to limit current density, or charge density, at specific locations within the brain. The clinician may set a limit to the current density in which field shapes do not go beyond a preset current density limit or the clinician may simply view the current density applied to patient 12 via a color of the field shape or a numerical indicator over the field shape. Of course, current density field shapes may also be used for therapy applications other than DBS.

Figure 9A:
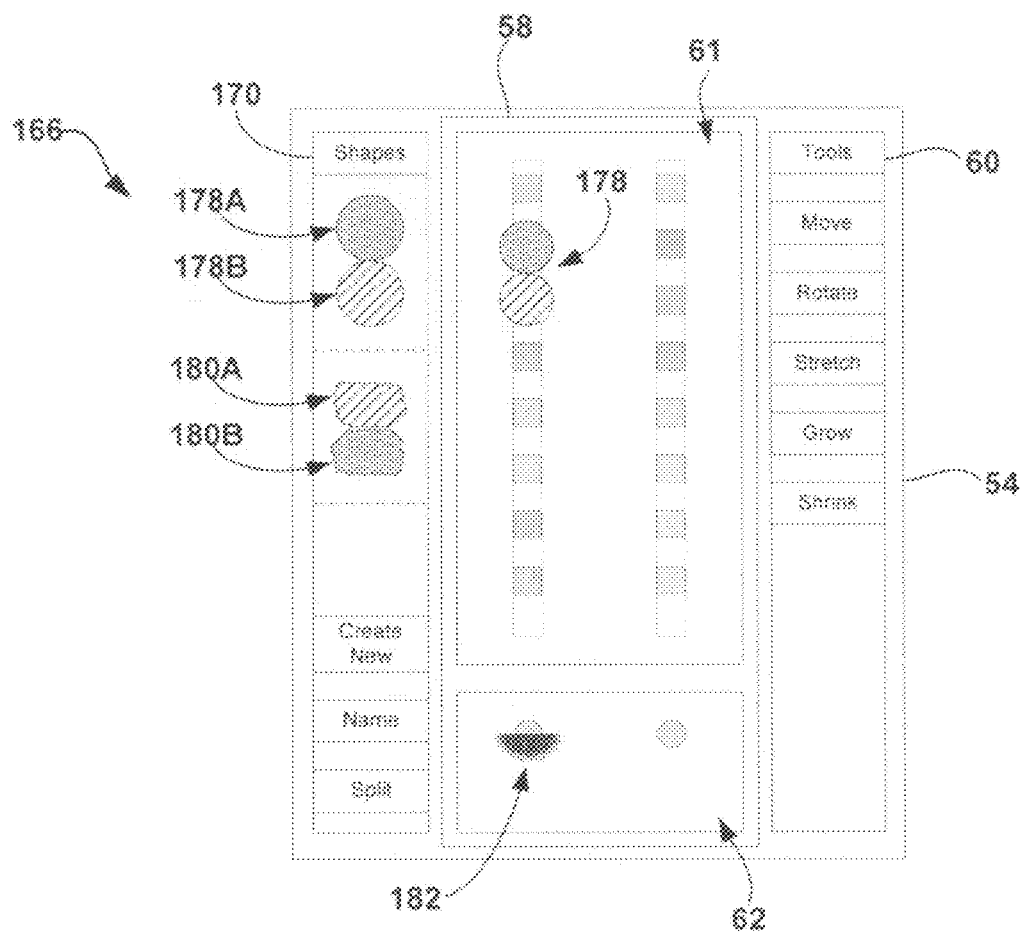
FIGS. 9A and 9B are conceptual illustrations of a user interface with activation and neuron model icons and a view of neuron activation.
Figure 9B:
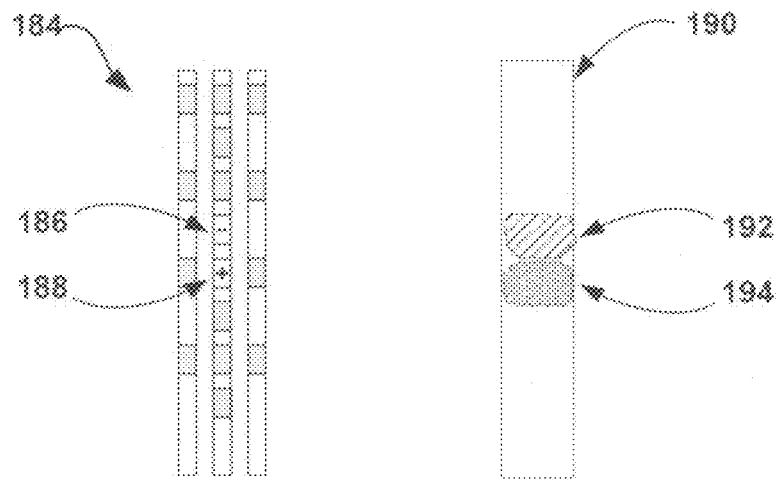

FIGS. 9A and 9B illustrate a GUI 166 with idealized activation function ("act func") field shapes 178A and 178B (collectively "field shape group 178") and actual activation function field shapes 180A and 180B (collectively "field shape group 180"). GUI 166 is similar to GUI 52, and includes field shape selection menu 170, field shape manipulation tool menu 60, and stimulation region 58 (including side and depth view regions 60 and 61). The clinician may click and drag any of field shape groups 178 or 180 from field shape selection menu 170 into stimulation region 58 to create a stimulation field. As shown, field shape group 178 has been placed within stimulation region 58 and, more particularly, side view region 61. In addition to side view region 61, depth view region 62 is also provided to illustrate to the clinician the actual depth of tissue of patient 12 that would be affected by the activation function from field shape group 178, e.g., as shown by the current density representation 182. However, field depth may also be shown as an idealized or actual activation function. As shown in previous examples, GUI 166 also includes field shape manipulation tool menu 60 for altering any field shapes placed in stimulation region 58.

The actual activation function field shapes, e.g., field shapes 180A and 180B, are generated by modeling the activation of tissue from electrical stimulation. In particular, the activation shown in FIG. 9B are due to an anode 188 and a cathode 186 of leads 184. Corresponding actual activation functions are shown with respect to spinal cord 190. Field shape 192 indicates activation of tissue while field shape 194 indicates inhibition of tissue. The electromagnetic function for neuron activation may be related to $dV^2/dZ^2$. In other examples, the activation function may be attributed to other equations that closely model the activation tissue from the electrical stimulation. In the example described herein, the activation of tissue may be indicated by stripes, whereas the inhibition of tissue may be indicated by dots. Therefore, the clinician may desire to place dotted field shape 194 in the area of tissue that the clinician does not want activated. In other words, the clinician may "shield" certain tissue from stimulation and activation of that nerve tissue. This may permit direct specification of "shielded" areas.

Figure 10A:
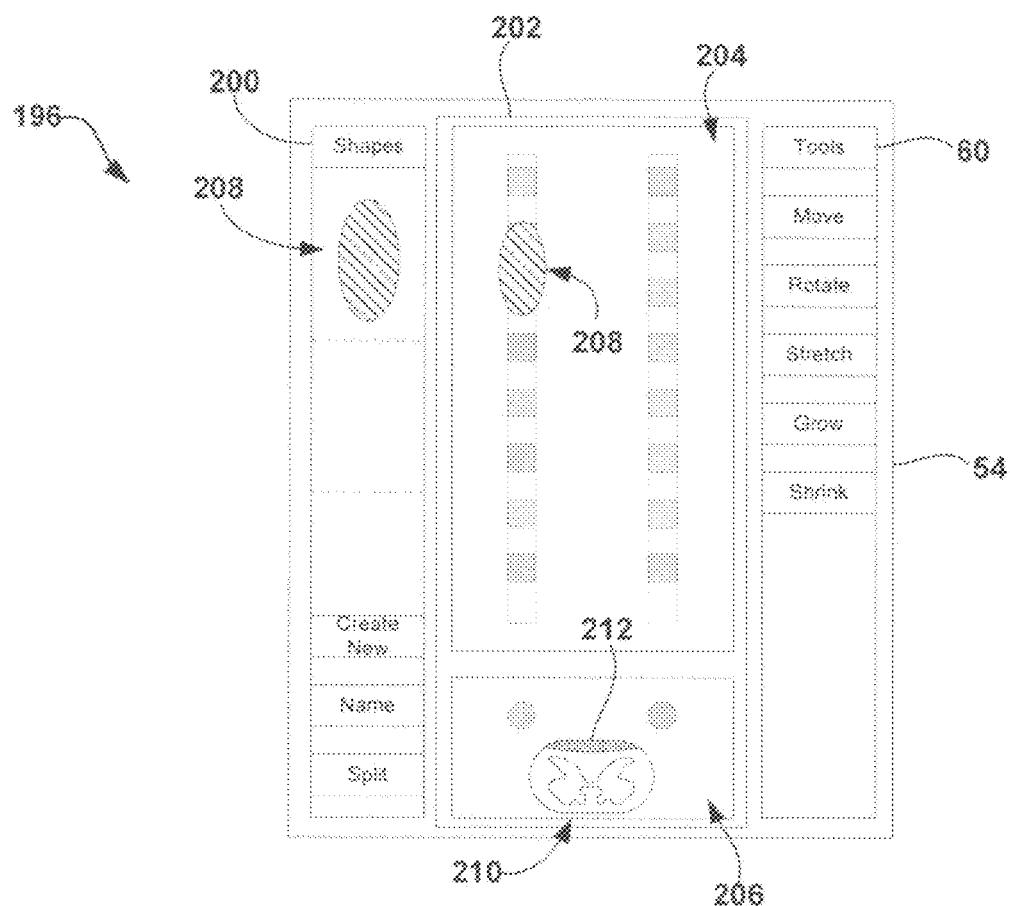
FIGS. 10A and 10B are conceptual illustrations of a user interface with an activation icon and a view of stimulation depth region activation.

FIG. 10A shows example GUI 196 including a field shape selection menu 200 that includes an idealized neuron activation field shape 208. GUI 196 may be similar to GUI 52, and GUI 196 also includes field shape manipulation tool menu 60, and a stimulation region 202 comprising a side view region 204 and a depth view region 206. The neuron activation field shape 208 is also shown to be placed over one of the lead side views in side view region 204 according to the desires of the clinician. Corresponding with the view of side view region 204 and neuron activation field shape 208, stimulation depth view region 206 provides further information for the clinician. In particular, stimulation depth view region 206 provides an axial cross section of both leads in conjunction with a cross-section of the adjacent spinal cord 210. The cross-section of spinal cord 210 may be shown with white matter indicated by white portions and gray matter indicated by gray areas. The neuron activation effect on the spinal cord is indicated by neuron activation model 212. Neuron activation model 212 of spinal cord 210 indicates to the clinician that only a portion of neurons in the white matter is affected by the stimulation, whereas neurons in the gray matter are left unaffected.

Figure 10B:
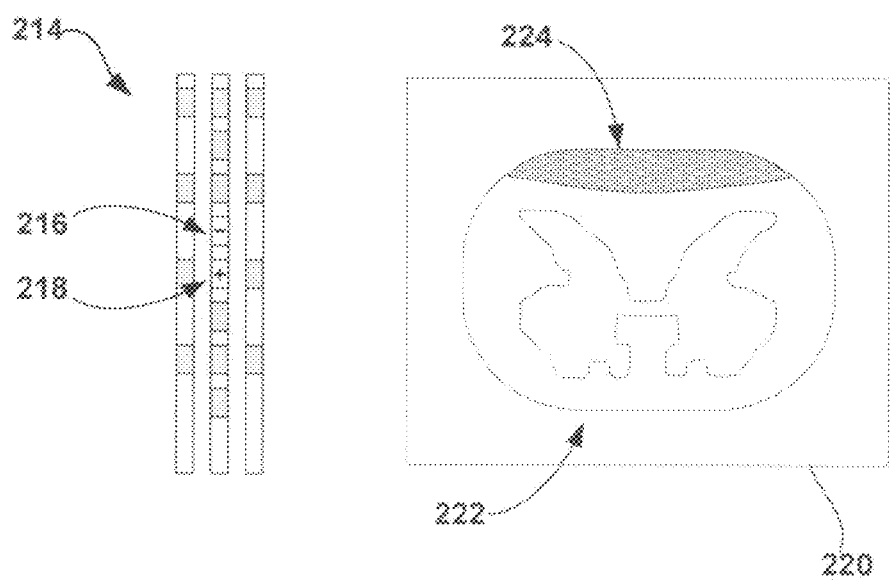

The neuron activation field shape 208 or similar field shapes may be idealized, as shown in FIG. 10A, or the neuron activation field shape may be an actual neuron activation that is modeled for patient 12. FIG. 10B shows leads 214 which have cathode 216 and anode 218 to create the field shape 208 and neuron activation model 212 of FIG. 10A. FIG. 10B also shows a large activation model 220 that includes spinal cord 222 and neuron activation model 224 over a portion of the spinal cord. The modeling may be a finite element model and completed in real-time with programmer 20 or prior to use of the programmer. Either type of idealized neuron activation field shape 208 or an actual neuron activation field shape similar to neuron activation model 212 or 224 may be provided to the clinician via field shape selection menu 200 of GUI 196. The clinician may load particular field shapes that the clinician desires to use in stimulation region 202 using programmer 20. Alternatively, the clinician may switch between different types of field shapes by selecting a switch icon (not shown) or some other icon in field shape selection menu 200.

Figure 11A:
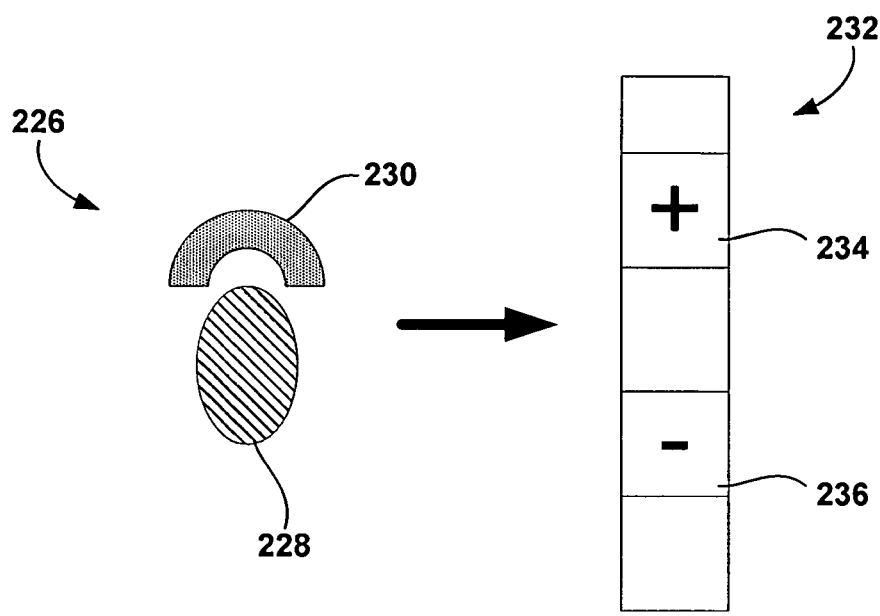
FIGS. 11A and 11B are conceptual illustrations of activation and inhibition icons for electrode polarity.
Figure 11B:
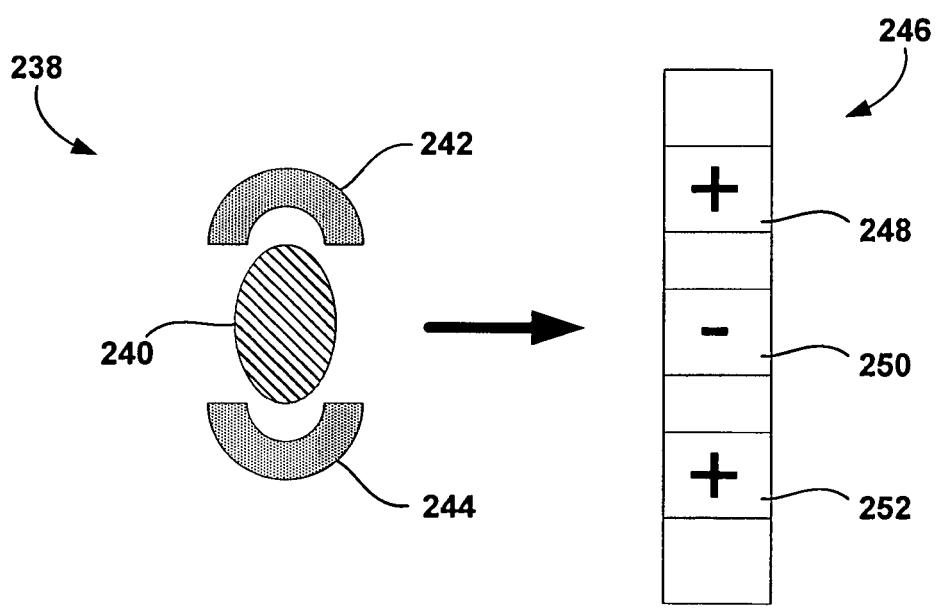

FIGS. 11A and 11B illustrate possible field shape groups 226 and 238 that could be provided by field shape selection menus of any GUIs described herein. In particular, field shape groups 226 and 238 are of the idealized neuron activation type to represent which tissue would be activated from the electrical stimulation therapy. As shown in FIG. 11A, activated neurons are represented by field shape 228 which is an idealized oval, e.g., stripes, and the inhibited neurons are represented by field shape 230 which is a half-circle arc (e.g., with concave and convex sides) to symbolize a shield of those neurons from being activated from field shape 228. The neuron activation field shape group 226 may have shields present on one side of activation field shape 228. To further describe this shielding concept, the activation field shape 228 may be equivalent to cathode 236 of lead 232 whereas field shape 230 may be equivalent to anode 234 of lead 232. Field shape 230 may be referred to as a shield, as the shield does indicate the shape of the activation of neurons. In addition, providing the field shapes 228 and 230 of field shape group 226 may eliminate the need to indicate the vector of the electrical current because the vector is inherent with the activation and shield representations of field shape group 226. Alternately, a clinician may be allowed to select field shape groups that most closely represent the clinician's mental model of the operation of the stimulation therapy.

FIG. 11B shows field shape group 238 which includes field shape 240 surrounded by field shapes 242 and 244. Field shape 240 is the neuron activation field shape while field shapes 242 and 244 are the inhibition or shielding field shapes. Field shape group 238 may be equivalent to the electrode combination of lead 246. Field shape 240 correlates to cathode 250 while field shapes 242 and 244 correlate to anodes 248 and 252, respectively. The clinician may select field shape group 238 in order to stimulate a desired tissue of patient 12 while preventing adjacent tissue from being activated during therapy. Inhibition of certain tissue may prevent the creation of adverse side effects that may occur from unshielded activation of tissue.

Since the shield, e.g., field shapes 230, 242, or 244, is used by the clinician to prevent activation from occurring at those locations, the shield may be similar to a keepout region of which the clinician prefers not to activate those neurons. In particular, field shapes 230, 242, or 244 may be intuitive to novice clinicians or clinicians that prefer to separate actual physics of generating electrical stimulation from the physiological programming process for efficacious therapy. Shapes of field shapes 230, 242, or 244 may change according to activation field shapes 228 and 240 near each shield field shape. In other examples, a shape different than the half-circle may be used to represent the shielding or inhibition concept to the clinician. For example, the shield may be shown as an open circle, a line, a triangle, or any other shape.

Figure 12:
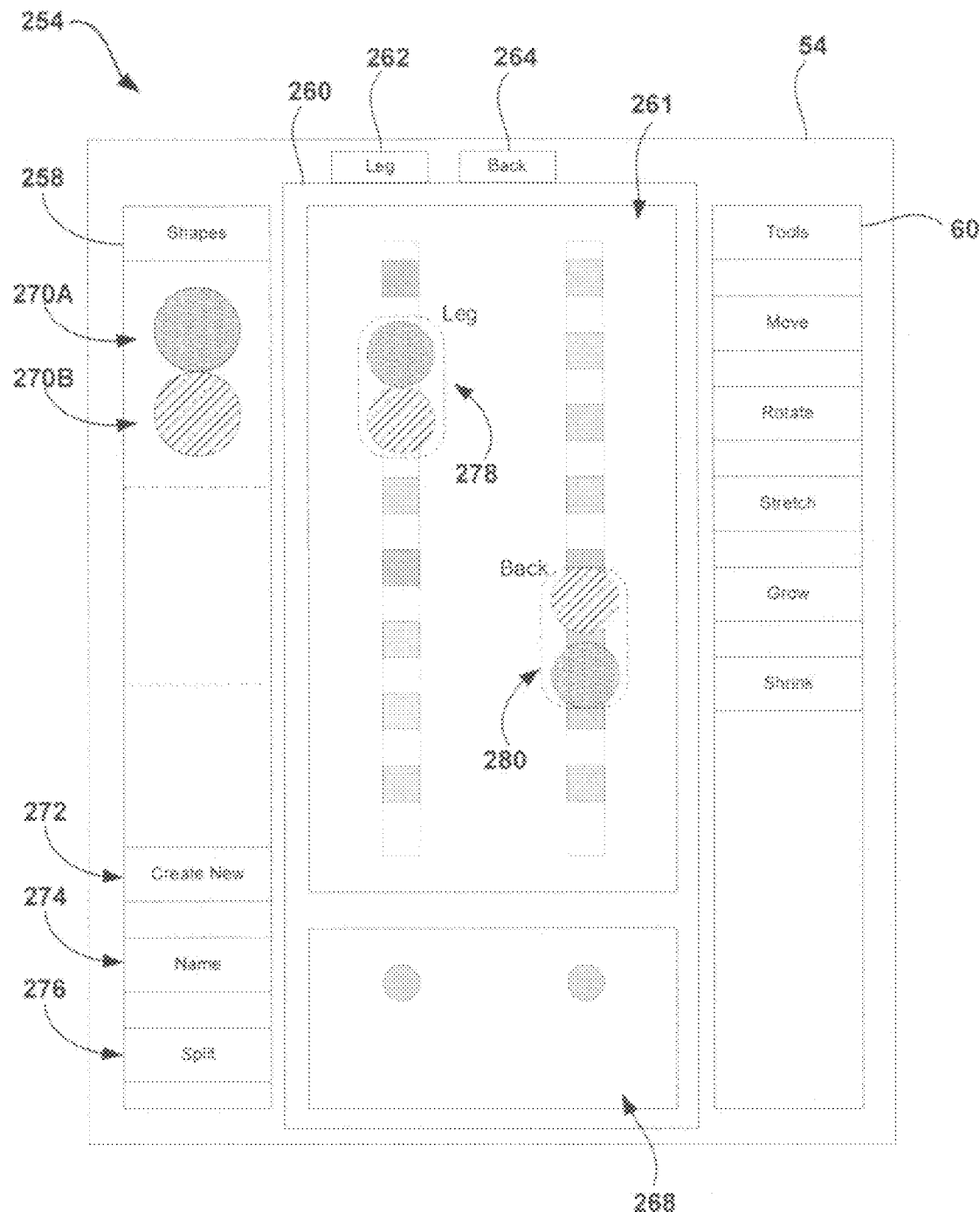
FIG. 12 is a conceptual illustration of a user interface with an activation and inhibition icons for multiple locations within the stimulation region.

FIG. 12 describes GUI 254 and the usage of field shape selection menu 258 in relation to stimulation region 260. As shown, GUI 254 includes field shape selection menu 258, field shape manipulation tool menu 60, and a stimulation region 260 comprising side and depth regions 261 and 268. In some embodiments, stimulation region 260 need not include stimulation depth region 268. Field shapes 270A and 270B (collectively "field shape group 270") in field shape selection menu 254 are activation functions, wherein field shape 270A is an inhibition shape and field shape 270B is an activation shape. Field shapes 270A and 270B may be placed within stimulation field 260 and are usually are placed over a particular one of lead representations in side view region 261. As shown, field shape groups 278 and 280 have been placed within side view region 261.

When the clinician drags field shapes from field shape selection menu 258 to one of the leads, GUI 254 may support a "snap" ability that correctly places the selected field shapes directly over one or more full electrodes when the clinician positions the field shape close enough to the actual center of the electrode or just the nearest full electrode of the lead. In additional examples, stimulator 14 may not be capable of centering a field shape away from the center of an electrode. In this case, stimulator 14 may snap the shape to the nearest full electrode. Hence, processor 22 (FIG. 2) may be configured to operate with knowledge of the actual capabilities of the stimulator 14 for which programming is performed. Snapping field shapes into place over particular electrodes, for stimulators that are capable or incapable of centering a field shape away from the center of an electrode, may reduce time spent by the clinician in attempting to precisely place field shapes over a particular electrode.

In other examples, field shape groups 278 and 280 may not need to be placed over a particular electrode. If stimulator 14 includes multiple current or voltage sources, the stimulator may support placing field shape groups 278 and 280, or any other field shapes, anywhere within stimulation region 260. Stimulator 14 may be capable of creating activation of tissue away from electrodes through the use of multiple electrodes adjacent to the desired stimulation area. However, the clinician may not need to know how stimulator 14 will function in order to reproduce the stimulation field defined by the placement of field shapes within stimulation region 260. In this manner, the clinician may focus on correct placement of the field shapes to treat certain tissue of patient 12.

GUI 254 also allows the clinician to manage field shape groups 278 and 280. The clinician may be able to name field shape groups 278 and 280 or other field shapes, selectively activate or inactivate field shapes, or add new field shapes to stimulation region 260. As an example, a field shape group 270 may be named to refer to an anatomical region of patient 12 in which the group produces paresthesia or other therapeutic effects, e.g., such as leg, back, arm, or the like. In FIG. 12, the clinician has named field shape group 278 as "Leg" and field shape group 280 as "Back." Field shape group 278 has been snapped to full electrodes. However, field shape group 280 is located between full electrodes according to the desire of the clinician. In addition, GUI 254 and stimulator 14 may support simultaneous field shapes placed over each other. Programmer 20 may generate stimulation parameter values, i.e., programs, for each of field shape groups 278 and 280 and require stimulator 14 to interleave the programs for each group in order to reproduce the therapy defined by the clinician. Field shape groups 278 and 280 may also be characterized by attributes of their resulting stimulation. These field shapes categories may organize field shapes according to field shapes that provide 'deep,' 'medial,' or 'lateral' field shapes. These field shapes may also be categorized according to longitudinal or transverse field shapes.

As also shown in FIG. 12, GUI 254 may support tabbed programming. Tabbed programming refers to the method of organizing multiple groups of field shapes placed within stimulation region 260. The clinician may select a tab, e.g., leg tab 262 or back tab 264, to allow manipulation of the corresponding group of field shapes. For example, if the clinician selects leg tab 262, field shape group 278 may be manipulated with icons from the field shape manipulation tool menu 60 or added to using field shape group 270 or other field shapes from field shape selection menu 258. Instead of tabbed programming, GUI 254 may include other icons or indications that allow the clinician to access the groups of field shapes within stimulation region 260.

Figure 13A:
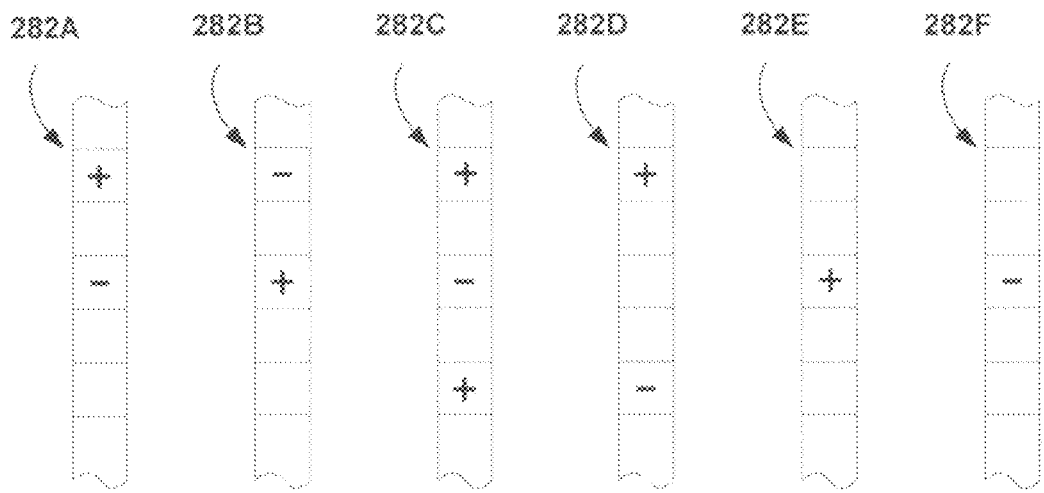
FIGS. 13A-13C are example electrode configurations for specific lead groups.
Figure 13B:
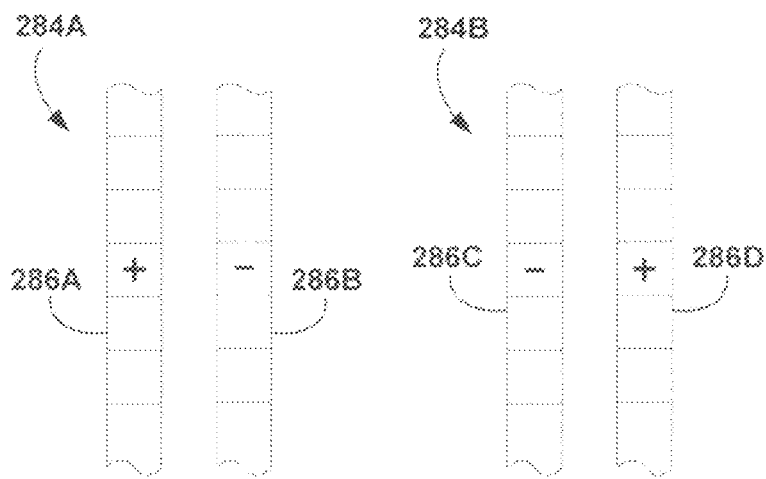
Figure 13C:
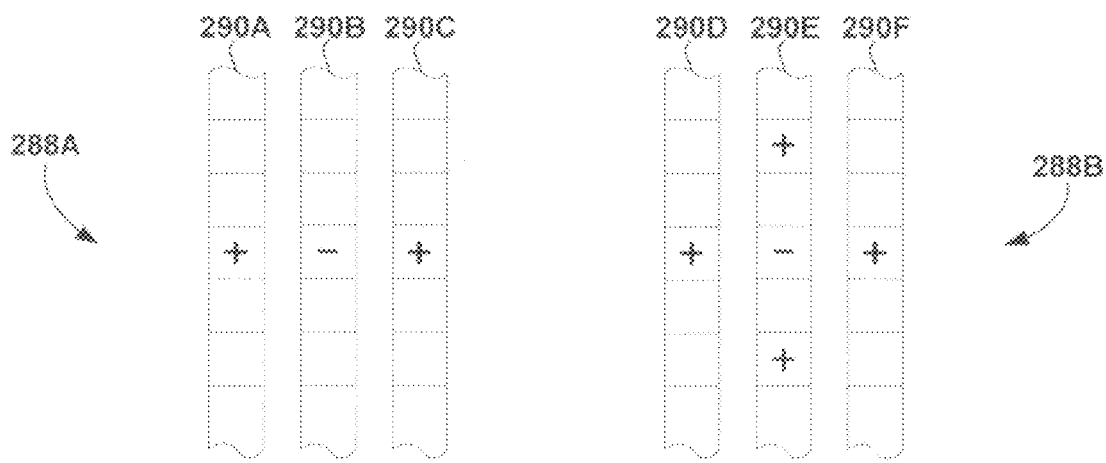

FIGS. 13A-13C provides examples of specific electrode configurations for field shapes that may be used by programmer 20. Each field shape is essentially a template that defines a particular set of stimulation parameter values to begin the programming process. Field shapes may be preset to cover the most common electrode configurations used by the clinician or for a particular therapy. The clinician may add more field shapes to the library of programmer 20, or the clinician may request new field shapes from a technician or manufacturer of the programmer. The preset electrode configurations correlate to field shapes used by GUI 52, for example, may be designed to allow full use of actions in the field shape manipulation tool menu for clinician customization. Less common electrode configurations may be created by the clinician through manipulation of the field shapes, combination of field shapes, or any other type of field shape functionality desired by the manufacturer or clinician.

As shown in FIG. 13A, longitudinal field shapes may include common electrode configurations that arise from electrodes located on the same lead. In this manner, the field shapes do not require electrodes from an adjacent lead in order to be implemented. As shown in FIG. 13A, leads 282A-F illustrate example electrode configurations for field shapes created by electrodes on one lead. Leads 282A and 282B include only one anode and one cathode adjacent to each other, while lead 282C includes one cathode flanked by two anodes. Lead 282D illustrates an electrode configuration with an anode and a cathode separated by an unused electrode, and leads 282E and 282F include just one anode and just one cathode, respectively.

However, transverse and three column field shapes may require one or more electrodes from two or more leads implanted within patient 12, e.g., a cathode is located on one lead while an anode is located on another lead. FIG. 13B provides lead pairs 284A and 284B. Transverse electrode configurations may have an anode on lead 286A and a cathode on lead 286B. Alternatively, transverse electrode configurations may have a cathode on lead 286C and an anode on lead 286D. In any case, electrode configuration including two adjacent leads may be used to create certain field shapes for the clinician.

FIG. 13C illustrates common electrode configurations for field shapes that require the use of three leads and electrodes active on each of the three leads. These field shapes may be less common in some therapies where fewer leads provide effective therapy. As shown in FIG. 13C, electrode configuration 288A includes a cathode on lead 290B with anodes on adjacent leads 290A and 290C. Electrode configuration 288B includes a cathode on lead 290E with anodes on each of leads 290D, 290E, and 290F to surround the cathode. It should be noted that any of these electrode configurations may be presented as any of the field shape types described herein. For example, the field shapes associated with the electrode configurations of FIGS. 13A-13C may illustrate current density, an activation function, or neuron activation. Certain field shapes may be eliminated from use by programmer 20 depending on the configuration of leads 16 implanted within patient 12.

In the case of a single activation or inhibition field shape selected by the clinician, programmer 20 may need to automatically place additional activation or inhibition field shapes within the stimulation region. When an opposing field shape is needed to be automatically placed by programmer 20, programmer 20 may maximize the effect of the field shape placed by the clinician. For example, the clinician may select and place an activation field shape to target a particular area of the stimulation region. This placed field shape is essentially a unipolar electrode. Therefore, if stimulator 14 allows, programmer 20 would ideally set the housing of stimulator 14 as an anode to provide low intensity inhibition areas. Otherwise, programmer 20 may select one or more electrodes as anodes (inhibition field shapes) furthest from the desired activation field shape location. Alternatively, a single inhibition field shape would be automatically accompanied by one or more cathodes (activation field shapes) closest to the inhibition field shape in order to maximize the intensity of the inhibition.

FIGS. 14A-14D illustrate different representations of field shape groups as templates to define a stimulation field and corresponding activation model. The examples of field shapes include a long bipole in FIG. 14A, a guarded cathode in FIG. 14B, a 3 lead full guard in FIG. 14C, and a transverse tripole in FIG. 14D. Each template is shown with the active electrodes of each lead, the activation model, and the idealized representation of the model. FIG. 14A provides electrode configuration 292 that includes cathode 294A and anode 294B. Electrode configuration 292 may correspond to activation field shape group 296 or modeled activation model field shapes 300A and 300B (collectively "field shape group 300") placed on spinal cord 298. Field shape group 296 may be the idealized representation that is provided to the clinician within the field shape selection menu. In any case, the activation function formula is used to calculate the activation on the surface of the white matter of the spinal cord.

FIG. 14B shows electrode configuration 302 that includes cathode 304B guarded by anodes 304A and 304C on the same lead. Field shape group 306 includes an activation field shape and two inhibition field shapes that flank the activation field shape according to electrode configuration 302. Field shape group 306 illustrates an idealized activation field shape group which may also be shown by activation model field shapes 310A, 310B, and 310C (collectively "field shape group 310") provided on spinal cord 308. The idealized field shapes of field shape group 306 may be shown using in color in some examples instead of striped or shaded field shapes.

FIG. 14C illustrates an example of three lead full guards which utilizes electrodes on all three leads implanted within patient 12. Specifically, electrode configuration 312 includes cathode 314A of the middle lead being surrounded by two anodes 314B of the same lead and anodes 314B of the leads on either side of cathode 314A. In this manner, the clinician may select idealized activation field shape group 316 to only activate the tissue around the cathode while inhibiting the tissue on all sides of the cathode. The activation model field shapes 320A, 320B, and 320C on spinal cord 318 provide an example of how the tissue will be affected by electrode configuration 312.

Alternatively, FIG. 14D provides a transverse tripole example according to electrode configuration 322 which includes cathode 324A in the middle lead while electrodes of adjacent leads include anodes 324B. The resulting activation of tissue using electrode configuration 322 may be a small area of activated tissue around the cathode as shown by the activation on spinal cord 328. Activation model 330A is shown as surrounded by inhibition models 332B. Therefore, the clinician may select idealized field shape group 326 as and activation field shape with two smaller inhibition field shapes to inhibit tissue on either side of the activated cathode. Any of the configurations shown in FIGS. 14A-14D may be used anywhere along implanted leads or in combination with other configurations in order to treat patient 12.

Figure 15B:
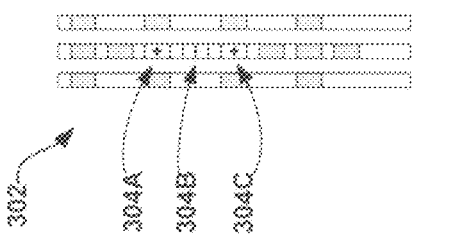
FIGS. 15A-15D are conceptual illustrations of electrode configurations and corresponding current density depths.
Figure 15B:
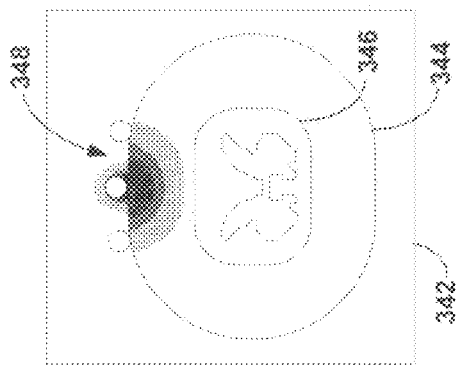
Figure 15D:
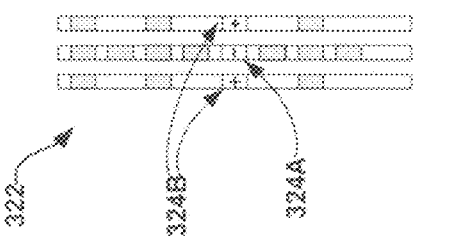
Figure 15D:
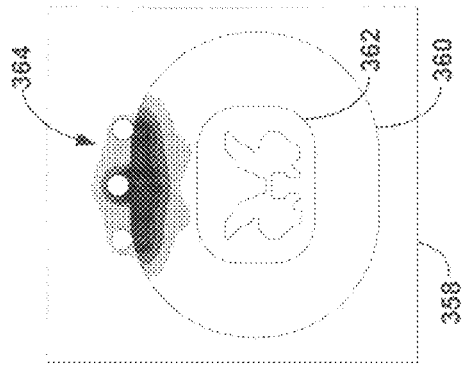
Figure 15A:
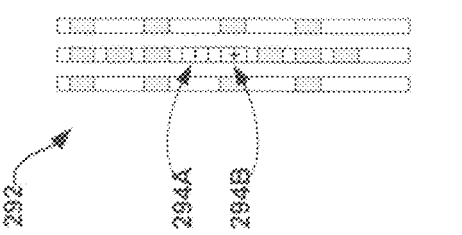
Figure 15A:
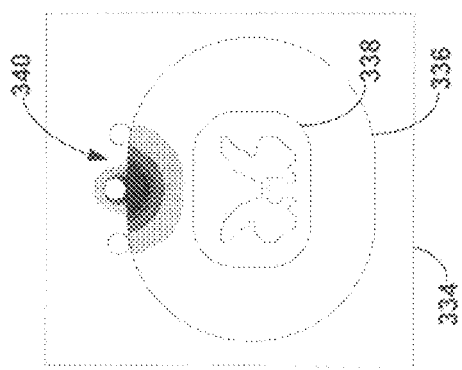

FIGS. 15A-15D illustrate electrode configurations 392, 302, 312, and 322 of FIGS. 14A-14D, respectively, and associated models of current density (e.g., as opposed to the associated activation functions illustrated in FIGS. 14A-14D). As shown in FIG. 15A, electrode configuration 292 is provided to indicate some of the stimulation parameter values that may result in a current density model 340 of axial view 334. Current density model 340 is shown within subarachnoid space 336 adjacent to spinal cord 338. The axial view 334 is a cross-section that corresponds to the middle of cathode 294A in FIG. 15A and FIGS. 15B-15D. Current density model 340 indicates how the current density from electrode configuration 292 will propagate through spinal cord 338 and subarachnoid space 336. Darker shading within current density model 340 indicates higher current density than lighter shading.

FIG. 15B illustrates electrode combination 302 that includes anodes 304A and 304C on either longitudinal side of cathode 304B. In this manner, the current density model 348 indicates that current propagates slightly further from cathode 304B in the radial direction than cathode 294A of electrode configuration 292 that is flanked by only one anode 294B. Axial view 342 includes spinal cord 346 surrounded by subarachnoid space 344.

Figure 15C:
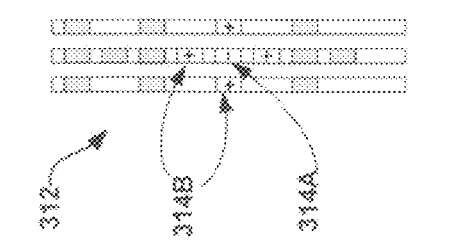
Figure 15C:
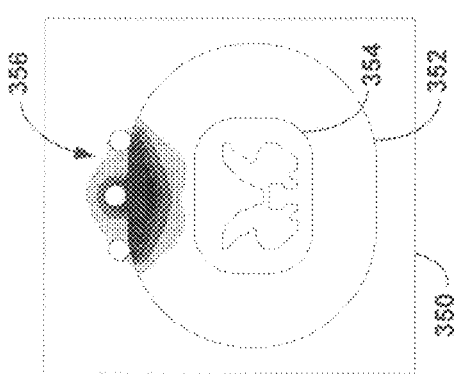

FIG. 15C provides electrode configuration 312 that includes one cathode 314A surrounded by anodes 314B above, below, and on either sides of the cathode. Axial view 350 includes a cross-section of spinal cord 354 surrounded by subarachnoid space 352. Current density model 356 is modeled to be spread out between all electrodes with a greater density further from the cathode. The current density of current density model 356 is shown as increased in surface area and depth in relation to either current density models 340 or 348.

FIG. 15D shows electrode configuration 322 with cathode 324A surrounded by anodes 324B on adjacent leads. In comparison to electrode configuration 312, the transverse configuration of electrode combination 322 spreads the current density along the surface of spinal cord 362 and subarachnoid space 362 without penetrating as deep into the tissue. While not shown in axial view 358, the current density generated from electrode configuration 322 may be reduced longitudinally when compared to electrode configuration 312. These and other configurations may be modeled and provided to the clinician as the stimulation depth region in GUI 52, for example, of programmer 20. Alternatively, axial views 334, 342, 350, and 358 may even be a separate view alternative to the regular GUI that includes the stimulation region.

FIGS. 16A-16B show electrode configurations 392, 302, 312, and 322 of FIGS. 14A-14D, respectively. However, FIGS. 16A-16D illustrate neuron activation plots, or models, for each electrode configuration, instead of current density (FIG. 15) or activation functions (FIG. 14). The area shaded in each neuron model depth view, e.g., shaded area, indicates the neurons that would be activated from stimulation with the associated electrode configuration. The axial views of the spinal cord shown are at the location in the center of the cathode of the leads.

FIG. 16A illustrates electrode configuration 292 and an associated neuron activation plot 370 in an axial or depth view 366. Neuron activation plot 370 is shown within spinal cord 368. Axial view 366 is a cross-section that corresponds to the middle of cathode 294A in FIG. 16A and FIGS. 16B-16D. Neuron activation plot 370 indicates which neurons of spinal cord 368 are activated by the current from electrode configuration 292. Neuron activation plots of FIGS. 16A-16D may be generated using similar stimulation parameters such as pulse width, pulse rate, and current or voltage amplitude. Changes in any of these parameters may change the neuron activation plot accordingly.

FIG. 16B illustrates electrode configuration 302 that includes anodes 304A and 304C on either longitudinal side of cathode 304B. Corresponding neuron activation plot 376 indicates that neurons further into the center of spinal cord 374 are activated from cathode 304B. The presence of nodes 304A and 304B create the deeper neuron activation than electrode configuration 292. Axial view 372 may show spinal cord 374 and neuron activation plot 376.

FIG. 16C illustrates electrode configuration 312 that includes one cathode 314A surrounded by anodes 314B above, below, and on both sides of the cathode. Axial view 378 includes a cross-section of spinal cord 380. Neuron activation plot 382 corresponding to electrode configuration 312 is spread out between all electrodes with a greater degree of neuron activation further from the cathode. The neuron activation illustrated by neuron activation plot 382 is increased in surface area and depth in relation to either neuron activation plots 370 or 376.

FIG. 16D shows electrode configuration 322 with cathode 324A surrounded by anodes 324B on adjacent leads. In comparison to electrode configuration 312, the transverse configuration of electrode combination 322 reduces the activation of tissue along the sides of spinal cord 386 while penetrating the neuron activation deeper within spinal cord 386. While not shown in axial view 384, the neuron activation generated from electrode configuration 322 may be reduced longitudinally when compared to electrode configuration 312. These and other configurations may be modeled and provided to the clinician as the stimulation depth region 61 in GUI 52, for example, of programmer 20. Alternatively, axial views 366, 372, 378, and 384 may be provided as an alternative to the standard stimulation region, e.g., 58, of the GUI's described herein.

Figure 17:
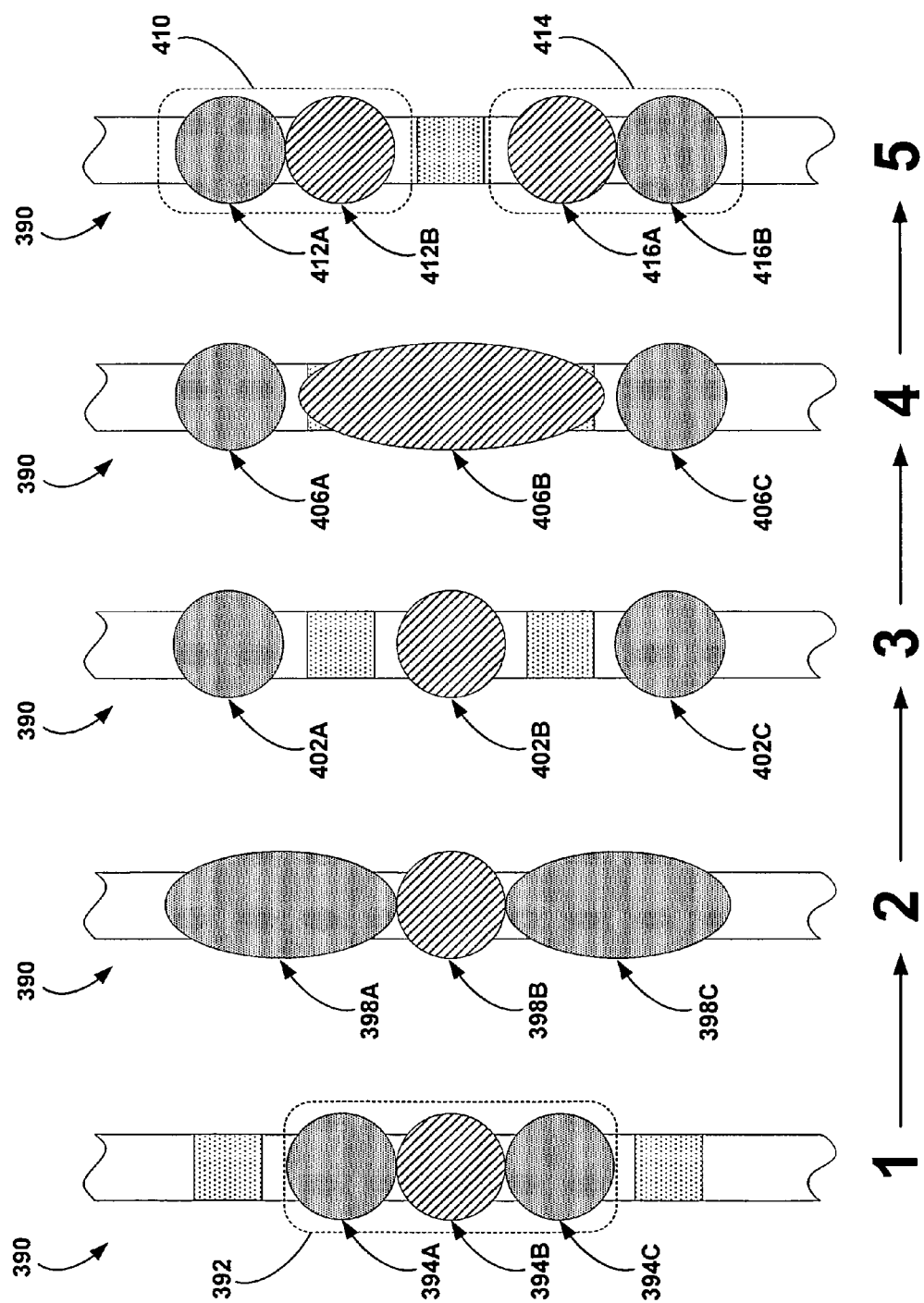
FIG. 17 is a conceptual illustration of a split sequence for a group of activation and inhibition icons.

FIGS. 17-29 are conceptual diagrams illustrating the modification of stimulation shapes using the field shape manipulation tool menu 60 and other tools. FIG. 17 illustrates two actions that the clinician may select from the field shape manipulation tool menu of any of the GUIs shown herein. The clinician may split field shapes 394A, 394B, and 394C which make up field shape group 392 shown with respect to lead 390. Splitting field shapes may move the stimulation field across a plurality of electrodes in a plurality of steps, e.g., five steps as illustrated by FIG. 17, before two separate field shape groups 410 and 414 are created. Conversely, the clinician may merge two or more field shapes or groups of field shapes to cover fewer electrodes. As shown in the example of FIG. 17, the clinician has placed activation field shape group 392, including one activation field shape 394B surrounded by two inhibition field shapes 394A and 394C, onto a representation of a lead 390 with five electrodes. Only three electrodes are covered initially in step 1. Lead representation 390 is shown in each of the five steps as the field shapes are changed according to the movement of active electrodes.

Once the clinician placed field shape group 392 over lead representation 390, the clinician may select the split icon from the field shape manipulation tool menu (not shown). Once the clinician selects this option, processor 22 splits field shape group 392 in step 2 by adding anodes on either side of the initial anodes for field shapes 394A and 394C to create larger inhibition field shapes 398A and 398C on either side of activation field shape 398B. After step 2, the clinician may again select the split icon, or the field shapes may continue splitting until stopped by the clinician. To move to the third step, processor 22 removes the middle anodes such that activation field shape 402B is separated from the other inhibition field shapes 402A and 402C by one full, non-activated, electrode of lead 390. On the fourth step, processor 22 adds cathodes on either side of activation field shape 402B to create one large activation field shape 406B with three cathodes in between inhibition field shapes 406A and 406C. On the fifth and final step of splitting, processor 22 removes the center cathode from the electrode configuration of lead 390 to create two separate field shape groups 410 and 414. Field shape group 410 includes activation field shape 412B and inhibition field shape 412A, and field shape group 414 includes activation field shape 416A and inhibition field shape 416B. The clinician may stop at any one of the steps to create a stimulation field with the shown field shapes, depending on what is desired. In other examples, current density or neuron activation field shapes may be shown during the splitting process, as determined by the clinician. This process may take place in separate splitting operations, or in a single operation that proceeds automatically in a continuous or discrete fashion under the control of the clinician or other user.

In some examples, the steps may be used to automatically progress completely from step one to step five during real-time stimulation therapy programming. In other words, the steps may be used so that patient 12 perceives few or no abrupt changes in therapy during the splitting transition. Alternatively, each of steps 1 through 5 may be subdivided into multiple substeps or intermediate field shapes in order to further reduce the perceptibility of the change in therapy. The changes between each step may be controlled using multiple current sources for the stimulation parameters for each step or interleaving pulses for each stimulation parameters that define the two steps using a single current source. The clinician may specify the number of steps, transition time period, or any other factor that adjusts how programmer 20 controls changes to the electrical stimulation.

Figure 18A:
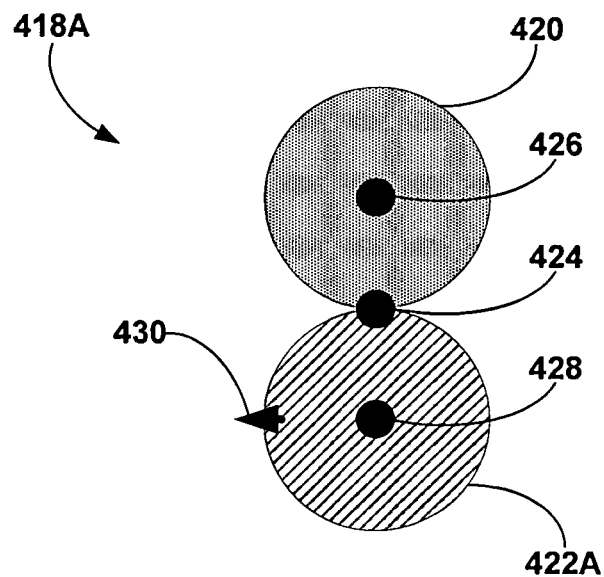
FIGS. 18A and 18B are conceptual illustrations of example activation and inhibition icons with pivot points to move and resize the icons.
Figure 18B:
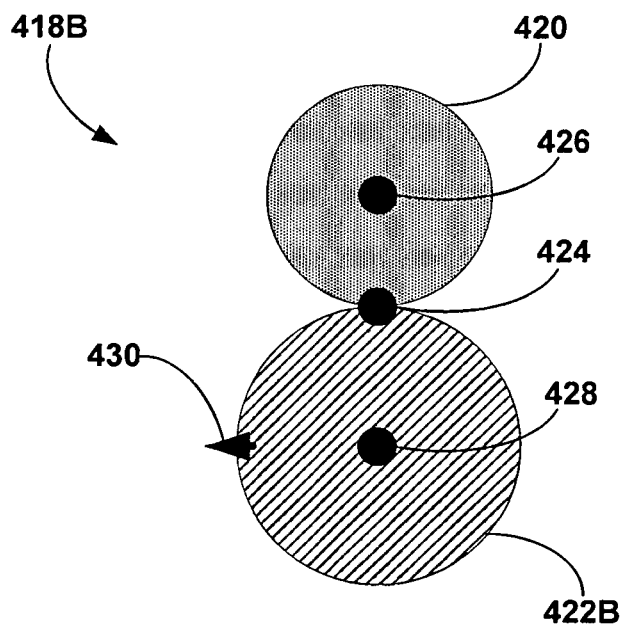

FIGS. 18A and 18B illustrate example control handles for field shapes of field shape groups 418A and 418B to allow manipulation of the field shapes. In the example of FIG. 18A, field shapes 420 and 422A are activation/inhibition function field shapes connected in field shape group 418A. Similar control handles may be provided for other field shape types. Field shape group 418A include three control points 424, 426, and 428, each operating as a control handle, which allow the clinician to manipulate each field shape 420 and 422A or both field shapes together. In this manner, the clinician may selectively adjust one or both field shapes 420 and 422A as desired. The clinician may use a pointing device of programmer 20 to select a particular control point ("handle") to adjust the associated field shape, such as the orientation or position of field shapes 420 and 422A.

As shown, inhibition field shape 422A includes control point 428 that allows positional adjustment, i.e., movement, of only inhibition field shape 422A. Activation control point 426 allows positional adjustment of only activation field shape 420. In addition, the two field shapes together form a single field shape group 418A that also includes control point 424 that adjusts the position of field shape group 418A as a single object. In addition to three control points 424, 426, and 428, field shapes 420 and 422A may also have one or more control arrows 430 that allow the clinician to change the size of the respective field shapes. The clinician may select control arrow 430 and move the control arrow to change the size of field shape 422A, e.g., by stretching or shrinking field shape 422A in one dimension or simultaneously expanding or shrinking field shape 422A in equal proportions in two dimensions. The resulting stretching of inhibition field shape 422A with control arrow 430 may create larger inhibition field shape 422B of field shape group 418B. Control points 424, 426, and 428 and arrow 430 may be similar to repositioning and resizing tools provided in graphical drawing applications such as Microsoft Visio. A control arrow may control a group of field shapes or a single field shape. In general, the control arrow may be placed on an outer edge of the field shapes; however, the control arrow may be placed anywhere on the field shapes. In other examples, the control tools may include rotational control points that permit rotation of a set of field shapes, e.g., from a vertical orientation to a horizontal or angular (e.g., rotated 45 degrees) orientation.

In some examples, the use of control points, control arrows, or other such adjustment options on field shapes may mean that separate actions in a field shape manipulation tool menu may not be necessary for manipulation of the field shapes. In other words, each action represented by an icon in the field shape manipulation tool menu may be substituted by a tool located on each field shape, which can be manipulated with a stylus, mouse, directional arrows, trackball or other pointing device. These tools may be similar to control points 424, 426, and 428 and control arrow 430. In addition, the clinician may be able to select how to manipulate the field shapes, either through the field shape manipulation tool menu or control points.

Figure 19:
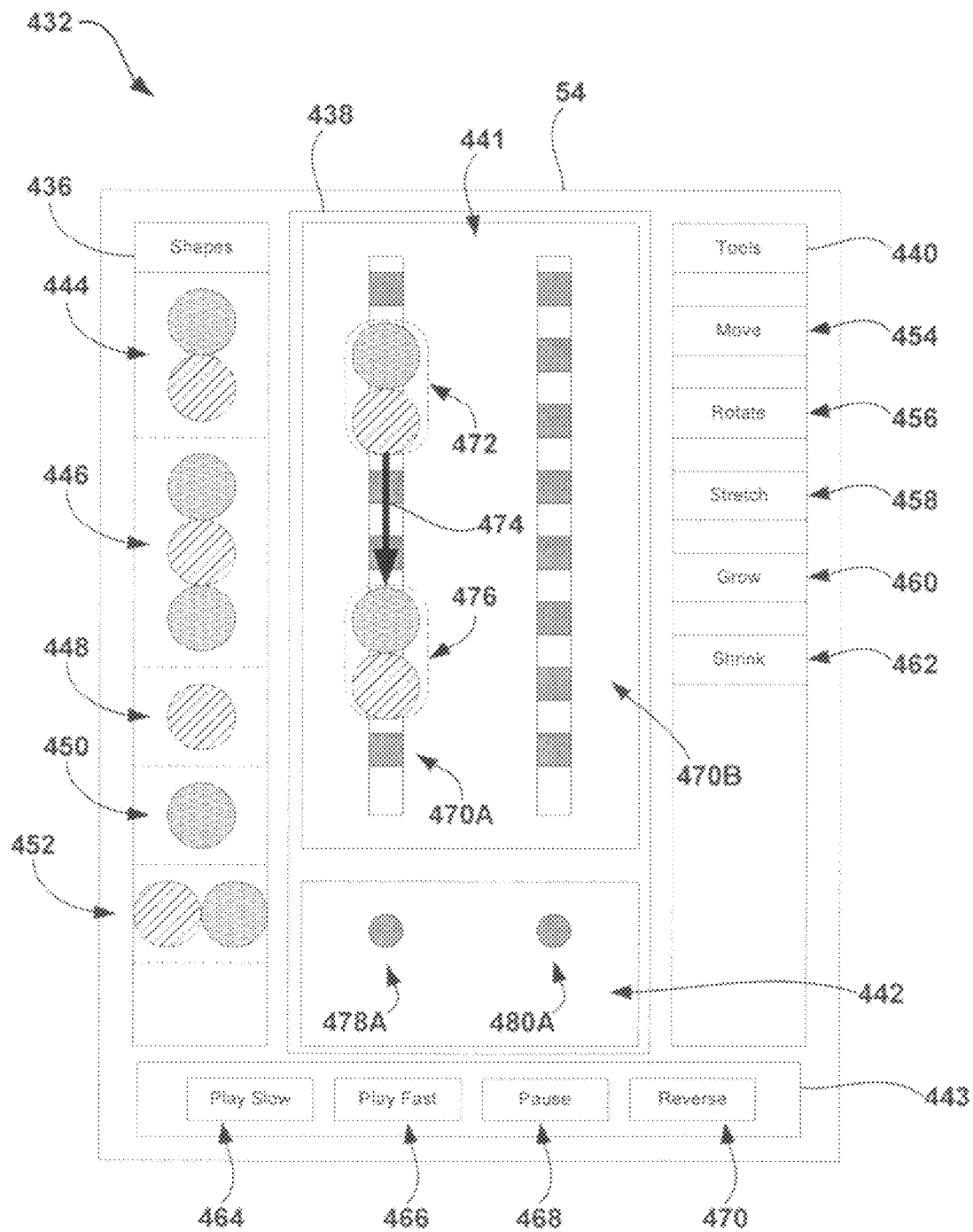
FIG. 19 is a conceptual illustration of a user interface with activation and inhibition icons moved within the stimulation region.

FIG. 19 is an example GUI 432 in which the clinician has selected move icon 454 from field shape manipulation tool menu 440. GUI 432 is similar to GUI 52 (FIG. 4) but includes additional features. As shown in FIG. 19, GUI 432 includes field shape selection menu 436, field shape manipulation tool menu 440, and stimulation region 438 including side view region 441 and depth view region 442. In addition, the user may control the manipulation of field shapes within stimulation region 438 with play slow icon 464, play fast icon 466, pause icon 468, and reverse icon 470.

Field shape group 472 is initially placed within stimulation region 438 over lead side view 470A. Field shape group 472 may be created by the clinician dragging field shape group 444 from field shape selection menu 436. The clinician uses field shape manipulation tool menu 440 to alter field shape group 472 within stimulation region 438. The movement of field shape group 472 may be caused when the clinician selects move icon 454 from field shape manipulation tool menu 440. The clinician may then select field shape group 472 and dragging it to the new location as indicated by field shape group 476. Arrow 474 indicates the direction in which field shape group 472 is moved within stimulation region 438 to the new or target location the stimulation region. GUI 432 may show the new location of field shape group 476 and original location of field shape group 472 together so that the clinician has an indication of the move action just completed. Arrow 474 may show the moved field shape combination, or another technique such as transparency, animation, or numbering may be used in place of the arrow. In some examples, GUI 432 may prompt the clinician to confirm the movement of field shape group 472 before field shape group 476 is completed.

The actual movement of field shape group 472 within stimulation region 438 may be done without changing the stimulation therapy. In order to change the stimulation therapy according to the new location of field shape group 472, the clinician may utilize implementation toolbar 443 as shown at the bottom of GUI 432. Implementation toolbar 443 may allow the clinician to control how and when the change is transferred to stimulator 14 for changing the stimulation delivered by the stimulator. Implementation toolbar 443 may include play slow icon 464, play fast icon 466, pause icon 468, and reverse icon 470, similar to a video or audio playback system. Play slow icon 464 and play fast icon 466 indicates that stimulation transitions from the starting field shape group 472 to the field shape group 476 gradually or quickly. Speed control may be achieved by varying the number of steps, e.g., the number changes to electrode configuration and other stimulation parameter values, between endpoints, e.g., initial and target field shape location/configuration, for the desired change in stimulation fields. Speed control may additionally or alternatively be achieved by changing the size of those steps, or the rate at which steps are sent to stimulator 14 for execution. In other words, the clinician may have control of how stimulator 14 shifts from the old therapy using field shape group 472 to the new therapy utilizing the new field shape group 476. This control may only be necessary when the clinician is not providing stimulation therapy according to the programming in real-time. In other embodiments, stimulation changes may take place in real-time, wherein parameter changes are sent to stimulator 14 as soon as field shape group 472 is modified.

Figure 20A:
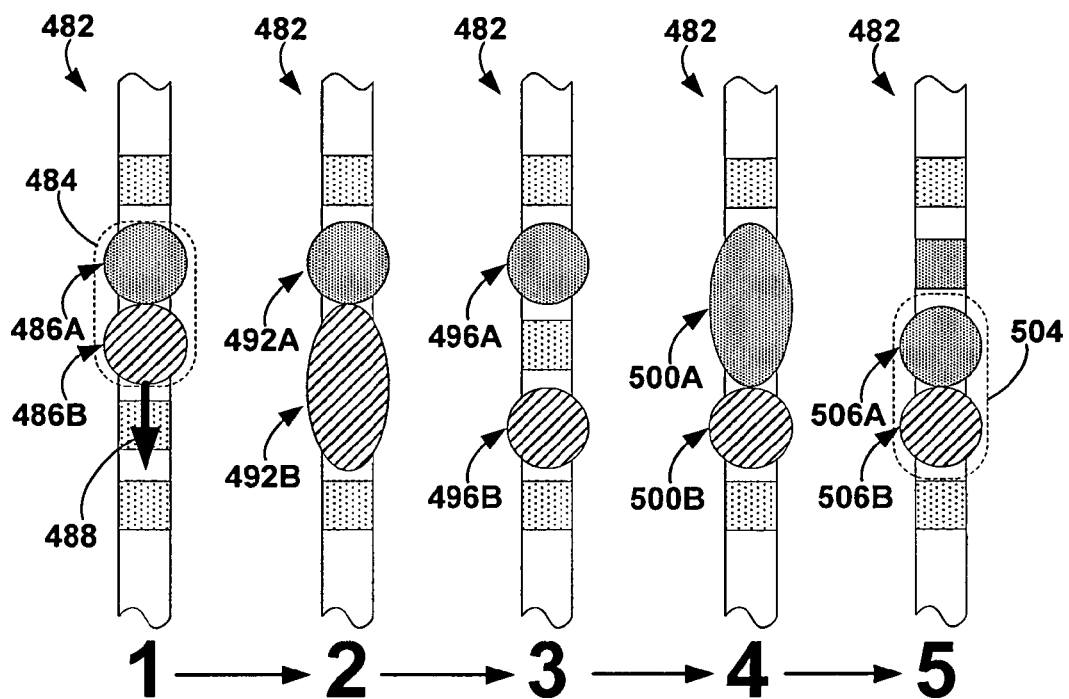
FIGS. 20A-20B are conceptual illustrations of move sequences for a group of activation and inhibition icons.
Figure 20B:
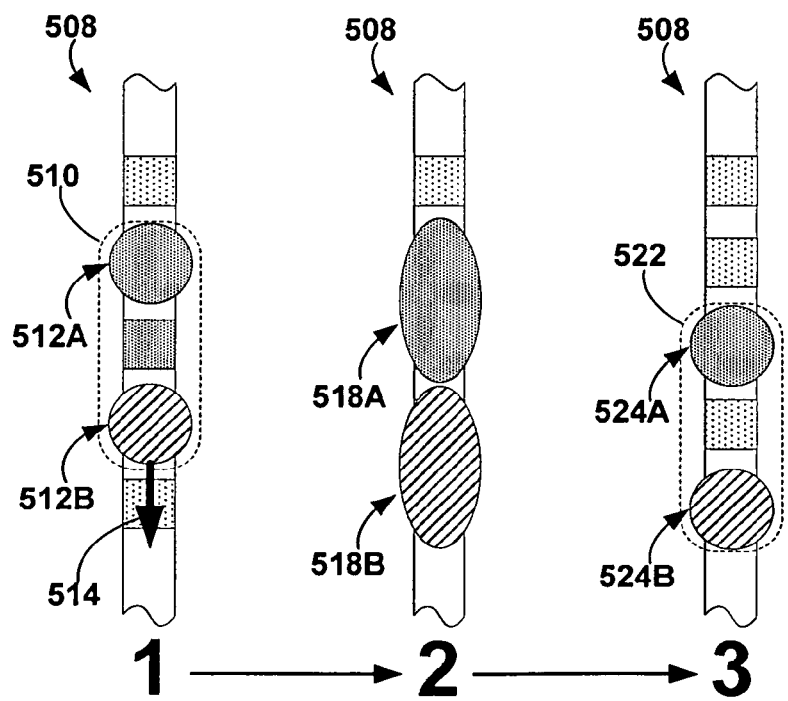

FIGS. 20A and 20B provide example methods for moving field shape groups in an iterative manner so that patient 12 does not feel an abrupt change in stimulation therapy when the field shape groups are moved. FIG. 20A shows field shape group 484 over lead representation 482. Field shape group 484 includes field shapes 486A and 486B over two of the five electrodes of lead representation 482. Arrow 488 indicates the direction in which the clinician has desired to move field shape group 484.

The steps from one to five of FIG. 20A show changing field shape group 484 by iteratively adding and removing anodes and cathodes along the lead representation. In the second step, a cathode is added in the direction of arrow 488 along lead representation 482 to create field shape 492A and field shape 492B before the original cathode is removed in step three to create field shape 496A and field shape 496B. In step four, an anode is added to lead representation 482 and the original cathode location to create field shape 500A and field shape 500B before the original anode is removed in step five along lead representation 482 from the electrode combination of step 498. The resulting field shape group 504 includes field shapes 506A and 506B moved down one electrode position of lead 482.

In this manner field shape group 484 may be shifted to the new position of field shape group 504 without turning the therapy off and then on again. Patient 12 may not perceive abrupt changes in therapy during these five steps. Alternatively, each of these five steps may be subdivided into one or more substeps in order to further reduce the perceptibility of the change to patient 12. Furthermore, although described with reference to automatic steps in which the user controls direction and rate using the controls of implementation toolbar 443, other embodiments may involve the user manually and discretely controlling each step in either direction using implementation toolbar controls, such as arrows, or graphical forward and back buttons. Other field shape group types of more than two field shapes may move in a similar manner such that only one anode or cathode is added or removed at any one time.

FIG. 20B shows field shape group 510 with spaced electrodes and a possible method in which to move field shapes 512A and 512B. In either case, the movement of field shapes 512A and 512B may employ multiple steps to reduce the coarseness of field shape group 510 movement and associated therapy changes. The movement of field shape group 510 may occur in fewer steps than illustrated in FIG. 20A because field shapes 512A and 512B are separated along the electrodes of lead 508. Multiple anodes and cathodes may be added or removed to more quickly change the field shape locations. In this manner the second step of FIG. 20B involves the addition of an anode and cathode in the direction of arrow 514 to produce field shapes 518A and 518B along lead 508. Step three involves removing the original anodes and cathodes to create field shape group 522 made up of field shapes 524A and 524B on lead 508.

Single source systems, i.e., in which a single source, such as pulse generator 38, delivers current or voltage stimulation, may shift field shapes coarsely because of needing to make the change in electrode configuration with fewer steps. However, multiple source systems, i.e., in which multiple sources deliver current or voltage simultaneously, may be able to shift the field shapes, and corresponding electrode configurations smoothly with a greater number of smaller steps between the old and new field shape locations. The smoother transitions with multiple sources may also utilize partial electrode activation to make the movement of the field shapes as continuous as possible. Partial electrode activation may refer to delivery of stimulation energy (e.g., current or voltage) to both a starting electrode and an ending electrode to effect a transition from one to the other over one or more steps. For example, to move a field shape from a first electrode to a second electrode, e.g., for rotation or other movement, the stimulation delivered to the first electrode may be gradually decreased while the stimulation delivered to the second electrode is gradually increased, until the first electrode delivers no stimulation amplitude for the pertinent field shape and the second electrode delivers all of the stimulation amplitude for the field shape, at which time the transition is complete.

Alternatively, moving field shapes in this manner may not be necessary when a clinician programs the therapy off-line.

Figure 21:
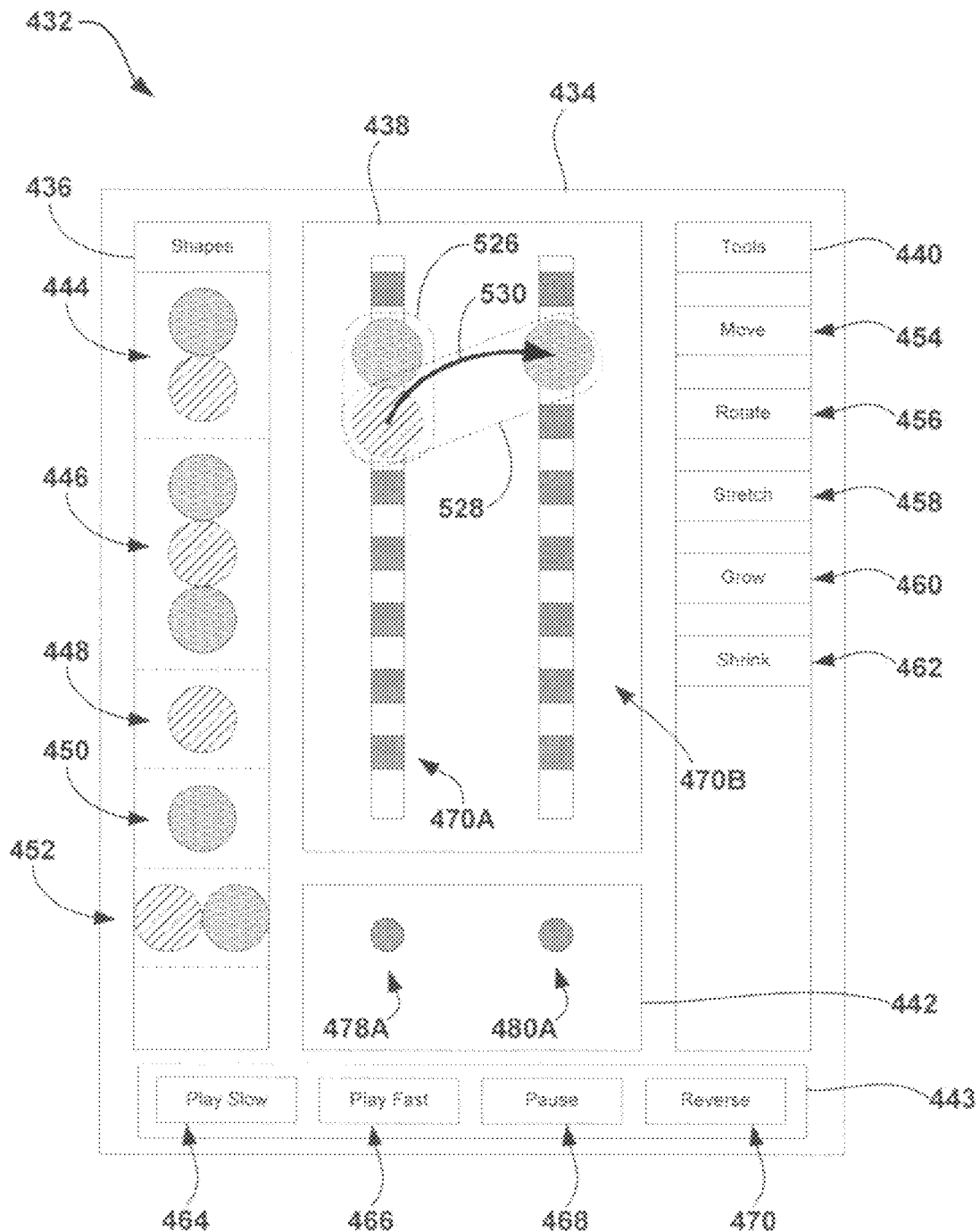
FIG. 21 is a conceptual illustration of a user interface with activation and inhibition icons rotated within the stimulation region.

FIG. 21 illustrates an example of GUI 432 with field shape group 526 being rotated within the stimulation region 438. In the example of FIG. 21, the clinician has selected rotate icon 456 from field shape manipulation tool menu 440 and selected the desired field shape group 526 to be rotated from lead side view 478A. Specifically, the clinician has indicated with arrow 530 to move field shape group 526 about the activation field shape (illustrated as striped in FIG. 21). The clinician has indicated that the new location of the inhibition field shape of field shape group 526 is rotated to lead side view 528. Hence, the activation field shape of field shape group 526 and 528 is the anchor for the rotation of the inhibition field shape from an electrode on lead side view 470A to an electrode on lead side view 470B. The pending rotation of field shape group 526 to field shape group 528 is represented by arrow 530 showing the rotational direction of the original field shape group. Other representations of field shape groups 526 and 528 may include transparencies, opaque field shapes, animations, or other representations that indicate a transition between an original and new field shape group.

Once the clinician has selected to rotate field shape group 526, the actual change to stimulation therapy in real-time programming situations may wait until the clinician confirms the change to the stimulation field in stimulation region 438. The clinician may also use an implementation toolbar 443 to indicate how to change stimulation therapy. In some embodiments, as discussed above, the implementation toolbar may include controls that allow the clinician to discretely control each of a plurality of steps from the initial field shape or group 525 to the target field shape or group 528. In other examples, the change of field shape group 526 to field shape group 528, and the resulting change in delivered stimulation therapy, may occur instantaneously with shape movement and continue until the clinician stops rotating the field shape group.

Figure 22A:
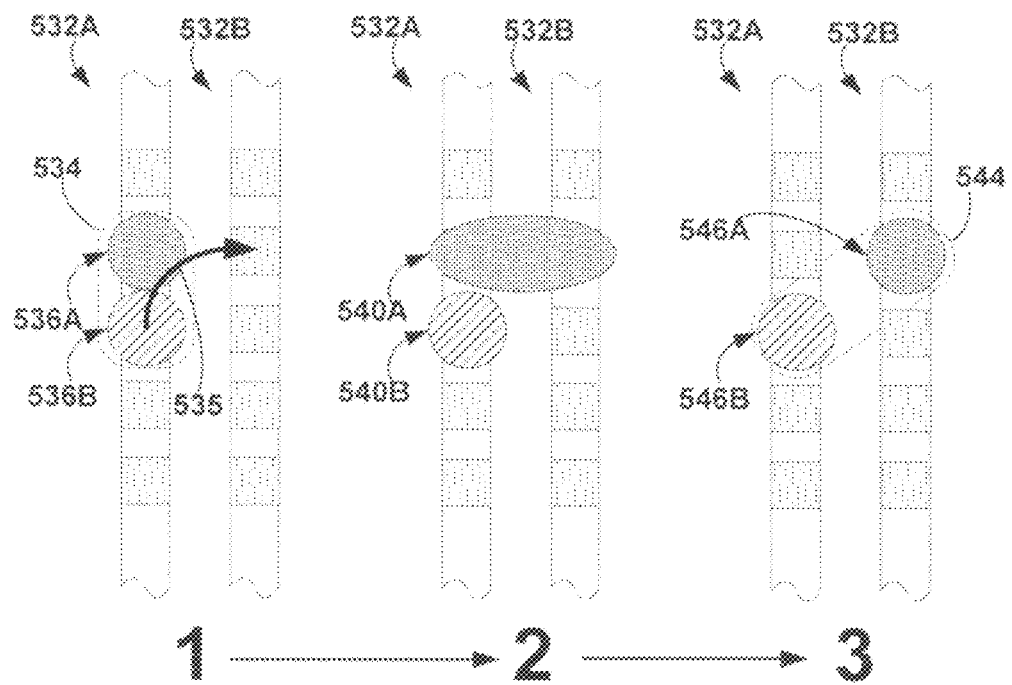
FIGS. 22A-22B are conceptual illustrations of rotate sequences for a group of activation and inhibition icons.
Figure 22B:
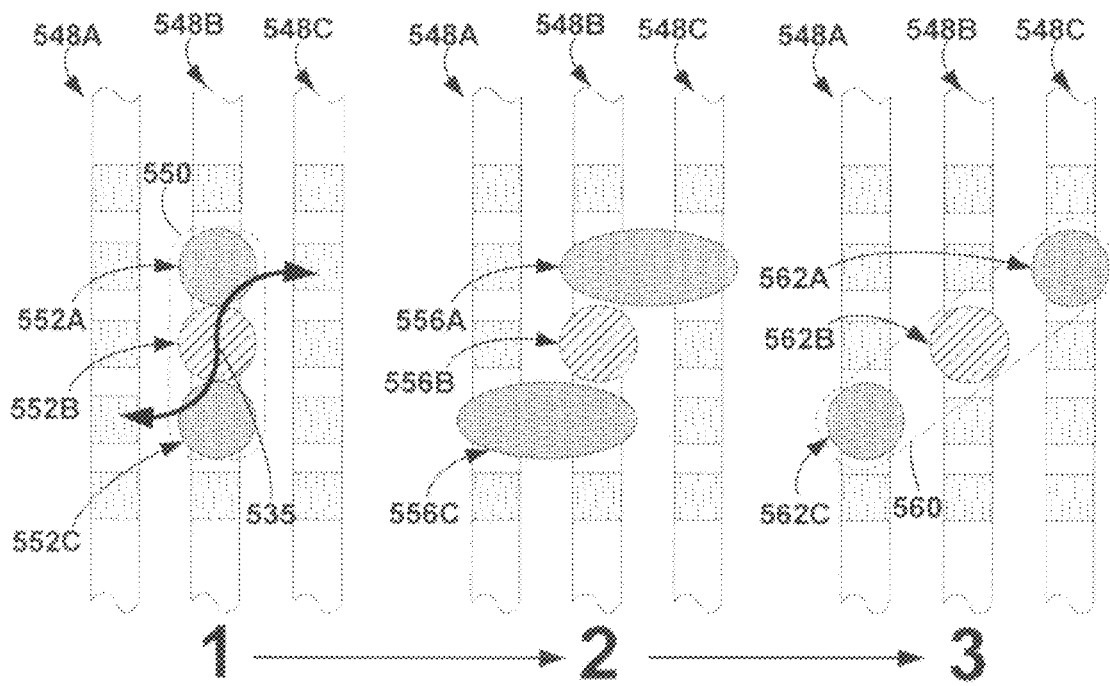

FIGS. 22A and 22B are examples of how programmer 20 may direct the rotation of a field shape group during real-time programming with patient 12. FIG. 22A illustrates lead representations 532A and 532B with field shape group 534 located on lead representation 532A. In three steps, the clinician rotates field shape group 534, specifically inhibition field shape 536A, in the direction of arrow 535 around the anchor position of activation field shape 536B. In the first step the clinician places field shape group 534 onto lead representation 532A, wherein the field shape group includes inhibition field shape 536A and activation field shape 536B. There is no field shape over lead representation 532B, but the clinician desires to rotate field shape group 534 in the direction of arrow 535. In the second step, an anode is added on the electrode of adjacent lead representation 532B to lead representation 532A. The resulting intermediate field shape group includes field shape 540A across both lead representations 532A and 532B and field shape 540B still on lead representation 532A. In the third step, the original anode is removed to result in field shape group 544 spreading across lead representations 532A and 532B in a diagonal field shape group. Field shape group 544 includes inhibition field shape 546A and activation field shape 546B. In some examples, the clinician may continue to rotate field shape group 544 around the anchored cathode of field shape 546B shown as the activation field shape.

FIG. 22B illustrates an initial field shape group 550 within three lead representations 548A, 548B, and 548C (collectively "leads 548") as the first step. Field shape group 550 includes a cathode for field shape 552B surrounded by two anodes of field shapes 552A and 552C. Field shape group 550 is shown as activation function field shapes, so field shape 552B is an activation field shape and field shapes 552A and 552C are inhibition field shapes. Two-headed arrow 535 indicates the direction in which inhibition field shapes 552A and 552B are rotated about activation field shape 552B towards leads 548C and 548A, respectively. The second step of the rotation of field shape group 550 includes adding anodes to the adjacent electrodes on adjacent lead representations 548A and 548C in the direction of arrow 535 which in turn creates larger inhibition field shapes 556A and 556C over multiple lead representations. The third step includes removing the original anodes on lead representation 548B such that the only inhibition field shapes are inhibition field shapes 562A and 562C on lead representations 548A and 548C. Activation field shape 562B remains in its original location of the middle of lead representation 548B to create field shape group 560. Similar to the top image, the clinician may be able to continue rotation of field shape group 560 around the anchored cathode that creates field shape 562B. In this case of FIG. 22B, the centroid of field shape groups 550 and 560 are used as the anchor point when rotating the field shape groups. In other field shape groups, the cathode may not be located at the center of the field shape group or an anode may be used as the anchor point when rotating the field shape group.

As indicated previously with the manipulation of field shapes, the rotation of field shape groups in single current source stimulator 14 may be coarse. However, a multiple current source stimulator 14 may be capable of creating partial electrodes to create a more seamless or continuous movement of the field shape group.

Figure 23:
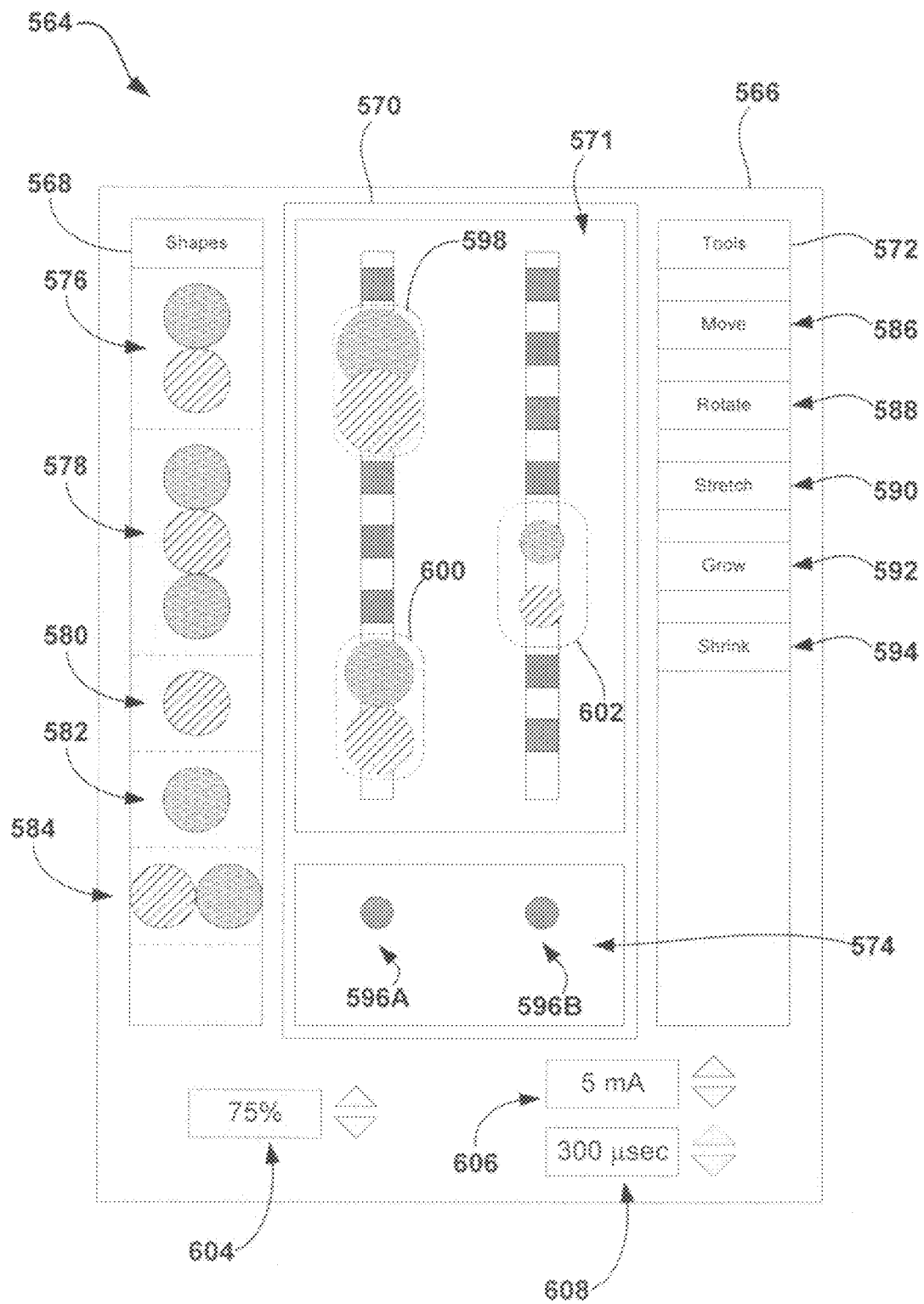
FIG. 23 is a conceptual illustration of a user interface with activation and inhibition icons resized within the stimulation region.

FIG. 23 is an example of manipulating field shapes and field shape groups in such a manner as to grow or shrink the shapes in size, illustrated with respect to a GUI 564. GUI 564 includes field shape selection menu 568, field shape manipulation tool menu 572, and a stimulation region 570 including side and depth view regions 571 and 574. In addition, GUI 564 includes size input 604, current amplitude input 606, and pulse width input 608. The clinician changes the size of a field shape or field shape group by selecting a desired field shape and selecting either grow icon 592 or shrink icon 594 of field shape manipulation tool menu 572. The dotted lines indicate the selected field shape group, such as field shape groups 598, 600, or 602. GUI 564 illustrates example bigger shapes, such as field shape group 598, resulting from growing the original field shape group selected from field shape selection menu 572 to smaller shapes, such as field shape group 602, resulting from shrinking the selected field shape group.

The clinician may change the size of any field shape or field shape group through a variety of control mechanisms, such as size input 604, current amplitude input 606, and pulse width input 608. The clinician may first add the field shape group from field shape selection menu 568, and adjust the size of the selected field shape as desired. Size input 604 may allow the clinician to adjust the size of each selected field shape group as a percentage of the original field shape group. For example, original sized field shape group 598 may be shrunk 75% to field shape group 600. Size input 604 changes may correspond to voltage amplitude or current amplitude changes, depending upon desires of the clinician or the configuration of system 10. Current amplitude input 606 allows the clinician to adjust the current amplitude of the field shape group, and pulse width input 608 determines the pulse width of the electrical pulses delivered to patient 12.

In addition to the inputs shown in GUI 564, other input mechanisms may be used in alternative embodiments. For example, the clinician may provide input via text entry boxes, dials, sliders, up/down arrows, drop-down menus or the like.

In other embodiments, the clinician may change the size of a field shape or field shape group by grabbing an outer edge of the field shape and drag the edge out to grow the field shapes or in to shrink the field shape. The clinician may initially configure GUI 564 to include any input mechanism necessary to effectively program stimulation therapy.

As indicated, the grow icon 592 or shrink icon 594 may be used for any particular field shape, even if the field shape is within a field shape group, or a complete field shape group. Further, any of the field shape manipulation mechanisms of GUI 564 may be used within depth view region 574 over axial views 596A and 596B of two leads 16. A change to a field shape or field shape group within side view region 571 or depth region 574 will display a respective change in the other region within stimulation region 570. In this manner the clinician may be able to quickly view the field shape with respect to the respective lead. In addition, GUI 564 may include a slider or other adjustment mechanism to pan down the length of lead 596A and lead 596B. A corresponding slider may be present within stimulation region 570 as a marker to the axial location of depth region 574.

Figure 24:
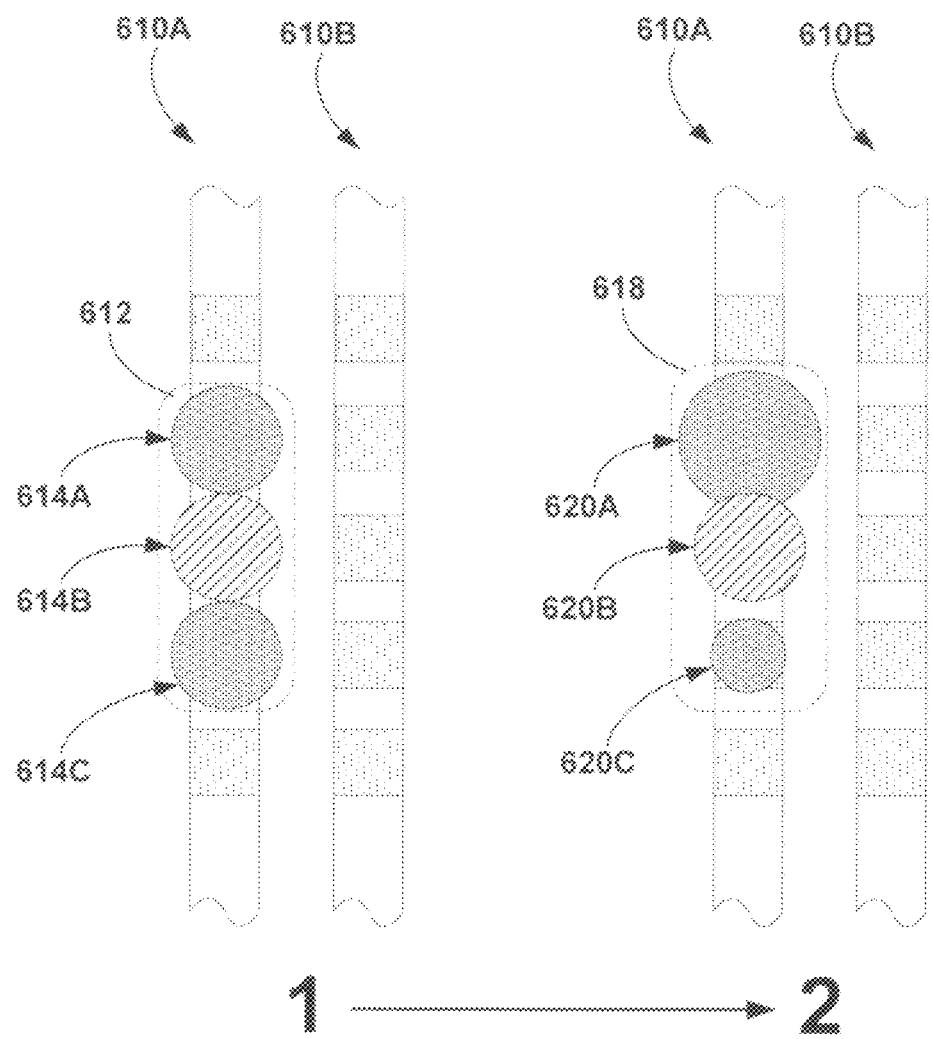
FIG. 24 is a conceptual illustration of a resizing sequence for a group of activation and inhibition icons.

FIG. 24 illustrates an example how field shapes grow or shrink at the request of the clinician. Step one shows field shapes 614A, 614B and 614C as field shape group 612. Field shape group 612 is shown over lead r 610A instead of lead representation 610B. Field shape group 612 may be initially selected by the clinician from field shape manipulation tool menu 572 of GUI 564, for example. Field shape group 612 shows activation and inhibition created by stimulation from the electrodes of the lead represented by 610A. Specifically, field shapes 614A and 614C are inhibition field shapes and field shape 614B is an activation field shape.

In one example, field shapes 614B may have a size defined by a current of 10 milliamps (mA) while both inhibition field shapes 614A and 614C are created with 5 mA of current amplitude. In step two, the clinician has decided to shrink field shape 614C by changing the current amplitude of field shape 620C to 2 mA of current. In addition, the clinician has increased the field shape 614A by changing the current amplitude of field shape 620A to 8 mA of current and field shape 620B has not changed in size from field shape 614B. This change of inhibition field shapes 620A and 620C in step two may alter the effect of stimulation therapy to patient 12. In some examples the changes between field shape groups 612 and 618 may occur in several discrete steps or a substantially continuous manner to reduce any perceived transition effect to patient 12 during real-time programming and stimulation.

A change in a field shape size, such as that between field shape 614A and 620A, may correspond to any one of voltage amplitude, current amplitude, pulse width, power output, or iterative combination of these parameters. As shown between field shape groups 612 and 618 of FIG. 24, shrinking of field shape 614C to 620C within field shape group 618 may cause relative changes to field shape 620A in order to maintain inhibition or activation currents within field shape group 618. This may occur in order for the current to be balanced between the sources and sinks (activation areas and inhibition areas) of the stimulation therapy. However, the clinician may also increase or decrease other field shapes, such as activation field shape 620B in order to balance current within field shape group 618. In alternative embodiments, the clinician or system 10 may add or subtract other field shapes when needed to address any current issues without significantly altering the stimulation therapy of patient 12.

Figure 25:
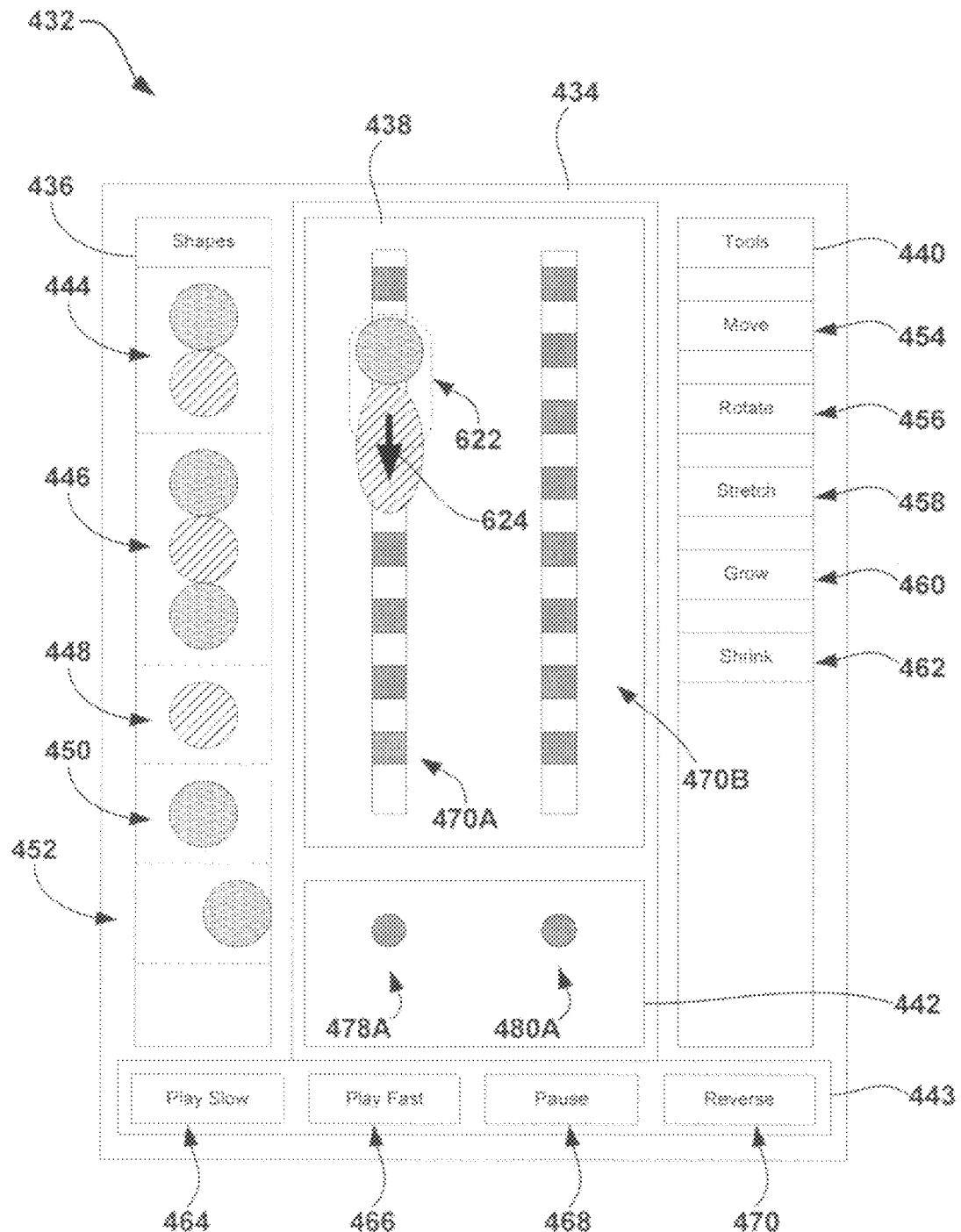
FIG. 25 is a conceptual illustration of a user interface with activation and inhibition icons stretched within the stimulation region.

FIG. 25 provides an example illustrating how the clinician may stretch field shape 624 within stimulation region 438 with reference to GUI 432. To adjust a field shape within field shape group 622, the clinician may first select stretch icon 458 within manipulation tool menu 440 and then select the field shape or field shape combination to be stretched. As shown in FIG. 25, the clinician has selected the activation field shape within field shape group 622. The clinician may grab an outer edge of the activation field shape and drag the side of the activation field shape until the field shape has been stretched to the satisfaction of the clinician or the limits possible of system 10. Arrow 624 indicates the direction in which the clinician has stretched the activation field shape. Arrow 624 may remain over the activation field shape to indicate that the stretch action is pending approval from the clinician. Instead of arrow 624, other pending indications may include animations, dotted lines, flag icons, transparencies, or any other representation that a stretch action has been performed to field shape group 622 within stimulation region 438. In other examples, the clinician may select to stretch the entire field shape group or a different field shape.

When delivering therapy to patient 12 in real-time, stretching the activation field shape may occur without immediately modifying stimulation during the stretching period. In order to implement the stretch change into the stimulation therapy, the clinician may utilize implementation toolbar 443. Implementation toolbar 443 may allow the clinician to control how and when the change is transferred to stimulator 14 for delivery to patient 12.

Implementation toolbar 443 includes play slow icon 464, play fast icon 466, pause icon 468, and reverse icon 470, similar to a video or audio playback system. Play slow icon 464 and play fast icon 466 indicate how stimulator 14 is to change therapy to the stretched field shape group 622 within stimulation region 438. In other words, the clinician may have control of how stimulator 14 shifts from the old therapy using the original field shape group to the new therapy utilizing the new stretched field shape group. This control may only be necessary when the clinician is providing stimulation therapy according to the programming in real-time. The clinician may pause the change in stimulation by selecting pause icon 468 or reverse the change back to the original stimulation by selecting reverse icon 470. Furthermore, in other implementation toolbar embodiments, as described above, a clinician may discretely control each of a plurality of steps from the original field shape to the stretched field shape using, for example, arrow buttons provided by the GUI.

Figure 26A:
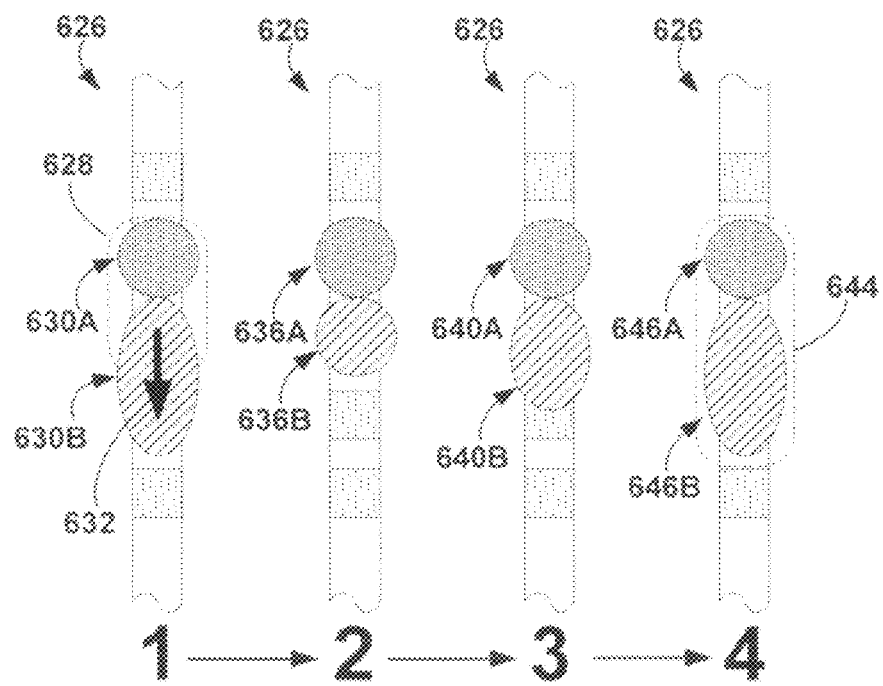
FIGS. 26A-26B are conceptual illustrations of stretch sequences for a group of activation and inhibition icons.
Figure 26B:
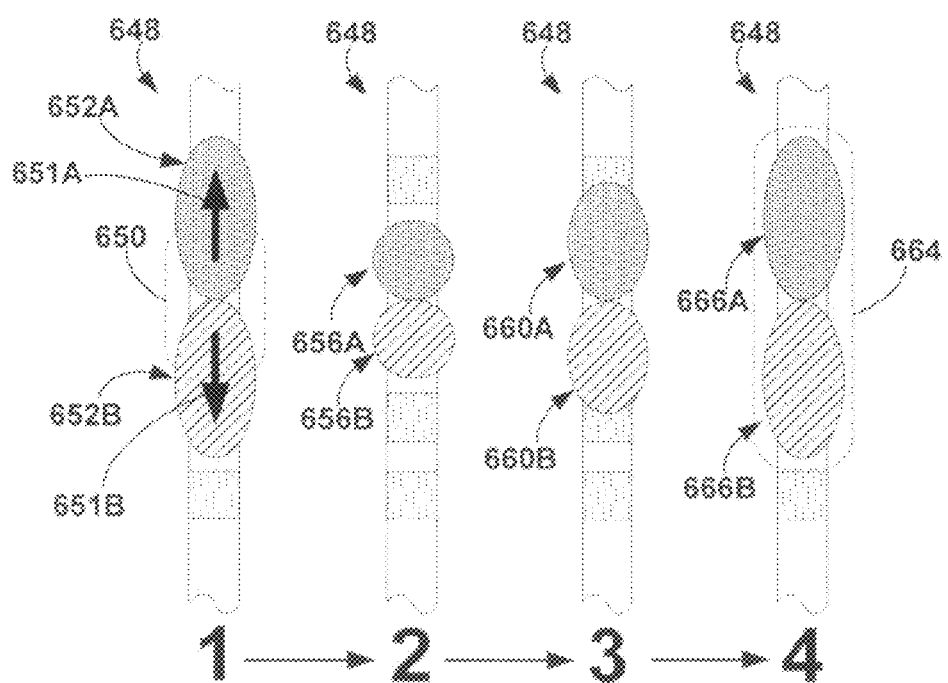

FIGS. 26A and 26B provide example methods of stretching one or more field shapes as described in FIG. 25 above. The steps of stretching the field shapes may require the use of multiple current sources within stimulator 14 in order to supply differing electrical parameters to multiple electrodes that simulate partial electrodes. As shown in FIG. 26A, field shape group 628 includes field shape 630A and 630B. Step one illustrates arrow 632 that indicates the direction in which the clinician desires to stretch activation field shape 630B over lead representation 626. Field shape 630A is not stretched in the example of FIG. 26A.

In order to stretch activation field shape 630B in the direction of the arrow 632, stimulator 14 uses a partial electrode to slightly stretch the geometry of field shape 630B in the direction of arrow 632. Step two shows the initial field shapes 636A and 636B, each centered over their respective electrode. In step three, field shape 640A remains unchanged, but field shape 640B is stretched away from field shape 640A through the use of a partial electrode on the adjacent electrode. Step four indicates that field shape 646B is completely stretched over two electrodes, including another cathode in the direction of arrow 632, while field shape 646A remains unchanged. Field shape 646A and 646B create the new field shape group 644 that the clinician may used to deliver therapy. In other examples, the clinician may stretch activation field shape 646B over more than two full electrodes.

FIG. 26B shows the entire field shape group 650 about to be stretched over four electrodes of lead representation 648. According to the instructions of the clinician, field shape 652A is stretched in the direction of arrow 651A. In addition, field shape 652B is stretched in the direction of arrow 651B. Arrows 651A and 651B are representations of the direction that both inhibition field shape 652A and activation field shape 652B are to be stretched by stimulator 14.

Step two shows each of field shapes 656A and 656B over only one electrode of lead representation 648. In step three, both field shapes 660A and 660B are stretched incrementally in opposite directions by using partial electrodes adjacent to the original electrodes for field shapes 656A and 656B. In step four, both field shapes 666A and 666B are completely stretched over two electrodes of lead representation 648. Field shapes 666A and 666B create the new field shape group 664 that defines stimulation therapy to patient 12. In some embodiments, the clinician may be able to stretch one field shape before stretching the other field shape. Alternatively, field shapes 656A and 656B may be stretched in an alternating and iterative manner such that patient 12 may generally feel a smooth change in stimulation.

In examples of stimulator 14 that only include a single current source, stretching field shapes may not be accomplished with partial electrode stretching. In this case, simulator 14 may need to coarsely stretch the field shape by adding the appropriate anode or cathode to the next full electrode on the lead. While this method may cause patient 12 to notice abrupt changes in stimulation therapy, stimulator 14 may be able to minimize the noticeable change. For example, stimulator 14 may slowly ramp up the current or voltage amplitude of the additional full electrode until the full amplitude is achieved.

Figure 27A:
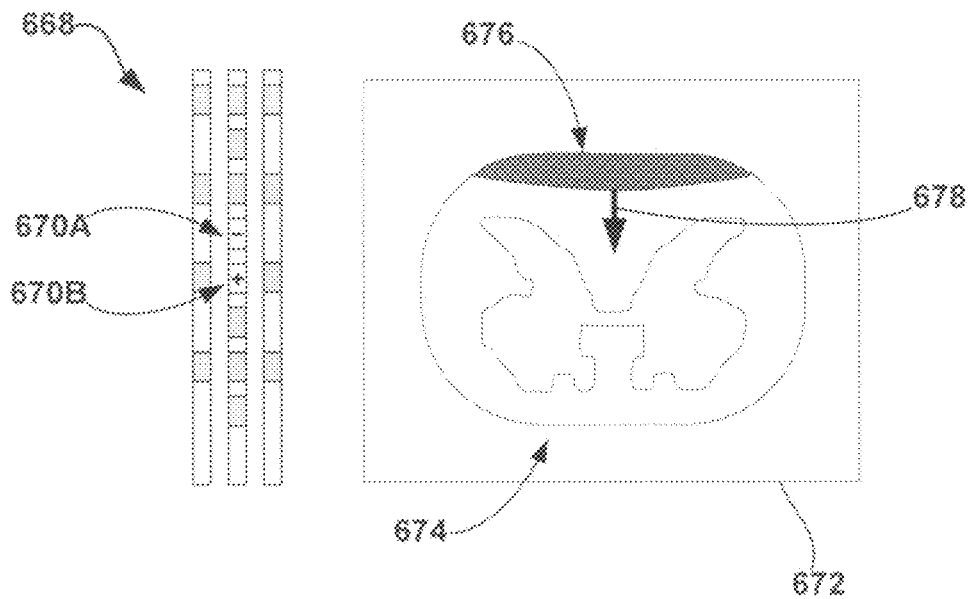
FIGS. 27A and 27B are conceptual illustrations of different electrode combinations to drive activation deeper within the tissue of a patient.
Figure 27B:
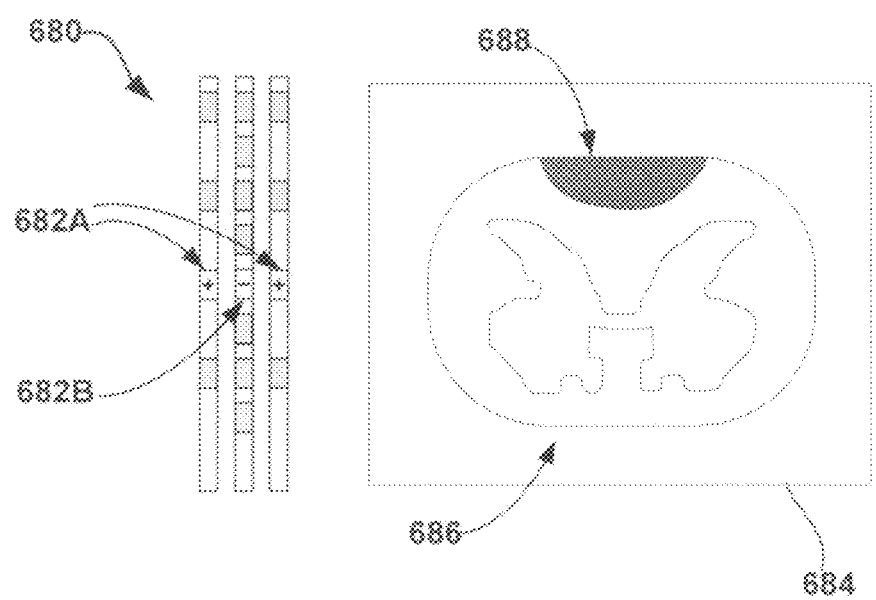

FIGS. 27A and 27B illustrate example leads and electrode configurations and corresponding axial views of stimulation depth on programmer 20 to allow the clinician to identify how stimulation therapy affects patient 12 tissue. Specifically, the stimulation may be viewed within the spinal cord as modeled by programmer 20. In addition to allowing the clinician to adjust field shapes within the a longitudinal view of the stimulation region, the clinician may be able to view the depth of neuron activation directly in the axial view. As shown in FIG. 27A, electrode configuration 668 includes one cathode 670A and one anode 670B. Electrode configuration 668 results in neuron activation 676 shown in axial view 672. Neuron activation 676 is shown within spinal cord 674. Neuron activation 676 shows the current stimulation therapy as a shallow and spread out region in spinal cord 674. The clinician may select and drag neuron activation 676 towards the center of spinal cord 674 in the direction of arrow 678.

FIG. 27B illustrates changes to stimulation therapy with altered neuron activation 688 from neuron activation 676 in FIG. 27A. By dragging neuron activation 676 in the direction arrow 678, programmer 20 generated a new electrode configuration 680 in order to accommodate the desired changes to therapy. Electrode configuration 680 includes a center cathode 682B with anodes 682A on either side of the cathode to create stimulation reaching a deeper area within spinal cord 686. Neuron activation 688 is shown in axial view 684. Processor 22 may automatically make the change to electrode configuration 680 in order to drive stimulation deeper into spinal cord of patient 12. Processor 22 may accomplish these changes to therapy by selecting a pre-computed or predefined field shape that most closely accomplishes clinician's goal by calculating the parameters in real time that would most closely match the desired field shape. Accordingly, axial view 684 indicates with neuron activation 688 that stimulation is deeper and less spread out along the surface of spinal cord 686. The change in stimulation and associated electrode configuration 680 of cathodes and anodes may be made in an iterative manner to minimize the impact of the change in stimulation on patient 12. In other cases, programmer 20 may change to electrode configuration 680 in one step from electrode configuration 668. The depth change shown in FIG. 27B may be similar to a grow or shrink action discussed above within the stimulation region of a GUI.

FIGS. 27A and 27B illustrate that the change from electrode configuration 668 to electrode configuration 680 alters the current density between anodes and cathodes to essentially focus the current to a particular area of spinal cord 686. However, the clinician may instead change the depth of the stimulation through modifying any one or more of current amplitude, voltage amplitude, pulse width, pulse rate, or any other stimulation parameter. In addition, a combination of electrode configuration changes and parameter changes may be used to adjust the depth of the stimulation therapy.

Figure 28:
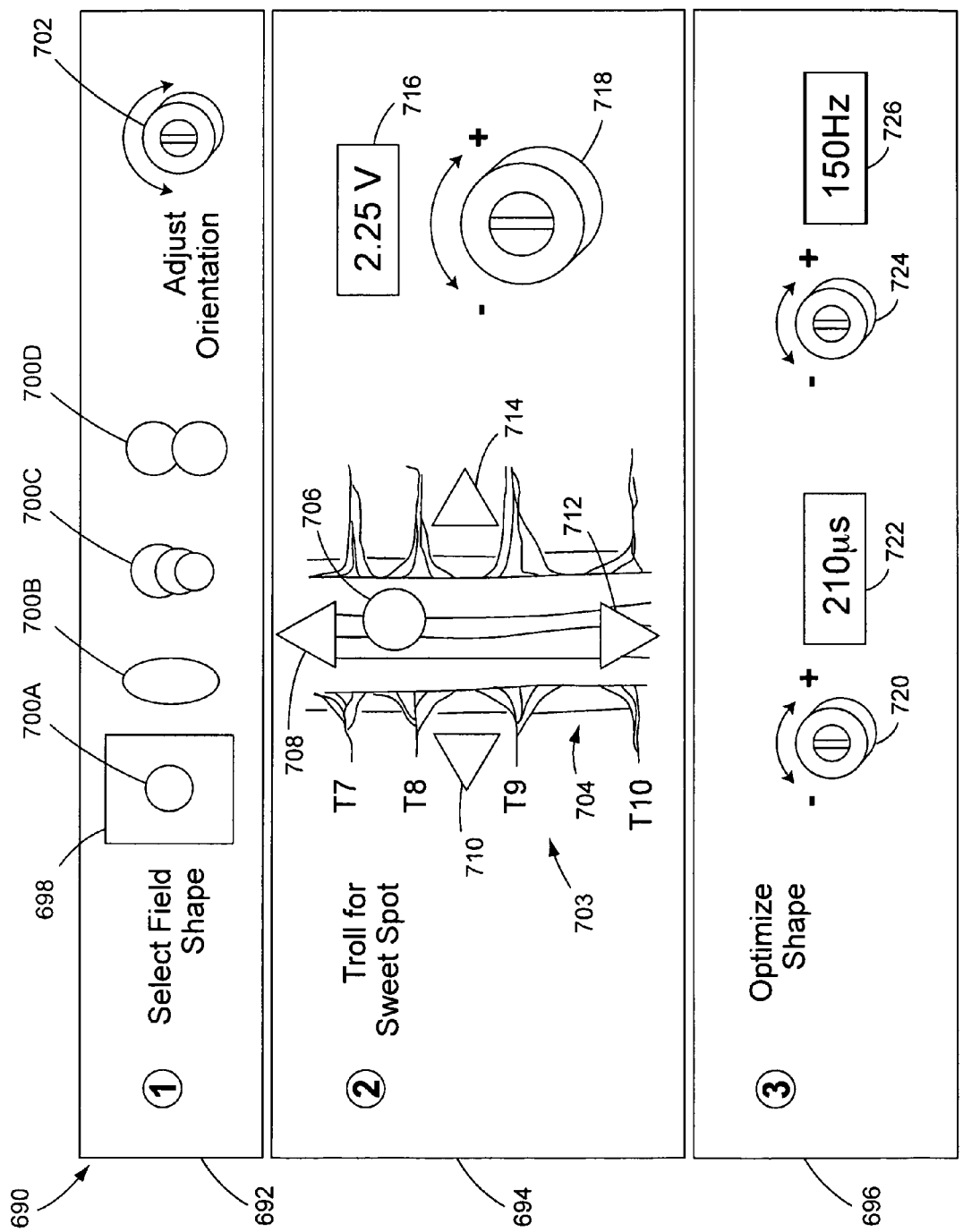
FIGS. 28-29 are conceptual illustrations of user interfaces that allows a user to select a field shape, place the field shape within a stimulation region, and modify the field shape.

FIG. 28 is an example screen shot of GUI 690 that allows the clinician to use one or more field shapes to program stimulation therapy. GUI 690 includes three zones, e.g., zones 692, 694 and 696, for programming. These zones may be provided on programmer 20 in one, two, three, or more screens. First zone 692 allows the clinician to select a one of field shapes 700A, 700B, 700C or 700D (collectively "field shapes 700"). The clinician uses selection box 698 to highlight the one of field shapes 700 to use in defining the stimulation therapy. Field shape 700A is a single field shape, field shape 700B is an elongated field shape that uses multiple electrodes, field shape 700C is a tripole field shape group, and field shape 700D is a bipole field shape group. Field shapes 700 may be of any type described herein, such as a current density field shape, an activation function field shape, or a neuron activation field shape. The adjust orientation knob 702 may be provided to allow the clinician to rotate the selected one of field shapes 700 as desired to be placed within stimulation region 703 of second zone 694.

Second zone 694 of GUI 690 allows the clinician to place the selected field shape 706 within stimulation region 703. Stimulation region 703 includes a general representation of spinal cord 704 of patient 12 that may or may not exactly match the anatomy of patient 12. As shown, the clinician has placed field shape 706 over spinal cord 703 near the T8 vertebra. The clinician may select any of arrows 708, 710, 712 or 714 to move field shape 706 as desired within stimulation field 703, e.g., left, right, up, down. The clinician may also place more than one field shape or field shape group within stimulation field 703 to the extent that stimulator 14 supports the stimulation.

The clinician may also use amplitude knob 718 to adjust the voltage amplitude. Adjusting amplitude knob 718 may accordingly adjust the size of field shape 706 within stimulation region 703. When the amplitude of field shape 706 is adjusted, amplitude indicator 716 may change respectively. In the example of FIG. 28, the voltage amplitude being used for field shape 706 is 2.25 volts. In other examples, amplitude knob 718 and corresponding amplitude indicator 716 may be used to adjust current amplitude instead of voltage amplitude. The amplitude adjusted in second zone 694 may depend upon the configuration of stimulator 14 and/or the desires of the clinician. While stimulation region 703 only provides a side view of spinal cord 704, other examples of GUI 690 may include a depth view that shows the relation of field shape 706 to spinal cord 704.

Third zone 696 of GUI 690 allows the clinician to make fine adjustments to the shape of field shape 706 before or during application of the therapy to patient 12. Example adjustments may include pulse width knob 720 and pulse frequency knob 724. Adjustment of one of the knobs 720 or 724 in third zone 696 may also result in a change the shape of field shape 706 displayed in stimulation region 706. Pulse width indicator 722 and pulse frequency indicator 726 are also provided to show the numerical stimulation parameter that currently defines field shape 706. Third zone 696 may also include other adjustments that the clinician may utilize in order to create the desired therapy from field shapes placed within stimulation region 703. While some adjustments to stimulation parameters are shown as knobs, the adjustments may be accomplished using sliders, up and down arrows, text fields, plus/minus buttons, joysticks, scroll wheels, or any other input media.

Figure 29:
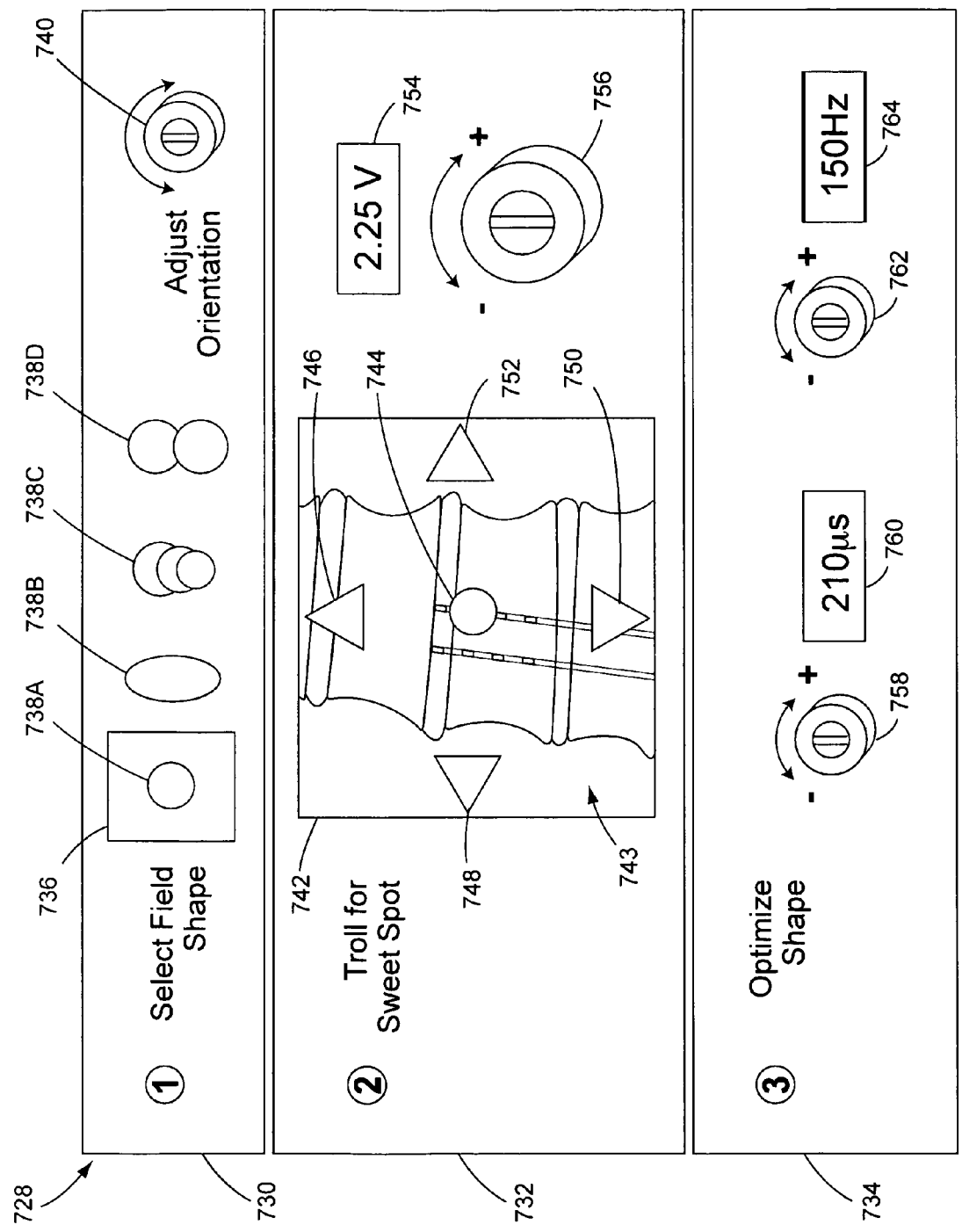

FIG. 29 is another example of a screen shot of GUI 728 that allows the clinician to program stimulation therapy. GUI 728 of FIG. 29 is substantially similar to GUI 690 of FIG. 28. However, GUI 728 provides an exact representation of patient 12 anatomy with the implanted leads (e.g., leads 16). GUI 728 includes first zone 730, second zone 732 and third zone 734. Field shapes 738A, 738B, 738C and 738D are provided to the clinician and may be selected via selection box 736. The clinician may change the orientation of the field shape via adjust orientation knob 740 and precisely position field shape 744, or other field shapes, with arrows 746, 748, 750 and 752. Second zone 732 also allows the clinician to adjust the voltage or current amplitude via amplitude adjustment knob 756 and amplitude indicator 754. Third zone 734 provides pulse width knob 758, pulse width indicator 760, pulse frequency knob 762, and pulse frequency indicator 764 in order for the clinician to adjust the stimulation parameters of field shape 744 and any other field shapes within stimulation field 743.

Image 742 that is used as background for stimulation region 743 may be taken post-surgery from patient 12 and mapped to the coordinate system of programmer 20 to ensure correct placement of the field shapes within stimulation region 742. In this manner, the clinician may directly identify anatomical positions of the spinal cord and associated implanted electrodes. As shown, the clinician has selected field shape 744 and positioned field shape 744 over the second electrode of the right lead. Image 742 may be generated from fluoroscopy, but other images may be provided that are generated from x-ray, MRI, CT, PET, or any other imaging modality. In other examples, image 742 of patient 12 anatomy may be provided and the clinician may manually indicate the location of each lead based upon surgical implantation results.

Field shapes as described herein are discussed as related to two dimensional programming using ring electrodes, but these methods of programming electrical stimulation may also be used within three-dimensional (3D) programming application with ring electrodes or with multiple electrodes arranged around the circumference of the lead, e.g., complex electrode array geometries. 3D programming may be useful in SCS application and, more specifically, within DBS applications where target tissues may be at a particular location around the circumference of each lead. By stimulating only the target tissues, the stimulation therapy may avoid stimulation of additional tissues that may cause adverse effects in patient 12. The clinician may focus on the activation of tissue by using field shapes within 3D programming environments. Otherwise, the clinician may spend time trying to identify individual stimulation parameters that may cause certain activation or inhibition of tissue.

Many embodiments of the disclosure have been described. Various modifications may be made without departing from the scope of the claims. These and other embodiments are within the scope of the following claims.

The invention claimed is:

1. A method comprising:
presenting on a display at least one view of a representation of a stimulation region;
presenting, simultaneously on the display, a plurality of different field shape groups within a field shape selection menu different than the representation of the stimulation region, wherein each of the field shape groups presented within the field shape selection menu comprises one or more shapes representing one or more stimulation fields able to be applied to the stimulation region by a medical device;
receiving selection input from a user selecting one of the field shape groups from the field shape selection menu;
receiving placement input from the user placing the selected field shape group at a position within the representation of the stimulation region; and
generating electrical stimulation parameters based upon the selected field shape group and the position of the selected field shape group within the representation of the stimulation region.

2. The method of claim 1, wherein the field shape group displays at least one of an activation function, a predicted neuron activation, or a current density.

3. The method of claim 2, wherein the field shape group displaying the activation function comprises at least one activation field shape that indicates activation of tissue activity by a cathode and at least one inhibition field shape that indicates inhibition of tissue activity by an anode.

4. The method of claim 1, further comprising snapping the field shape group to an electrode closest to the placement within the stimulation region.

5. The method of claim 1, further comprising:
presenting on the display at least one manipulation icon within a manipulation tool menu; and
receiving from the user a manipulation input via the at least one manipulation icon that manipulates the selected at least one field shape within the representation of the stimulation region.

6. The method of claim 1, further comprising presenting on the display within the representation of the stimulation region at least one of a representation of an implantable lead, a representation of one or more electrodes, or a representation of patient anatomy that corresponds to the stimulation region.

7. The method of claim 6, wherein the representation of anatomy comprises at least one of a somatotopic map, a tissue image, or an anatomical atlas.

8. The method of claim 7, wherein the tissue image is representative of the patient and generated via at least one of fluoroscopy, magnetic resonance imaging, X-ray, computed tomography, or positron emission tomography.

9. The method of claim 7, wherein the anatomical atlas is a general representation of human anatomy.

10. The method of claim 1, further comprising:
restricting at least one unusable electrode from a set of electrodes implanted within a patient to deliver stimulation therapy according to the generated electrical stimulation parameters; and blocking placement of the selected field shape group at an area of the representation of the stimulation region associated with the at least one unusable electrode.

11. The method of claim 1, wherein the representation of the stimulation region illustrates a side view of the stimulation region.

12. The method of claim 1, wherein the stimulation region illustrates a stimulation depth region, wherein the stimulation depth region illustrates the penetration of the selected field shape group into tissue.

13. A programmer comprising:
   a display;
   a processor configured to present on the display at least one view of a representation of a stimulation region and present, simultaneously on the display, a plurality of different field shape groups within a field shape selection menu different than the representation of the stimulation region, wherein each of the field shape groups presented within the field shape selection menu comprises one or more shapes representing one or more stimulation fields able to be applied to the stimulation region by a medical device; and
   a user interface configured to receive selection input selecting one of the field shape groups from the field shape selection menu and placement input placing the selected field shape group at a position within the stimulation region, wherein the processor is configured to generate electrical stimulation parameters based upon the selected field shape group and the position of the selected field shape group within the representation of the stimulation region.

14. The programmer of claim 13, further comprising a memory configured to store field shape information that the processor uses to display the at least one field shape group as an activation function, a predicted neuron activation, or a current density.

15. The programmer of claim 13, wherein the processor is configured to snap the at least one field shape group to an electrode closest to the placement within the representation of the stimulation region.

16. The programmer of claim 13, wherein the processor is configured to present on the display at least one manipulation icon within a manipulation tool menu, and the user interface is configured to receive a manipulation input via the at least one manipulation icon that manipulates the at least one field shape selected within the representation of the stimulation region.

17. The programmer of claim 13, wherein the processor is configured to present on the display within the representation of the stimulation region at least one of a representation of an implantable lead, a representation of one or more electrodes, or a representation of patient anatomy that corresponds to the representation of the stimulation region.

18. The programmer of claim 13, wherein the processor is configured to:
   restrict at least one unusable electrode from a set of electrodes implanted within a patient to deliver stimulation therapy according to the generated electrical stimulation parameters; and
   block placement of the selected field shape group at an area of the representation of the stimulation region associated with the at least one unusable electrode.

19. The programmer of claim 13, wherein the user interface comprises the display.

20. A computer readable storage medium comprising instructions that cause a processor to:
   present on a display at least one view of a representation of a stimulation region;
   present, simultaneously on the display, a plurality of different field shape groups within a field shape selection menu different than the representation of the stimulation region, wherein each of the field shape groups presented within the field shape selection menu comprises one or more shapes representing one or more stimulation fields able to be applied to the stimulation region by a medical device;
   receive selection input selecting one of the field shape groups from the field shape selection menu;
   receive placement input placing the selected field shape group at a position within the stimulation region; and
   generate electrical stimulation parameters based upon the selected field shape group and the position of the selected field shape group within the representation of the stimulation region.

21. The computer readable storage medium of claim 20, further comprising instructions that cause the processor to snap the field shape group to an electrode closest to the placement within the representation of the stimulation region.

22. The computer readable storage medium of claim 20, further comprising instructions that cause the processor to present on the display at least one manipulation icon within a manipulation tool menu, receive a manipulation input from the at least one manipulation icon within a manipulation tool menu that manipulates the at least one field shape selected within the representation of the stimulation region.

23. The computer readable storage medium of claim 20, further comprising instructions that cause the processor to present on the display within the representation of the stimulation region at least one of a representation of an implantable lead, a representation of one or more electrodes, or a representation of patient anatomy that corresponds to the stimulation region.

24. The computer readable storage medium of claim 20, further comprising instructions that cause the processor to:
   restrict at least one unusable electrode from a set of electrodes implanted within a patient to deliver stimulation therapy according to the generated electrical stimulation parameters; and
   block placement of the selected field shape group at an area of the representation of the stimulation region associated with the at least one unusable electrode.

25. The computer readable storage medium of claim 20, wherein the field shape group displays at least one of an activation function, a predicted neuron activation, or a current density.

* * * * *